(12) United States Patent
Scott et al.

(10) Patent No.: US 11,801,229 B2
(45) Date of Patent: Oct. 31, 2023

(54) MOLECULAR ENTRAPMENT VIA HOMOPOLYMER SELF-ASSEMBLY

(71) Applicant: Northwestern University, Evanston, IL (US)

(72) Inventors: Evan A. Scott, Evanston, IL (US); Fanfan Du, Evanston, IL (US); Baofu Qiao, Evanston, IL (US); Monica Olvera de la Cruz, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/942,228

(22) Filed: Jul. 29, 2020

(65) Prior Publication Data
US 2021/0030690 A1    Feb. 4, 2021

Related U.S. Application Data

(60) Provisional application No. 62/879,637, filed on Jul. 29, 2019.

(51) Int. Cl.
*A61K 9/51* (2006.01)
*A61K 9/107* (2006.01)
*C08G 75/24* (2006.01)

(52) U.S. Cl.
CPC ............ *A61K 9/5146* (2013.01); *A61K 9/107* (2013.01); *A61K 9/5192* (2013.01); *C08G 75/24* (2013.01)

(58) Field of Classification Search
None
See application file for complete search history.

(56) References Cited

U.S. PATENT DOCUMENTS

2008/0138418 A1* 6/2008 Lee ...................... A61K 9/5138
                                                                      977/788
2021/0360934 A1   11/2021 Martinez et al.

FOREIGN PATENT DOCUMENTS

CN      110869038 A  *  3/2020  ............. A01N 63/50
WO   WO-0188541 A1  * 11/2001  ....... G01N 33/54346

OTHER PUBLICATIONS

English translation of CN-110869038-A (Mar. 2020) (Year: 2020).*
English translation of WO-0188541-A1 (Nov. 2001) (Year: 2001).*
Napoli et al. Oxidation-responsive polymeric vesicles. Nature Mater 3, 183-189 (2004) (Year: 2004).*
Allen SD, et al. Polymersomes scalably fabricated via flash nanoprecipitation are non-toxic in non-human primates and associate with leukocytes in the spleen and kidney following intravenous administration. Nano Research. 2018.
Allen, S. et al, Facile assembly and loading of theranostic polymersomes via multi-impingement flash nanoprecipitation. Journal of Controlled Release 262, 91 (2017).
Ashley JD, et al. Dual Carfilzomib and Doxorubicin-Loaded Liposomal Nanoparticles for Synergistic Efficacy in Multiple Myeloma. Molecular Cancer Therapeutics. 2016;15(7):1452-9.
Bai Y., et al., Protein self-assembly via supramolecular strategies. Chemical Society reviews 45, 2756 (2016).
Bearinger, J.P., et al., Chemisorbed poly(propylene sulphide)-based copolymers resist biomolecular interactions. Nature Materials, 2003. 2: p. 259.
Bobbala S, et al. Is There an Optimal Formulation and Delivery Strategy for Subunit Vaccines? Pharm Res. 2016;33(9):2078-97.
Bobbala S, et al. Poloxamer 407-chitosan grafted thermoresponsive hydrogels achieve synchronous and sustained release of antigen and adjuvant from single-shot vaccines. Immunology and cell biology. 2018.
Bordwell, FG et al, The Effect of the Sulfonyl Group on the Nucleophilic Displacement of Halogen in a-Halo Sulfones and Related Substances1. Journal of the American Chemical Society 73, 5184 (1951).
Boyken, SE et al, De novo design of protein homo-oligomers with modular hydrogen-bond network-mediated specificity. Science 352, 680 (2016).
Butawan M, et al. Methylsulfonylmethane: Applications and Safety of a Novel Dietary Supplement. Nutrients. 2017;9(3). Epub Mar. 17, 2017.
Cabral, H., et al., Block Copolymer Micelles in Nanomedicine Applications. Chemical Reviews, 2018. 118(14): p. 6844-6892.
Carugo D, et al. Liposome production by microfluidics: potential and limiting factors. Scientific Reports. 2016,6(1):25876.
Castro, CE et al., Mechanical design of DNA nanostructures. Nanoscale 7, 5913 (2015).
Cerritelli, S. et al., PEG-SS-PPS:? Reduction-Sensitive Disulfide Block Copolymer Vesicles for Intracellular Drug Delivery. Biomacromolecules 8, 1966 (2007).
cgmartini.nl. Martini 3 Open-Beta Release. Jul. 31, 2018. Available online at https://web.archive.org/web/20180821103013/http://cgmartini.nl/index.php/martini3beta.
Che, H., et al, Feedback-Induced Temporal Control of "Breathing" Polymersomes to Create Self-Adaptive Nanoreactors. Journal of the American Chemical Society, 2018. 140(16): p. 5356-5359.
Chen, S. et al, Dynamic Ordering and Phase Segregation in Hydrogen-Bonded Polymers. Accounts of Chemical Research 49, 1409 (2016).
Choi, I et al, Preparing Semiconducting Nanoribbons with Tunable Length and Width via Crystallization-Driven Self-Assembly of a Simple Conjugated Homopolymer. Journal of the American Chemical Society 140, 17218 (2018).
Christian, D.A., et al., Polymersome carriers: From self-assembly to siRNA and protein therapeutics. European Journal of Pharmaceutics and Biopharmaceutics, 2009. 71(3): p. 463-474.
Claessens, M.M.A.E., et al., Actin-binding proteins sensitively mediate F-actin bundle stiffness. Nature Materials, 2006. 5(9): p. 748-753.

(Continued)

*Primary Examiner* — Aradhana Sasan
(74) *Attorney, Agent, or Firm* — Quarles & Brady LLP

(57) ABSTRACT

The present invention provides novel nanostructures comprising solution of $PPSU_{20}$. Methods of preparing the novel PPSU nanostructures, and applications of such nanostructures are also provided.

18 Claims, 35 Drawing Sheets

(56) References Cited

OTHER PUBLICATIONS

Clark, T. et al, Why are dimethyl sulfoxide and dimethyl sulfone such good solvents? Journal of Molecular Modeling 14, 689 (2008).

Darden, T., et al, Particle mesh Ewald: An N•log(N) method for Ewald sums in large systems. The Journal of Chemical Physics, 1993. 98(12): p. 10089-10092.

Discher, D.E. et al., Polymersomes. Annual Review of Biomedical Engineering, 2006. 8(1): p. 323-341.

Dou Y, et al. Sustained delivery by a cyclodextrin material-based nanocarrier potentiates antiatherosclerotic activity of rapamycin via selectively inhibiting mTORC1 in mice. J Control Release. 2016;235:48-62. Epub May 29, 2016.

Dowling DJ, et al. Toll-like receptor 8 agonist nanoparticles mimic immunomodulating effects of the live BCG vaccine and enhance neonatal innate and adaptive immune responses. J Allergy Clin Immunol. 2017;140(5):1339-50.

Du F, et al, Immunotheranostic Polymersomes Modulady Assembled from Tetrablock and Diblock Copolymers with Oxidation-Responsive Fluorescence. Cellular and Molecular Bioengineering 10, 357 (2017).

Du F, et al. Homopolymer Self-Assembly via Poly(propylene Sulfone) Networks. ChemRxiv. 2019.

Du F, et al., Sequential intracellular release of water-soluble cargos from Shell-crosslinked polymersomes. Journal of Controlled Release, 2018. 282: p. 90-100.

Elbert DL, et al. Stable isotope labeling tandem mass spectrometry (SILT): integration with peptide identification and extension to data-dependent scans. J Proteome Res. 2008;7(10):4546-56. Epub Sep. 9, 2008.

Eloy JO, et al. Liposomes as carriers of hydrophilic small molecule drugs: Strategies to enhance encapsulation and delivery. Colloids and Surfaces B: Biointerfaces. 2014;123:345-63.

Esser, L., et al., Gadolinium-functionalized nanoparticles for application as magnetic resonance imaging contrast agents via polymerization-induced self-assembly. Polymer Chemistry, 2016. 7(47): p. 7325-7337.

Essmann, U. et al, A smooth particle mesh Ewald method. The Journal of Chemical Physics 103, 8577 (1995).

Foster, JC et al, Getting into Shape: Reflections on a New Generation of Cylindrical Nanostructures' Self-Assembly Using Polymer Building Blocks. Journal of the American Chemical Society 141, 2742 (2019).

Freeman, R. et al, Reversible self-assembly of superstructured networks. Science 362, 808 (2018).

Gardel, M.L., et al., Elastic Behavior of Cross-Linked and Bundled Actin Networks. Science, 2004. 304(5675): p. 1301.

Gilroy, JB et al, Monodisperse cylindrical micelles by crystallization-driven living self-assembly. Nature Chemistry 2, 566 (2010).

Gorl, D et al, Supramolecular block copolymers by kinetically controlled co-self-assembly of planar and core-twisted perylene bisimides. Nature Communications 6, 7009 (2015).

Grimaldi, N., et al., Lipid-based nanovesicles for nanomedicine. Chemical Society Reviews, 2016. 45(23): p. 6520-6545.

Hess B, P-LINCS:? A Parallel Linear Constraint Solver for Molecular Simulation. Journal of Chemical Theory and Computation 4, 116 (2008).

Hess, B., et al., GROMACS 4:? Algorithms for Highly Efficient, Load-Balanced, and Scalable Molecular Simulation. Journal of Chemical Theory and Computation, 2008. 4(3): p. 435-447.

Hess, B., et al., LINCS: A linear constraint solver for molecular simulations. Journal of Computational Chemistry, 1997. 18(12): p. 1463-1472.

Huang, J., et al., CHARMM36m: an improved force field for folded and intrinsically disordered proteins. Nature Methods, 2016. 14: p. 71.

Karabin, NB et al, Sustained micellar delivery via inducible transitions in nanostructure morphology. Nature Communications 9, 624 (2018).

Li, J., et al., Therapeutic Vesicular Nanoreactors with Tumor-Specific Activation and Self-Destruction for Synergistic Tumor Ablation. Angewandte Chemie, 2017. 129(45): p. 14213-14218.

Li, L., et al., Self-assembly of random copolymers. Chemical Communications, 2014. 50(88): p. 13417-13432.

Lipfert, J., et al., Magnetic torque tweezers: measuring torsional stiffness in DNA and RecA-DNA filaments. Nature Methods, 2010. 7: p. 977.

Lowe, AB et al, Synthesis and Solution Properties of Zwitterionic Polymers. Chemical Reviews 102, 4177 (2002).

Mackerell, AD et al, All-Atom Empirical Potential for Molecular Modeling and Dynamics Studies of Proteins. The Journal of Physical Chemistry B 102, 3586 (1998).

Mai, Y et al, Self-assembly of block copolymers. Chemical Society Reviews 41, 5969 (2012).

Mark, P. et al, Structure and Dynamics of the TIP3P, SPC, and SPC/E Water Models at 298 K. The Journal of Physical Chemistry A 105, 9954 (2001).

Markwalter, C. E., et al. "Flash nanoprecipitation for the encapsulation of hydrophobic and hydrophilic compounds in polymeric nanoparticles." JoVE (Journal of Visualized Experiments) 143 (2019): e58757.

Marrink SJ, et al. Perspective on the Martini model. Chem Soc Rev. 2013;42(16):6801-22.

Marrink SJ, et al. The MARTINI Force Field: Coarse Grained Model for Biomolecular Simulations. J Phys Chem B. 2007;111(27):7812-24.

Miyamoto, S. et al, Settle: An analytical version of the SHAKE and RATTLE algorithm for rigid water models. Journal of Computational Chemistry 13, 952 (1992).

Monticelli L, et al. The MARTINI Coarse-Grained Force Field: Extension to Proteins. J Chem Theory Comput. 2008;4(5):819-34.

Napoli, A., et al., New Synthetic Methodologies for Amphiphilic Multiblock Copolymers of Ethylene Glycol and Propylene Sulfide. Macromolecules, 2001. 34(26): p. 8913-8917.

Napoli, A., et al., Oxidation-responsive polymeric vesicles. Nature Materials, 2004. 3: p. 183.

Nelson, R., et al., Structure of the cross-β spine of amyloid-like fibrils. Nature, 2005. 435(7043): p. 773-778.

Nicol, E., et al, A New Initiator System for the Living Thiiranes Ring-Opening Polymerization: A Way toward Star-Shaped Polythiiranes. Macromolecules, 1999. 32(13): p. 4485-4487.

Ortony, JH et al, Water Dynamics from the Surface to the Interior of a Supramolecular Nanostructure. Journal of the American Chemical Society 139, 8915 (2017).

Ovod V, et al. Exposure of the lysine in the gamma chain dodecapeptide of human fibrinogen is not enhanced by adsorption to poly(ethylene terephthalate) as measured by biotinylation and mass spectrometry. J Biomed Mater Res A. 2012;100(3):622-31. Epub Jan. 4, 2012.

Panganiban B, et al. Random Heteropolymers Preserve Protein Function in Foreign Environments. Science. 2018;359(6381):1239-43.

Pappas, CG et al, Dynamic peptide libraries for the discovery of supramolecular nanomaterials. Nature Nanotechnology 11, 960 (2016).

Periole X, et al. Combining an Elastic Network With a Coarse-Grained Molecular Force Field: Structure, Dynamics, and Intermolecular Recognition. J Chem Theory Comput. 2009;5(9):2531-43.

Plimpton S., Fast Parallel Algorithms for Short-Range Molecular Dynamics. Journal of Computational Physics 117, 1 (1995).

Poma AB, et al. Combining the MARTINI and Structure-Based Coarse-Grained Approaches for the Molecular Dynamics Studies of Conformational Transitions in Proteins. Journal of Chemical Theory and Computation. 2017;13(3):1366-74.

Prota G, et al. Peptide-specific T helper cells identified by MHC class II tetramers differentiate into several subtypes upon immunization with CAF01 adjuvanted H56 tuberculosis vaccine formulation. Vaccine. 2015;33(48):6823-30. Epub Oct. 24, 2015.

Qiao B, et al, Molecular Origins of Mesoscale Ordering in a Metalloamphiphile Phase. ACS Central Science 1, 493 (2015).

Qiao B, et al. (2018). Liquid worm-like and proto-micelles: water solubilization in amphiphile-oil solutions. Physical Chemistry Chemical Physics, 20(18), 12908-12915.

(56) References Cited

OTHER PUBLICATIONS

Qiao B, et al. "Mirror"-like Protein Dimers Stabilized by Local Heterogeneity at Protein Surfaces. The Journal of Physical Chemistry B. 2019;123(18):3907-15.

Qiao B, et al. An All-Atom Molecular Dynamics Study of Water-Dodecane Interface in the Presence of Octanol. The Journal of Physical Chemistry C. 2018;122(1):687-93.

Diao B, et al. Water Follows Polar and Nonpolar Protein Surface Domains. Proceedings of the National Academy of Sciences. 2019;116:19274-81.

Qiao B, et al., How Hydrogen Bonds Affect the Growth of Reverse Micelles around Coordinating Metal Ions. The Journal of Physical Chemistry Letters, 2014. 5(8): p. 1440-1444.

Rogers, WB et al, Using DNA to program the self-assembly of colloidal nanoparticles and microparticles. Nature Reviews Materials 1, 16008 (2016).

Rothemund, P.W.K., Folding DNA to create nanoscale shapes and patterns. Nature, 2006. 440(7082): p. 297-302.

Sato, K., et al., Peptide supramolecular materials for therapeutics. Chemical Society Reviews, 2018. 47(20): p. 7539-7551.

Sawaya, M.R., et al., Atomic structures of amyloid cross-β spines reveal varied steric zippers. Nature, 2007. 447: p. 453.

Scott EA, et al. Dendritic cell activation and T cell priming with adjuvant- and antigen-loaded oxidation-sensitive polymersomes. Biomaterials. 2012;33(26):6211-9.

Scott EA, et al. Mass spectrometric mapping of fibrinogen conformations at poly(ethylene terephthalate) interfaces. Biomaterials. 2007;28(27):3904-17. Epub Jun. 22, 2007.

Seeman, NC et al, DNA nanotechnology. Nature Reviews Materials 3, 17068 (2017).

Shang S, et al. Induction of *Mycobacterium tuberculosis* Lipid-Specific T Cell Responses by Pulmonary Delivery of Mycolic Acid-Loaded Polymeric Micellar Nanocarriers. Front Immunol. 2018;9:2709. Epub Dec. 13, 2018.

Souza PCT, et al. An Allosteric Pathway in Copper, Zinc Superoxide Dismutase Unravels the Molecular Mechanism of the G93A Amyotrophic Lateral Sclerosis-Linked Mutation. J Phys Chem Lett. 2019:7740-4.

Stano A, et al. Tunable T cell immunity towards a protein antigen using polymersomes vs. solid-core nanoparticles. Biomaterials. 2013;34(17):4339-46. Epub Mar. 13, 2013.

Strader, ML et al, A Flexible All-Atom Model of Dimethyl Sulfoxide for Molecular Dynamics Simulations. The Journal of Physical Chemistry A 106, 1074 (2002).

Tang, Z et al, Polymeric nanostructured materials for biomedical applications. Progress in Polymer Science 60, 86 (2016).

Teng, P. et al, Hydrogen-Bonding-Driven 3D Supramolecular Assembly of Peptidomimetic Zipper. J. Am. Chem. Soc. 140, 5661 (2018).

Vasdekis, AE et al, Precision Intracellular Delivery Based on Optofluidic Polymersome Rupture. ACS Nano 6, 7850 (2012).

Voorhaar, L. et al, Supramolecular polymer networks: hydrogels and bulk materials. Chemical Society Reviews, 2016. 45(14): p. 4013-4031.

Whitesides, G.M., et al, Molecular self-assembly and nanochemistry: a chemical strategy for the synthesis of nanostructures. Science, 1991. 254(5036): p. 1312.

Wilson DR, et al. Biodegradable STING agonist nanoparticles for enhanced cancer immunotherapy. Nanomedicine: Nanotechnology, Biology and Medicine. 2018;14(2):237-46.

Wojtecki, RJ et al, Using the dynamic bond to access macroscopically responsive structurally dynamic polymers. Nature materials 10, 14 (2011).

Wolf AJ, et al. Initiation of the adaptive immune response to *Mycobacterium tuberculosis* depends on antigen production in the local lymph node, not the lungs. J Exp Med. 2008;205(1):105-15. Epub Dec. 26, 2007.

Yan, J., et al., Optical Nanoimaging for Block Copolymer Self-Assembly. Journal of the American Chemical Society, 2015. 137(7): p. 2436-2439.

Yi S, et al. Surface Engineered Polymersomes for Enhanced Modulation of Dendritic Cells During Cardiovascular Immunotherapy. Advanced Functional Materials. 2019;29(42):1904399.

Yi S, et al. Tailoring Nanostructure Morphology for Enhanced Targeting of Dendritic Cells in Atherosclerosis. ACS Nano, 2016. 10(12): p. 11290-11303.

Yu, W. et al, Extension of the CHARMM general force field to sulfonyl-containing compounds and its utility in biomolecular simulations. Journal of Computational Chemistry 33, 2451 (2012).

Zhang, F. et al, Structural DNA Nanotechnology: State of the Art and Future Perspective. Journal of the American Chemical Society 136, 11198 (2014).

Zou, Q., et al., Biological Photothermal Nanodots Based on Self-Assembly of Peptide-Porphyrin Conjugates for Antitumor Therapy. Journal of the American Chemical Society, 2017. 139(5): p. 1921-1927.

\* cited by examiner

US 11,801,229 B2

MOLECULAR ENTRAPMENT VIA HOMOPOLYMER SELF-ASSEMBLY

CROSS-REFERENCE TO RELATED APPLICATIONS

This application claims priority to U.S. Provisional Application No. 62/879,637, filed on Jul. 29, 2019, the contents of which are incorporated herein by reference.

STATEMENT REGARDING FEDERALLY SPONSORED RESEARCH

This invention was made with government support under 1DP2HL 132390-01 awarded by the National Institutes of Health and DE-FG02-08ER46539 awarded by the Department of Energy. The government has certain rights in the invention.

BACKGROUND OF THE INVENTION

Self-assembly is ubiquitous in biological systems and underlies the formation of complex structures from simple components. Compared to the capabilities of natural polymers, such as polypeptides (1) and DNA (2), for dynamic assembly and reorganization via noncovalent interactions, synthetic polymer-based systems are relatively primitive (3). Such controlled aqueous self-assembly of single component supramolecular systems has remained a challenge for synthetic polymers, which typically require amphiphilicity or direct incorporation of naturally occurring peptide/nucleic acid monomers or derivatives thereof for controlled aggregation in aqueous systems. The most common synthetic self-assembling systems employ amphiphilic copolymers that are limited to separate hydrophobic and hydrophilic segments, which do not allow the complex dynamic self-assembly behavior observed in nature while also maintaining aggregate stability required for a broad range of applications. In terms of nanofabrication in aqueous solution, focus has been placed on the design of amphiphilic block (4) or random (5) copolymers wherein adjustment of the volume fraction of the hydrophobic/hydrophilic components permits fabrication of various nanostructures including spheres, cylinders, and vesicles. The multicomponent nature and dauntingly wide range of chemical compositions that have been developed for these self-assembling systems can present difficulties during chemical synthesis (6) and practical application (7), often requiring expertise in synthetic polymer chemistry and delaying translation of useful technologies.

There is a need for a simple, efficient method of producing monodisperse nanostructures using a single mixture that can be loaded with cargo at high efficiencies and can be used to carry cargo to a target.

SUMMARY OF THE INVENTION

The present disclosure provides novel nanostructures and nanogels of poly(propylene sulfone) homopolymers, specifically $PPSU_{20}$ homopolymers, DMSO/water systems for making them, and applications for use of such homopolymer for delivery of cargo. In some aspects, the $PPSU_{20}$ homopolymers are capable of self-assembling into nanostructures, both vesicle-like nanogels (nanoparticles) and bundle-like nanogels (nanobundles) that can be used for encapsulating both hydrophobic and water-soluble cargo, having exceptionally high loading efficiencies (greater than 90%, preferably greater than 95%) and also having high loading capacities (greater than 75%, preferably greater than 80% loading capacity m/m). The nanostructures are soluble and crystallizable within the same solvent, and using a DMSO/water system, wherein changes to the ratio of DMSO to water ratio and the stepwise addition of the water to the DMSO solution (containing the $PPSU_{20}$) allows for dynamic and reproducible formation of specific nanostructures as described in the Examples below. $PPSU_{20}$ is soluble in DMSO, and by the addition of water to the DMSO solution containing $PPSU_{20}$, the ability to form collapsed compact nanogels (e.g., bundle-like nanogels to vesicle-like nanogels).

The present disclosure provides a $PPSU_{20}$ DMSO/water system which, depending on the ratio of DMSO:water and the stepwise addition of water to the system, forms different sizes and structures of $PPSU_{20}$ homopolymer nanogels and nanostructures. These $PPSU_{20}$ nanostructures and nanogels can be used for delivery cargo/agents including for both hydrophobic and water-soluble agents.

In one aspect, the disclosure provides a synthetic self-assembling homopolymer for producing nanostructures comprising about 20 repeat units of poly(propylene sulfone) (PPSU).

In another aspect, the disclosure provides a system for delivery of cargo to a target, the system comprising: (a) a nanostructure of $PPSU_{20}$; and (b) a cargo, wherein the nanostructure is loaded with the cargo with a loading efficiency of at least 90%, preferably at least 95%.

In another aspect, the disclosure provides a method of producing a nanostructure capable of carrying a cargo, the method comprising: mixing water to a solution of DMSO: $PPSU_{20}$ (20 repeat units of poly(propylene sulfone)) at a ratio from about 2:1 to about 10:1 (by volume), preferably about 1:2 to about 1:5 to form a monodisperse nanostructure of $PPSU_{20}$ within the solution. In some aspects, the mixing the water to DMSO:$PPSU_{20}$ solution is performed stepwise in 1 to about 80 steps, wherein the solution is mixed after each addition of the water.

In yet another aspect, the present disclosure provides a $PPSU_{20}$ nanostructure made by the methods described herein.

In yet another aspect, the present disclosure provides a method of loading a cargo in a nanostructure capable of being delivered to a cell or target, the method comprising: (a) mixing water with a solution of DMSO and $PPSU_{20}$ (20 repeat units of poly(propylene sulfone)) at a ratio from about 2:1 to about 10:1 (by volume), preferably about 1:2 to about 1:5, wherein either the water or the solution comprises the cargo before mixing, and wherein the mixing forms a monodisperse nanostructure of $PPSU_{20}$ comprising the cargo.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

The present invention has been described in terms of one or more preferred embodiments, and it should be appreciated that many equivalents, alternatives, variations, and modifications, aside from those expressly stated, are possible and within the scope of the invention.

Nature exploits self-assembly processes to promote the formation of structurally dynamic hierarchical structures. The ability to design this dynamic behavior in synthetic materials is a central challenge of nanotechnology.

The present disclosure provides poly(propylene sulfone) (PPSU), a synthetic homopolymer capable of supramolecular self-assembly that is biomimetic of peptides and DNA. Experiments and simulations demonstrate that while PPSU is an extended solubilized chain in dimethyl sulfoxide (DMSO, $(CH_3)_2SO$), the addition of water greatly decreases its stiffness and induces bundling of PPSU chains into networks linked by short crystalline zipper segments. The PPSU zipper networks (ZipNets) trend towards collapse upon further hydration, allowing formation of dynamically controlled nanostructures with diverse morphologies and sizes. Drug loading efficiencies of the nanostructures for a wide range of polar payloads are nearly 100% with exceptionally high loading capacity (greater than 75% loading capacity, preferably greater than 90% load capacity, more preferably greater than 95% load capacity). This simple, nontoxic and facilely synthesized homopolymer presents a versatile platform for nanofabrication with potential applications in biomedicine, diagnostics, catalysis and purification.

Figure 2:
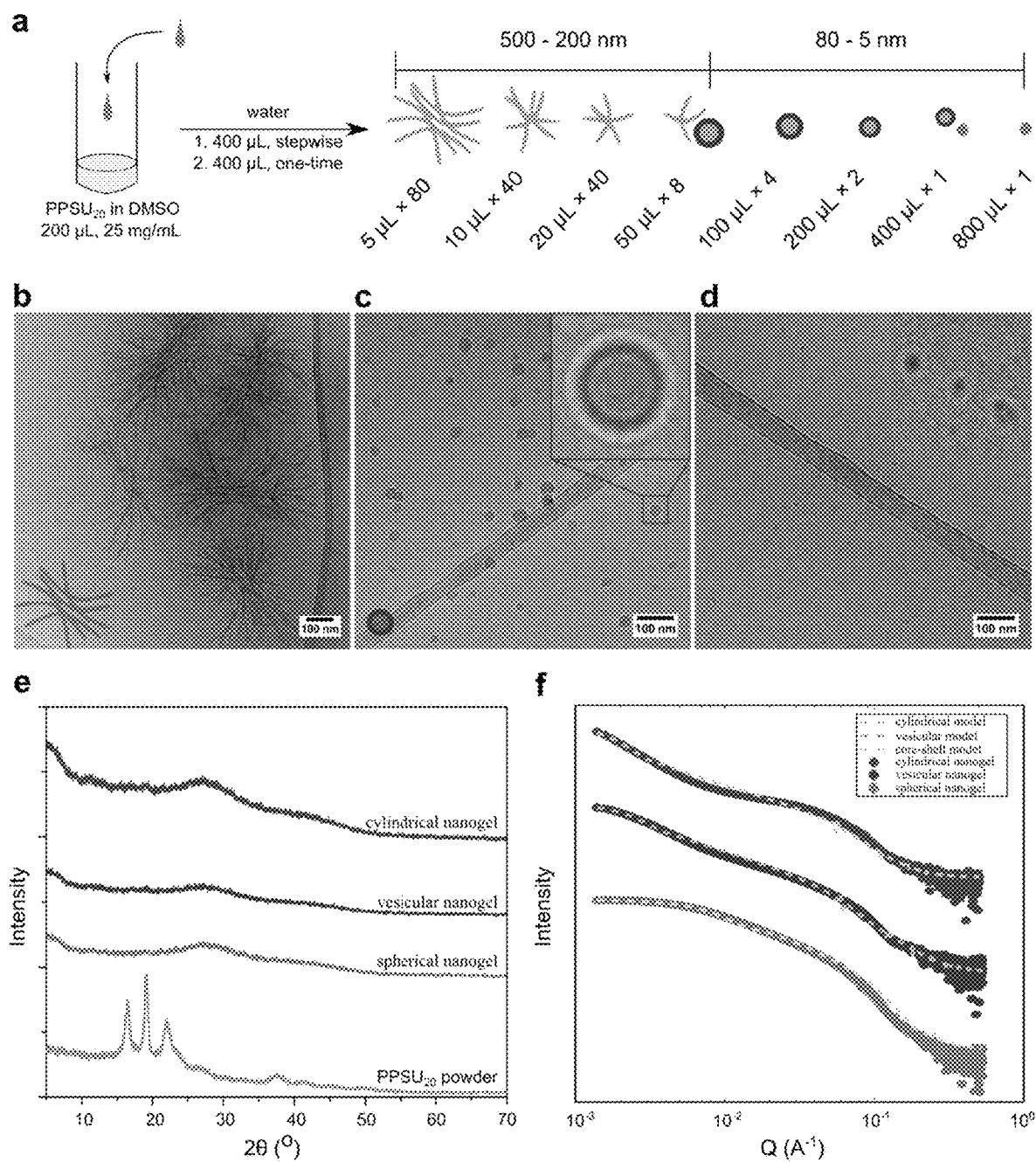
FIG. 2. Nanostructured hydrogels formed by PPSU$_{20}$ self-assembly. (a) Fabrication of nanoscale hydrogels with distinct morphologies by homopolymer self-assembly. Externally controlling the self-assembly of PPSU$_{20}$ by stepwise addition of water to DMSO solutions of PPSU$_{20}$. (b-d) Cryo-TEM images showing the typical cylindrical, vesicular, and spherical morphologies in water. Scale bar=100 nm. Nanostructures were prepared by stepwise hydration of PPSU$_{20}$ solutions (25 mg/mL in 200 μL DMSO): (b) 5 μL/step×80 steps; (c) 100 μL/step×4 steps; (d) 800 μL/step×1 step. (e) WXRD patterns of cylindrical (blue), vesicular (red) and spherical (green) nanogels, and a PPSU$_{20}$ powder comparison (gray). (f) SAXS curves of cylindrical, vesicular and spherical nanogels and corresponding model fits (cylinder, vesicle and core-shell sphere models, SasView software).

The present disclosure provides synthetic self-assembling homopolymer for producing nanostructures comprising about 20 repeat units of poly(propylene sulfone) (PPSU$_{20}$). These nanostructures are produced by dissolving PPSU$_{20}$ in DMSO (at 5 mg/ml to about 100 mg/ml, preferably 25 mg/ml to about 50 mg/ml). Water is then mixed at varying ratios (e.g., 2:1 to 10:1 by volume) with the solution of DMSO/PPSU$_{20}$ allowing for the formation of differing nanostructures depending on the ratio and the method of mixing of the water. Ratio of water to DMSO solution include ratio from 2:1 to 10:1, including ranges inbetween (e.g., about 2.5:1, 3:1, 4:1, 5:1, 6:1, 7:1, 7.5:1, 8:1, 9:1, 10:1, etc.). Nanostructures formed include, for example, nanobundles (i.e. bundle-like nanogels) and vesicle-like nanogels (nanovesicles), for example, as depicted in FIG. 2A. The PPSU$_{20}$ nanostructures are able to carry both aqueous (e.g., water soluble) cargo or payloads or hydrophobic cargo or payloads, depending on if the cargo is added to the water or the DMSO solution before mixing. By varying the ratio of water to DMSO:PPSU$_{20}$ solution and the stepwise addition of the water, e.g., adding the water in 1 to 100 increments, preferably 1 to 80 increments, controls the morphology and size of the nanostructures produced as detailed more in the examples. In some embodiments, the water is added in equal amount in 1 to 100 stepwise increments, mixing in between each addition. In other embodiments, the water is added in unequal increments, such as 1-10 increments of smaller amounts and one large amount at the end, or other stepwise increments. The number of increments of water addition in total add up to present a ratio of water to DMSO solution between 2:1 and 10:1. Additionally, the nanostructures produced in the water/DMSO solution can be further dialyzed with water or a physiological solution (e.g., phosphate buffer saline) to remove any residual DMSO from the solution, thus allowing it to be administered to a subject.

Employing dynamic sulfone-sulfone interactions for facile self-assembly of poly(propylene sulfone) homopolymers. Materials that can reversibly adapt to their environment have the potential to revolutionize technologies in diverse fields, ranging from sensors and actuators to applications in biomedicine. The design of such adaptive materials involves reversible chemistries that take advantage of weak and reversible molecular interactions. In the present disclosure, we demonstrate a new type of dynamic noncovalent bond, sulfone-sulfone interactions, that is susceptible to solvent polarity. As far as we are aware, we are the first to fully synthesize poly(propylene sulfone) (PPSU) from complete oxidation of poly(propylene sulfide), which is known for its hydrophobic-hydrophilic transition upon oxidation. However, complete oxidation of PPSU had not been previously achieved, since standard oxidation of PPS generates random copolymers of poly(propylene sulfoxide)-co-poly(propylene sulfone). We found that only the fully converted PPSU networks could undergo physical cross-linking via sulfone-sulfone bonds that can respond dynamically across length scales, allowing formation of both macro- and nanoscale hydrogels from crystalline-coil supramolecular amphiphiles. Following dissolution of PPSU in dimethylsulfoxide (DMSO), the stepwise addition of water provides a simple and highly controllable means of inducing changes in solvent polarity and thus directing dynamic supramolecular self-assembly of PPSU homopolymers. By specifying the hydration history, crystalline frameworks, macroscale hydrogels or uniform nanostructured hydrogels of spherical, vesicular, or cylindrical morphologies can be rapidly fabricated. These hydrogels and nanostructures can be used to encapsulate cargo at a high rate of efficiency and used for drug delivery and targeting.

The present disclosure also provides a system for delivering cargo to a target, e.g., a cell or organ within a subject. The system comprises (a) a nanostructure of $PPSU_{20}$; and (b) a cargo, wherein the nanostructure is loaded with the cargo with a loading efficiency of at least 75%, more preferably at least 80%, still more preferably at least 90%, preferably at least 95%, more preferably at least 98%, and in some instances with a loading efficiency of about 100%. Further, the system provides that the loading capacity of the $PPSU_{20}$ nanostructures is greater than 75%, preferably at least 80%. The systems are able to be loaded with both hydrophobic and hydrophilic (e.g., aqueous) cargo (e.g., a target molecule). The cargo can be added to the water or aqueous solution prior to mixing or can be added to the DMSO solution prior to mixing. It is also envisioned that one or more cargo can be added to both the DMSO solution and the water resulting in the loading of multiple cargoes into the nanostructures. In some embodiment, the system comprises nanostructure of $PPSU_{20}$ is a bundle-like nanostructure. In other embodiments, the system comprises nanostructure of $PPSU_{20}$ which are vesicle-like nanostructure (nanovesicles). In some embodiments, the vesicle-like nanostructure have a diameter of less than 240 nm, preferably less than 180 nm, alternatively a diameter of less than 100 nm, in alternative embodiments, a diameter of less than 50 nm, and comprise nanovesicles with diameters anywhere inbetween (e.g., 240 nm, 230 nm, 220 nm, 210 nm, 200 nm, 175 nm, 150 nm, 125 nm, 120 nm, 110 nm, 100 nm, 90 nm, 80 nm, 70 nm, 60 nm, 50 nm, 40 nm, 30 nm, 20 nm, (i.e., between 250-50 n, between 100-20 nm, between 90-10 nm, between 80-15 nm, between 70-20 nm, and other ranges contemplated therein). The average size is on a weight basis and is measured by light scattering, microscopy, or other appropriate methods.

In methods according to embodiments of the present invention, the methods produce a nanostructure capable of carrying one or more cargo, the method comprising mixing water or a aqueous solution to a solution of $DMSO:PPSU_{20}$ (20 repeat units of poly(propylene sulfone)) at a ratio from about 2:1 to about 10:1 (by volume), preferably about 1:2 to about 1:5 to form a monodisperse nanostructure of $PPSU_{20}$ within the solution. The water:DMSO solution comprising the nanostructures of $PPSU_{20}$ can further undergo dialysis in order to remove the remaining DMSO and produce an aqueous solution (e.g., water or other physiologically suitable solution that can be administered to a subject, e.g., phosphate buffer saline).

The mixing the water to $DMSO:PPSU_{20}$ solution may be performed by methods known in the art, including, for example, vortexing the sample to make a homogeneous solution. In some embodiments, the water is added stepwise in equal or unequal amounts, for example 1 to about 100 steps, wherein the solution is mixed after each addition of the water. In some embodiments, the water or aqueous solution is added stepwise in equal volumes. In some embodiments, the water is an aqueous solution comprising an aqueous cargo (e.g., an aqueous target molecule). In some embodiments, the method comprises adding a water soluble cargo to the water or aqueous solution before being mixed with the solution of $DMSO:PPSU_{20}$.

Suitable solutions of $DMSO:PPSU_{20}$ for use in the methods of the present invention include from about 5 mg/ml to about 100 mg/ml, preferably 25 mg/ml of $PPSU_{20}$. In some embodiments, the solution of $DMSO:PPSU_{20}$ may further comprise a hydrophobic cargo, for example, a hydrophobic target molecule, that one wishes to be loaded into the nanostructures of the present invention.

As used herein, the term "cargo" or "target molecule" are used interchangeably to refer to any molecule to be loaded into the nanostructures according to embodiments of the present invention. The cargo may be hydrophobic, hydrophilic, lipophilic or amphiphilic. Suitable cargo, e.g., target molecules that can be loaded into the nanostructures of the present invention include, but are not limited to, for example, hydrophilic macromolecules (e.g. water-soluble cargo) including, for example, a drug, therapeutic, protein, peptide, DNA, RNA, siRNA, plasmid, antibody, compounds, among others, lipophilic molecules, hydrophobic drug or molecules, and the like. For example, it is envisioned that if the cargo is selected from the group consisting of a DNA molecule, an RNA molecule, and a protein molecule, the water or aqueous solution will have a proper pH and salinity such that the cargo will maintain proper folding and stability while in solution. In some embodiments, the water or aqueous solution will have a physiologically relevant pH and salinity appropriate for loading biological macromolecules into the nanostructures. In one embodiment, the aqueous solution comprises approximately 150 nM salt.

Examples of other cargo that may be added to nanostructures by this process can be selected from, but are not limited to, the known classes of drugs including immunosuppressive agents such as cyclosporins (cyclosporin A), immunoactive agents, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, xanthines, anti-oxidants, preservatives, vitamins, and nutrients. Cargo may also include combinations of, complexes of, mixtures of or other associations of any of the cargo molecules listed.

PPSU networks demonstrated a remarkable ability for molecular encapsulation, achieving >90% encapsulation efficiency for diverse organic solutes that include large hydrophilic molecules like DNA and protein that are typically quite difficult to encapsulate (Table 1). To the best of our knowledge, this work is the first demonstration of dynamic sulfone-sulfone bonding leading to supramolecular self-assembly.

The present disclosure also provides in some embodiments methods of loading a cargo in a nanostructure capable of being delivered to a cell, the method comprising mixing water or an aqueous solution with a solution of DMSO and $PPSU_{20}$ (20 repeat units of poly(propylene sulfone)) at a ratio from about 2:1 to about 10:1 (by volume), preferably about 1:2 to about 1:5, wherein the cargo is present in either the water or aqueous solution or the DMSO solution prior to mixing, and wherein after mixing, a monodisperse nanostructure of $PPSU_{20}$ comprising the cargo is produced.

The loading efficiency of the cargo in the nanostructures by the methods of the present invention is measure as the ratio of the cargo encapsulated within the nanostructure to the total amount of cargo available for loading in the initial solution. The loading efficiency of the monodisperse nanostructure of $PPSU_{20}$ is greater than 75%, preferably greater than 80%, more preferably greater than 90%, even more preferably at least 95%. Further, the loading capacity of the monodisperse nanostructures of $PPSU_{20}$ is greater than 75%, more preferably greater than 80%.

In one example, the method comprises mixing a 1:2 ratio of DMSO solution of $PPSU_{20}$ (25/mg/ml) to water (or aqueous solution), producing nanostructures with vesicle-like nanogels with an average diameter of about 230 nm, preferably with an average diameter of less than 180 nm, preferably with an average diameter of less than 100 nm. In another example, the method comprises mixing a ratio of about 1:5 of DMSO solution of $PPSU_{20}$ (25/mg/ml) to water, producing nanoparticles with an average diameter of less than 170 nm.

Figure 14:
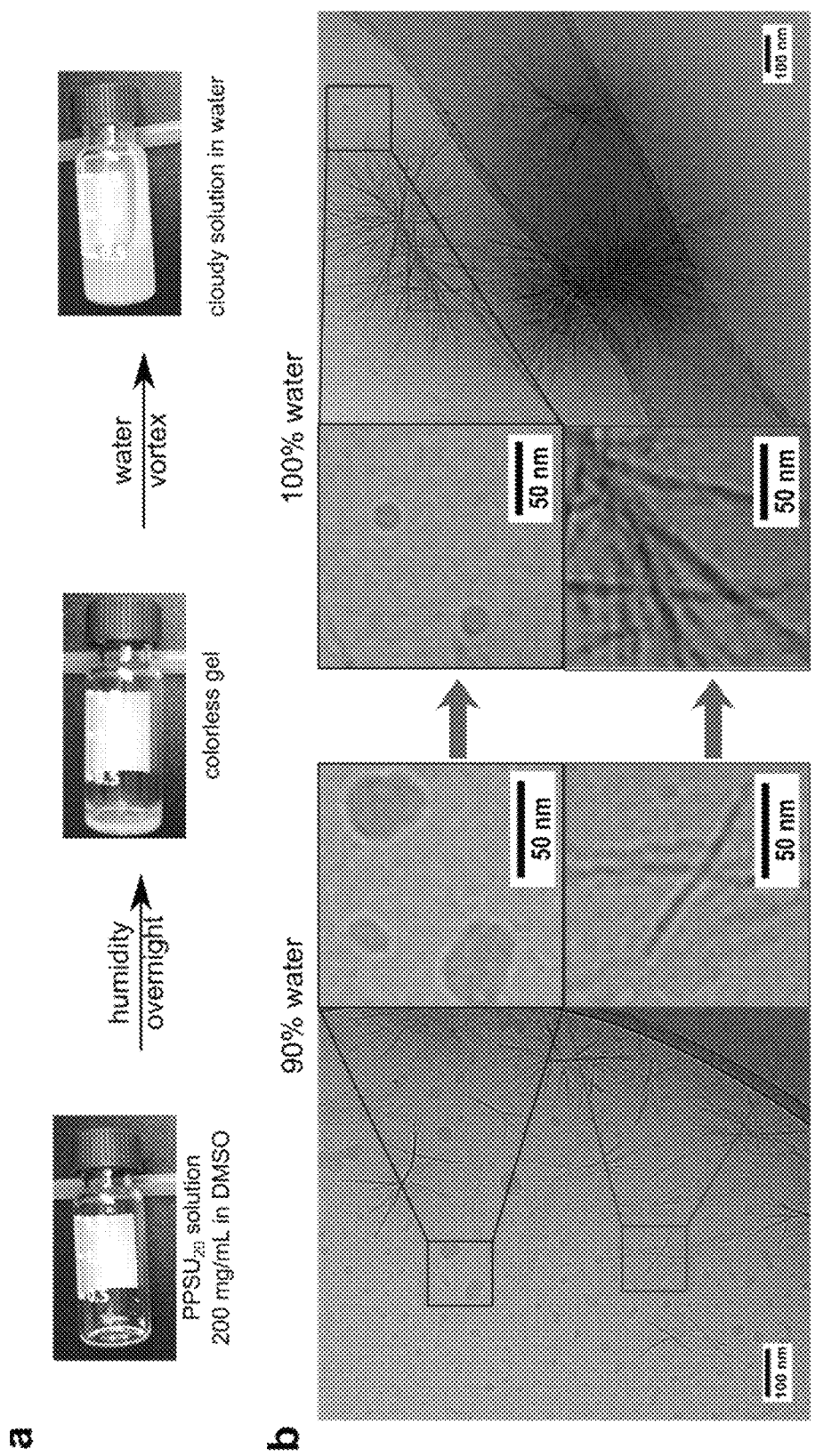
FIG. 14. Quick hydration leading to large scale spatial redistribution of $PPSU_{20}$ chains on network. (a) Exposure and aging of a highly concentrated DMSO solution of $PPSU_{20}$ in air leads to a colorless gel. Thoroughly mixing of the gel with water results in a cloudy solution. (b) Cryo-TEM images of the cloudy solution showing $PPSU_{20}$ nanostructures in a water-DMSO system (1/9, V/V) and in 100% water. Non-uniform aggregates including ribbons formed in 90% water, which reorganized into bundles and vesicular nanogels after dialysis to remove residual DMSO.

Various nanogel structures in aqueous solution can be produced by the methods described herein by dynamically controlling the collapse of ZipNets from DMSO solutions using different ratio of components and different number of stepwise addition of the water to the DMSO solution. For example, as demonstrated in the Example, using the same total volume of water, adjusting only the number of water addition steps, resulting in different nanostructures with different morphologies. For example, a DMSO:$PPSU_{20}$ solution (25 mg/mL PPSU in DMSO) were mixed stepwise with 1:2 ratio (by volume) with water using different number of steps with different step volumes to arrive at the ratio. Each step was followed by overtaxing to thoroughly mix the samples. Dialysis can be used to remove residual DMSO, and representative examples of the representative size and morphology of the nanogels are shown in FIG. 14.

Depending on the number of water additions, the uniform fabrication of nanogels with micellar, vesicular and bundle nanostructures could be specified (FIG. 2B-D), and the obtained physicochemical characteristics are summarized in Table 5.

The nanostructures can be post processed to yield a sterile aqueous or non-aqueous solution or dispersion or could be isolated, such as via lylophilization and autoclaving, to yield a sterile powder for reconstitution into sterile injectable solutions or dispersions. The nanostructures can be combined with other acceptable compounds for parenteral injection such as but not limited to one or more of the following: water, ethanol, propyleneglycol, polyethyleneglycol, glycerol, vegetable oils, and ethyl oleate. Supplemental additives suitable for parenteral injection can also be used to tailor the composition to that suitable for a specific purpose.

In one embodiment, the nanostructure compositions produced by the methods of the present invention are formulated into a solid dosage form for oral administration such as capsules, tablets, pills, powders, and granules, or the like. In such solid dosage forms, the composition is admixed with one or more supplemental additives falling into the following classes such as, but not limited to, lubricants, buffering agents, wetting agents, adsorption, inert excipients, binders, disintegrating agents, solution retarders, accelerators, adsorbents, or fillers or extenders or other components commonly used by those skilled in the art for production of solid dosage forms.

In an embodiment, a composition comprising nanostructures of the present invention is a potent pharmaceutical containing one or more target molecules produced by methods of the present invention. In some embodiments, the composition is a solid dosage form and due to its nanoparticulate size it is evenly dispersed throughout said solid dosage form admixture and yields a high content uniformity (quantity of material in each dose) not obtained if the drug was microparticulate.

In one embodiment, the nanostructure compositions produced by the methods of the present invention are formulated into a pharmaceutically acceptable liquid dosage form for oral administration such as a syrup, solution, emulsion, suspension, or elixir. The liquid dosage forms may further comprise inert diluents, solubilizing agents, oils, emulsifiers, adjuvants suspending agents, sweeteners, wetting agents, flavoring agents, perfuming agents or other compounds commonly used by those skilled in the art. In another embodiment, the nanostructure compositions may be a dry capsule state for oral delivery. The particles are crystalline in solution and more so when dried and thus retain their payloads after desiccation for facile rehydration at a later time. In some examples, the nanostructure compositions may be a pill capsule containing the dried particles for oral administration.

In one embodiment, the nanostructure compositions produced by the methods of the present invention are formulated into a pharmaceutically acceptable liquid dosage form for intravenous administration such that it is a biologically compatible aqueous solution at relevant salt concentration, composition, pH, and temperature. The liquid dosage forms may further comprise inert diluents, solubilizing agents, oils, emulsifiers, adjuvants suspending agents, wetting agents or other compounds commonly used by those skilled in the art.

The nanostructure $PPSU_{20}$ compositions with or without one or more target molecules produced by the methods of the present invention can be administered to a subject, for example, humans and animals, via a number of means including, but not limited to, orally, rectally, parenterally (intravenous, intramuscular, or subcutaneous), intracisternally, intravaginally, intraperitoneally, locally (in the form of powders, ointments or drops) or as a buccal or nasal spray. In one embodiment, the nanostructure compositions are administered orally. In one embodiment, the nanostructure compositions are administered intravenously.

The $PPSU_{20}$ nanostructures produced by the methods of the present invention can also be used in immunotherapy, immunotheranostic or theranostic application which combine immunotherapy and diagnostics. It is envisioned that target molecules used for immunotherapy can be incorporated along with target molecules used for imagine and diagnostics into a single nanostructure or a composition comprising nanostructures for theranostic treatments.

The use herein of the terms "including," "comprising," or "having," and variations thereof, is meant to encompass the elements listed thereafter and equivalents thereof as well as additional elements. Embodiments recited as "including," "comprising" or "having" certain elements are also contemplated as "consisting essentially of" and "consisting of" those certain elements.

As used herein, "about" means within 5-10% of a stated concentration range or within 5-10% of a stated number.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of."

The present invention has been described in terms of one or more preferred embodiments, and it should be appreciated that many equivalents, alternatives, variations, and modifications, aside from those expressly stated, are possible and within the scope of the invention.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Introduction

Self-assembly is ubiquitous in biological systems and underlies the formation of complex structures from simple components. Compared to the capabilities of natural polymers, such as polypeptides (1) and DNA (2), for dynamic assembly and reorganization via noncovalent interactions, synthetic polymer-based systems are relatively primitive (3). Such controlled aqueous self-assembly of single component supramolecular systems has remained a challenge for synthetic polymers, which typically require amphiphilicity or direct incorporation of naturally occurring peptide/nucleic acid monomers or derivatives thereof for controlled aggregation in aqueous systems. The most common synthetic self-assembling systems employ amphiphilic copolymers that are limited to separate hydrophobic and hydrophilic segments, which do not allow the complex dynamic self-assembly behavior observed in nature while also maintaining aggregate stability required for a broad range of applications. In terms of nanofabrication in aqueous solution, focus has been placed on the design of amphiphilic block (4) or random (5) copolymers wherein adjustment of the volume fraction of the hydrophobic/hydrophilic components permits fabrication of various nanostructures including spheres, cylinders, and vesicles. The multicomponent nature and dauntingly wide range of chemical compositions that have been developed for these self-assembling systems can present difficulties during chemical synthesis (6) and practical application (7), often requiring expertise in synthetic polymer chemistry and delaying translation of useful technologies.

Noncovalent weak/reversible interactions such as π-π stacking (8), hydrogen bonding (9, 10) and certain metal-ligand coordination bonds (11) provide strategies for construction of structurally dynamic architectures. Here, we report on a single-component homopolymer system that assembles through dynamic noncovalent sulfone-sulfone bonding. Crystalline frameworks and nanoscale hydrogels of spherical, vesicular, and cylindrical morphology were controllably assembled from solely a poly(propylene sulfone) (PPSU) homopolymer when transitioning from dimethylsulfoxide (DMSO) solution to aqueous system. Semi-flexible PPSU chains formed electrostatically bound networks that reorganize dynamically as interactions among sulfone repeat units increased. This system mimics the dynamic self-assembly of proteins (12) and DNA (13), allowing the design and fabrication of diverse superstructures with an unprecedented capability for molecular encapsulation.

Results

Figure 5:
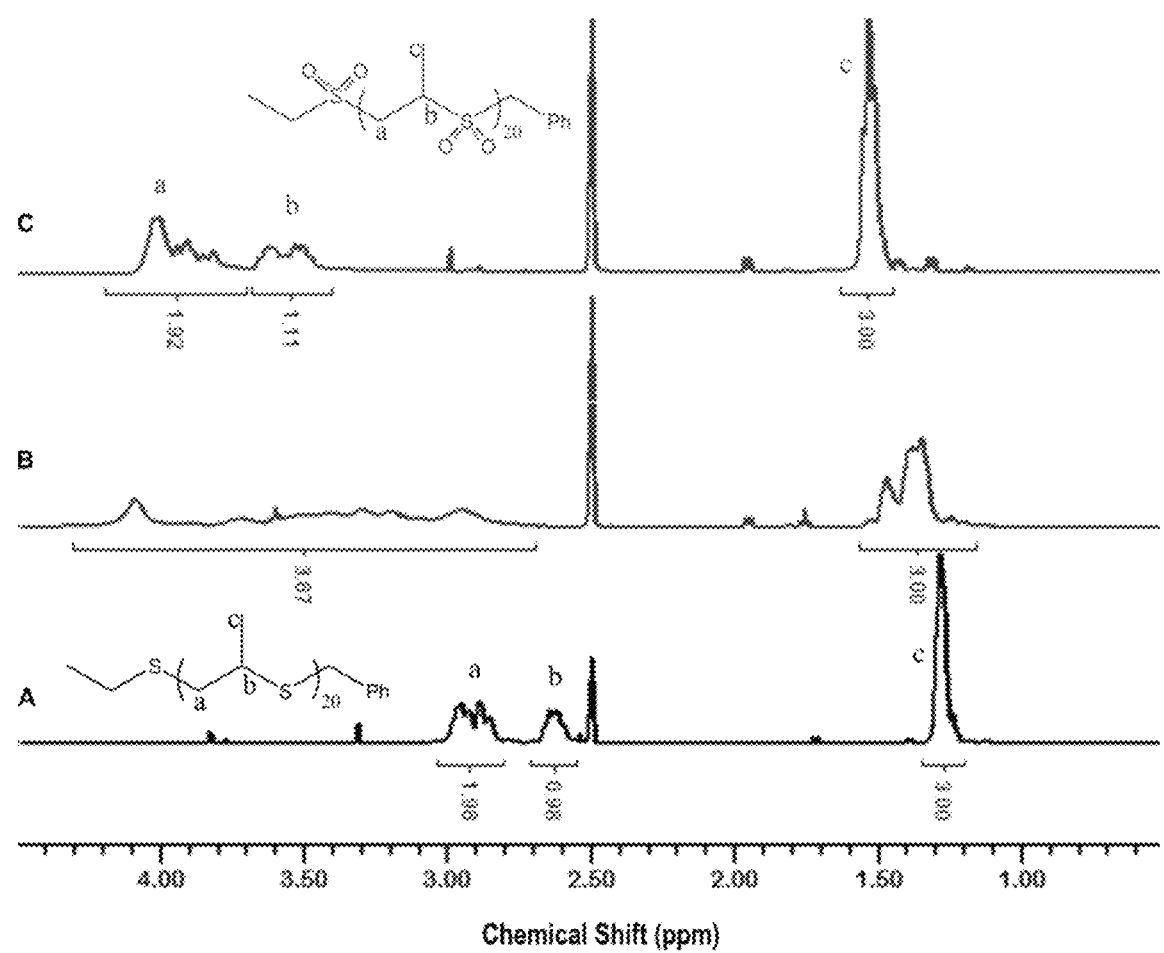
FIG. 5. $^1$H NMR spectra of (A) PPS$_{20}$, (B) incompletely oxidized product of PPS$_{20}$ (random copolymers of sulfoxides and sulfones), and (C) PPSU$_{20}$ in DMSO-d$_6$.
Figure 6:
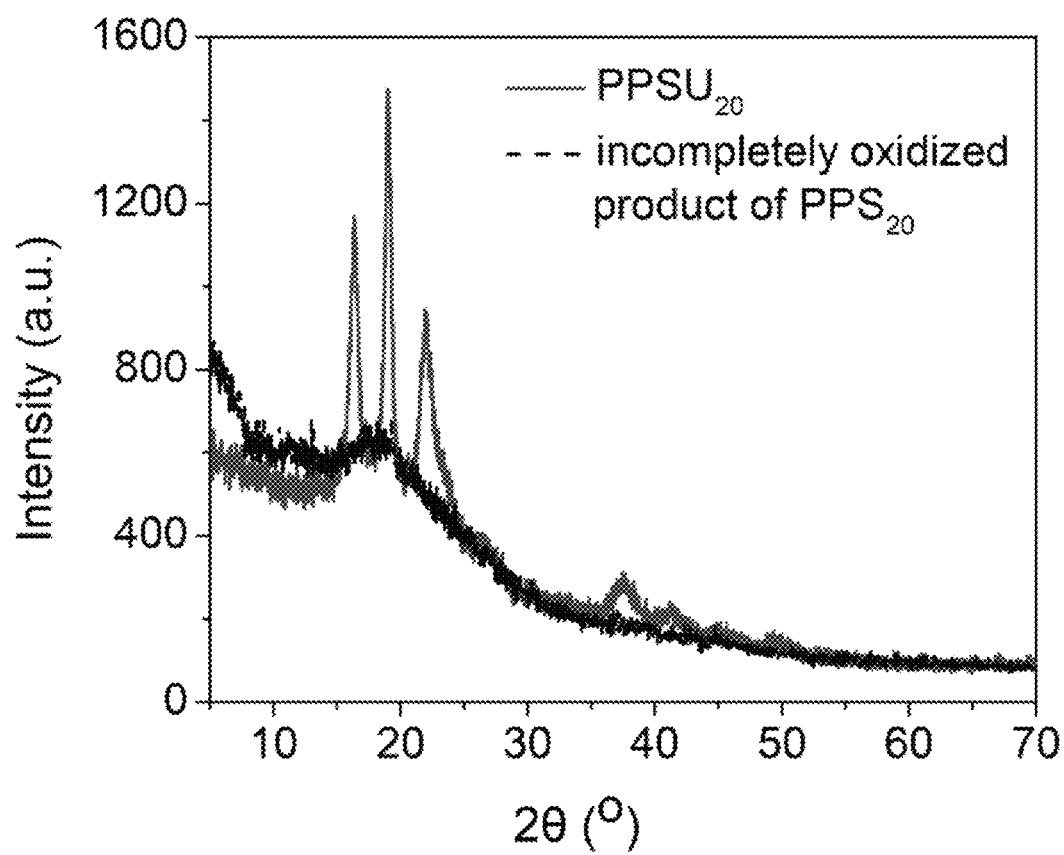
FIG. 6. WAXD patterns for PPSU$_{20}$ powders and incompletely oxidized product of PPS$_{20}$ (sulfoxide/sulfone mixtures).

PPSU can be synthesized from complete oxidation of poly(propylene sulfide) (PPS) (14, 15), which is known for its hydrophobic-hydrophilic transition upon oxidation (16-18). However, complete oxidation of PPS had not been previously achieved, since standard oxidation of PPS generates random copolymers of poly(propylene sulfoxide)-co-poly(propylene sulfone) (19). We successfully synthesized $PPSU_{20}$ (20 sulfones, FIG. 5) using an atypically high concentration of $H_2O_2$. Highly concentrated $H_2O_2$ was generated in situ upon vacuum evaporation during the oxidizing reaction. The resulting $PPSU_{20}$ is a crystalline solid (FIG. 6), and solubility tests in water and common organic solvents (Table 2) revealed that only dimethylsulfoxide (DMSO) can effectively break $PPSU_{20}$ crystals into a clear solution. By following the phase transition for a DMSO solution of $PPSU_{20}$ during vacuum evaporation, we found that the system remained homogeneous until drying, suggesting an ultra-high solubility of $PPSU_{20}$ in anhydrous DMSO. Given that the chemical structure of PPSU (FIG. 1a) is characterized by a positively charged backbone with negatively charged pendent oxygen atoms (20), electrostatic repulsion among oxygen atoms (21) was expected to result in weak inter- and intra-chain associations.

Figure 1:
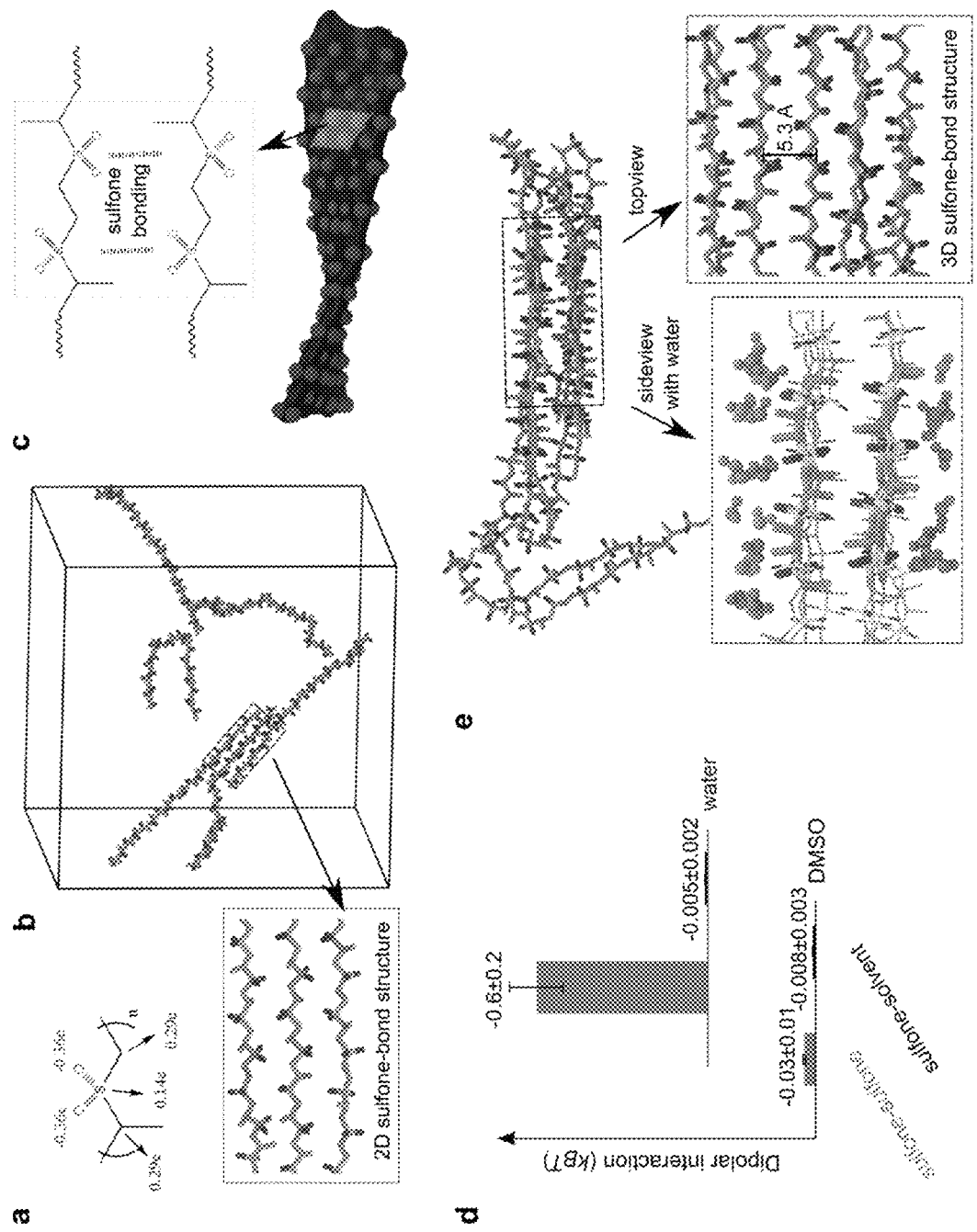
FIG. 1. Structural features of PPSU. (a) Chemical structure of PPSU showing the polymer backbone and oxygen atoms that carry positive/negative (blue/red) atomic partial charges, respectively. (b) Atomistic simulation snapshot showing a dissolution-complementarity equilibrium in DMSO for six PPSU$_{20}$ chains. Inset is a superstructure formed by PPSU self-complementarity. (c) PPSU self-complementarity leading to a 2D reversible superstructure with enrichment of oxygen atoms on the surface. Formation of 3D superstructures is inhibited in DMSO due to the strong repulsion among layers. (d) Average dipolar energies per dipole-dipole pair of sulfone-sulfone and sulfone-solvent. Error bars represent the standard deviation from three parallel simulations. (e) Atomistic simulation snapshot showing the formation of a 3D superstructure through PPSU bundling in water. Inset showing the 3D superstructure with or without water molecules.
Figure 7:
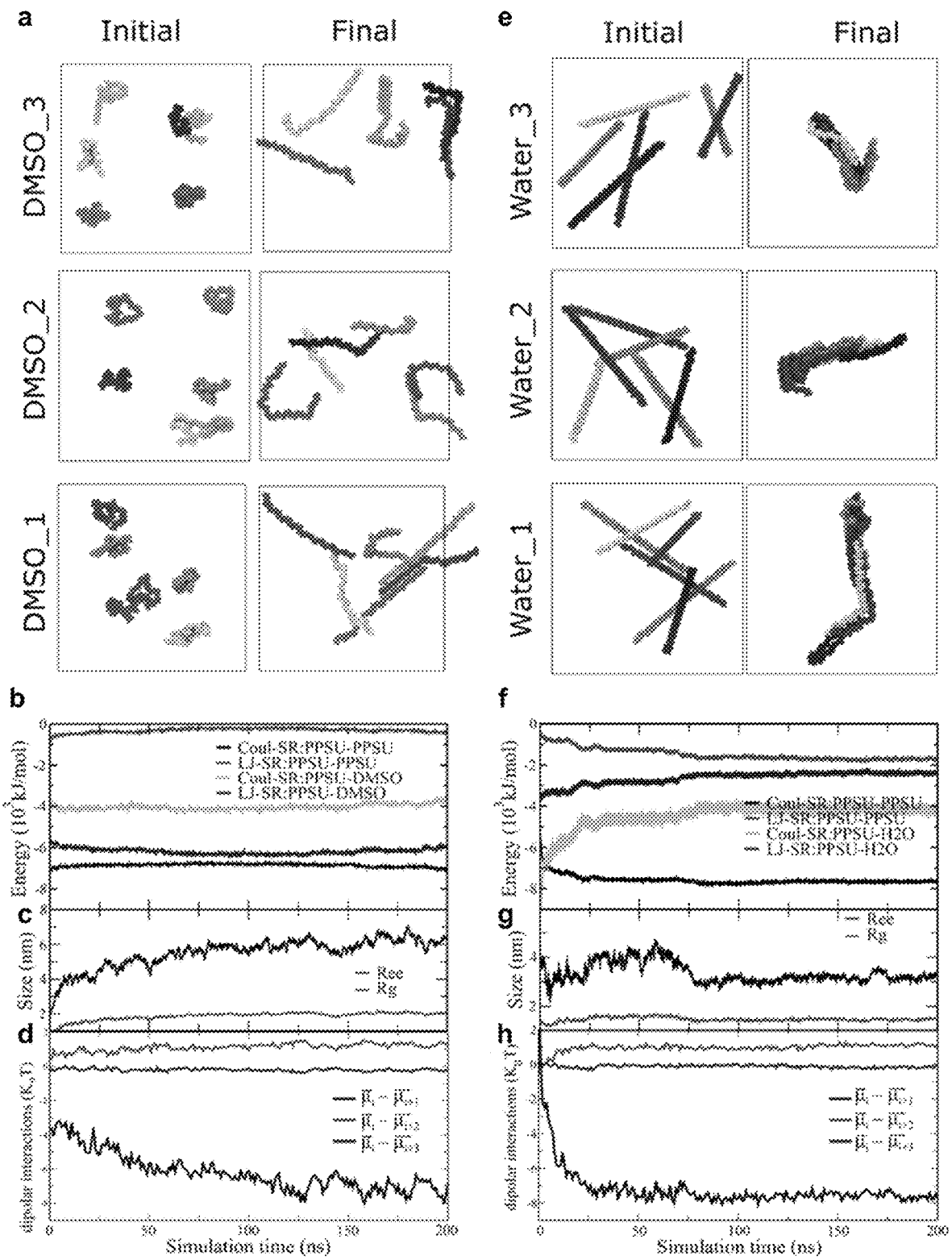
FIG. 7. Atomistic simulation snapshots and convergence of PPSU$_{20}$ (6 chains, 12.5 mg/mL) in (a-d) DMSO and (e-h) water solvents. (a) The initially coiled PPSU$_{20}$ chains turned into extended conformation in DMSO solutions, whereas (b) the initially extended PPSU$_{20}$ chains collapsed and aggregated in water systems. Three parallel simulations were performed for both solvents. Hydrogen atoms on PPSU$_{20}$ and solvent molecules are omitted for clarity. The six PPSU$_{20}$ chains are colored differently. The blue solid line denotes the simulation box. (b, f) The short-range Coulombic (Coul-SR) and LJ (LJ-SR) interactions between PPSU$_{20}$ chains and between PPSU$_{20}$ and solvents (DMSO or water), which were calculated up to a cutoff distance of 1.2 nm. (c, g) The sizes of the PPSU$_{20}$ chains described via the end-to-end distance (R$_{ee}$) and the radius of gyration (R$_g$), which were calculated using the sulfur atoms on PPSU$_{20}$. (d, h) The dipolar interactions between PPSU monomers which are covalently connected ($\vec{\mu}_t$–$\vec{\mu}_{t+1}$), or neighbors of $\vec{\mu}_t$–$\vec{\mu}_{t+2}$, or $\vec{\mu}_t$–$\vec{\mu}_{t+3}$. All the calculations supported that the simulations were roughly converged after around 100 ns in both DMSO and water solvents.
Figure 8:
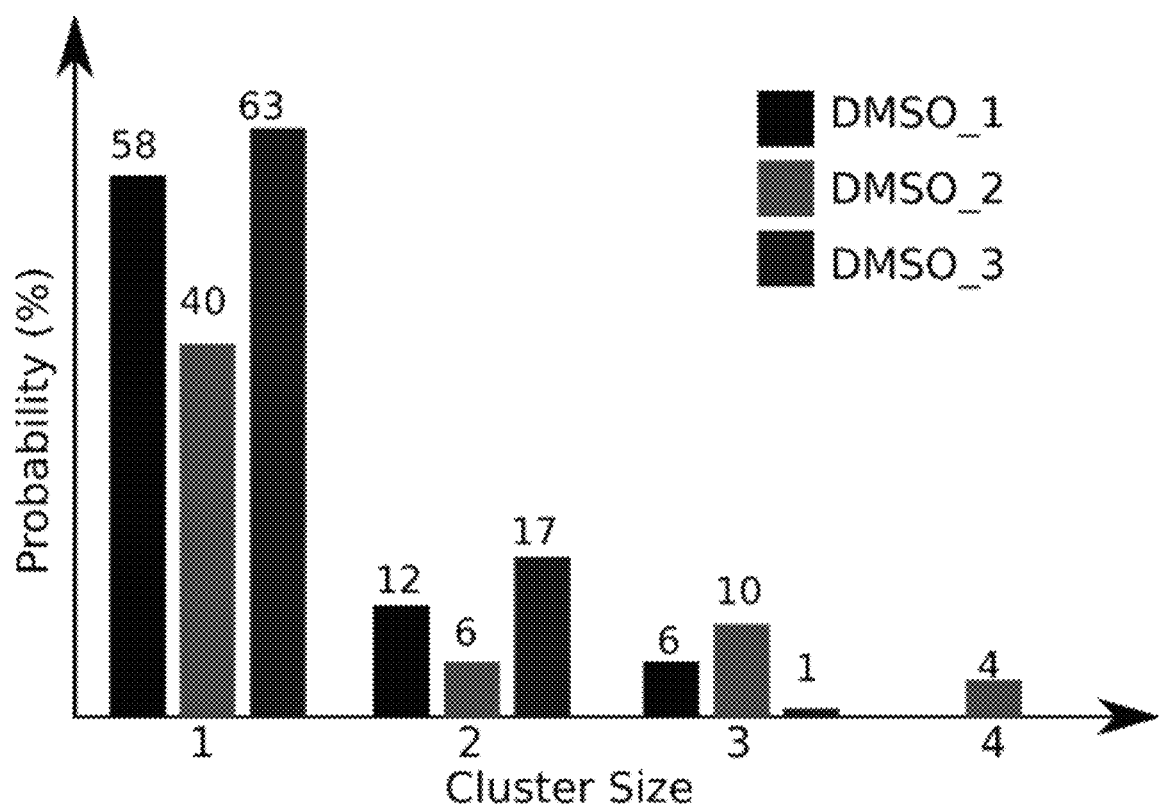
FIG. 8. Distribution of PPSU$_{20}$ clusters in the three parallel all-atom simulations in DMSO. PPSU$_{20}$ chains are viewed as clusters if the distance of any inter-chain sulfur atoms is less than 0.67 nm (the first minimum in the radial distribution function in FIG. 12). A maximum probability occurs at the cluster size of 1 supports that the PPSU chains are dispersed in DMSO solvent (S1). The GROMACS program gmx clustersize was employed for the calculations.
Figure 9:
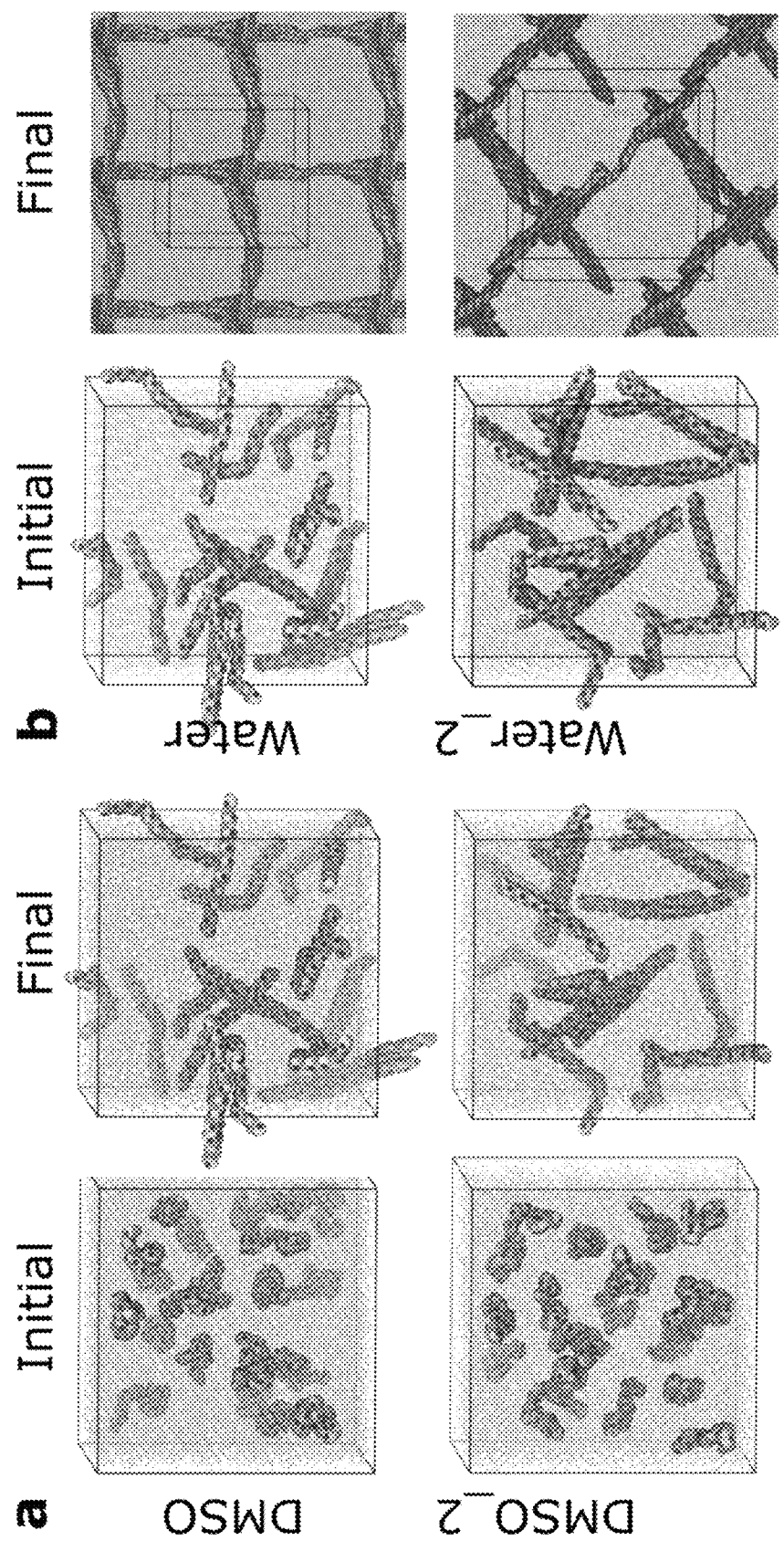
FIG. 9. Atomistic simulation snapshots of PPSU$_{20}$ (22 chains, 25 mg/mL) in DMSO and water. (a) The initially coiled PPSU$_{20}$ chains turned into extended conformation in DMSO. (b) Under the application of solvent replacement from DMSO to water, network structure of PPSU$_{20}$ formed due to inter-chain associations. Two parallel simulations were performed for both systems.
Figure 10:
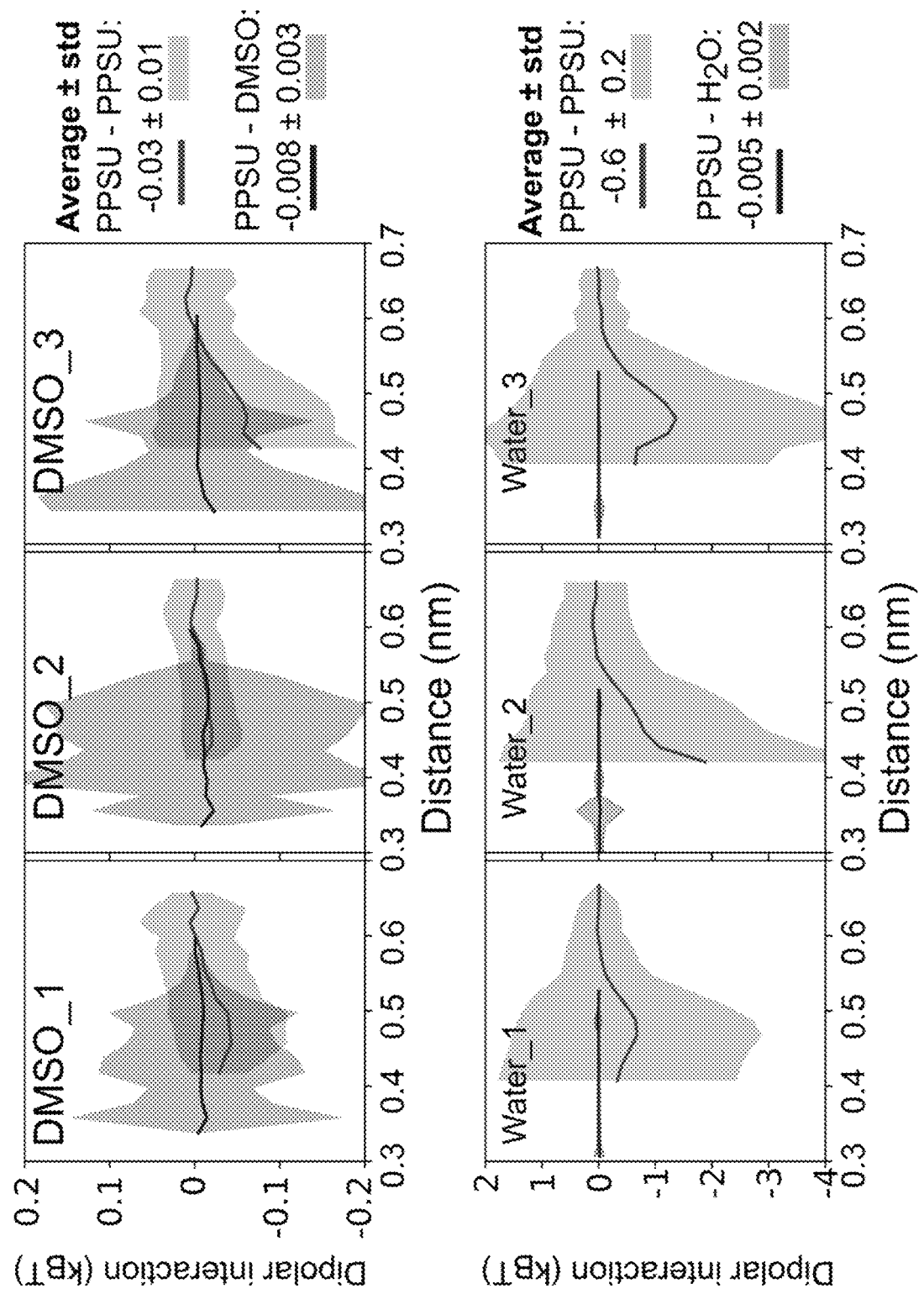
FIG. 10. Dipolar energy per dipole-dipole pair of PPSU-PPSU and PPSU-solvent (DMSO/water). The solid lines stand for the average value as a function of the distance, which is based on the sulfur atoms of PPSU and DMSO, and the oxygen atoms of water. The shadow regions describe the standard deviation of corresponding dipolar energies. Listed in the inset on the right are the average dipolar energies and the standard deviations, which are calculated from the three parallel simulations for the whole distance range. Note that for the S(PPSU)-S(PPSU) calculations all the intramolecular interactions within 5 consecutive repeating units were excluded based on the calculated persistence of 4.4 repeating units in water (Table 4).

We anticipated that the weak intra-chain associations of PPSU in DMSO would be accompanied by high chain stiffness. In order to establish that the structural features of PPSU can give rise to chain expansion and solubilization, we carried out all-atom explicit sD) simulations for $PPSU_{20}$ in DMSO (simulation parameters are given in Table 3 and snapshots of initial and final conformations are shown in FIG. 7). A typical snapshot is depicted in FIG. 1b, showing that the initially coiled chains turned into roughly extended conformations. The calculated persistence length ($L_p$, Table 4) confirmed that the polymer is a semi-flexible chain in DMSO with an average $L_p$ of 9.2±0.7 sulfones. The simulations also suggest that inter-chain associations are not completely inhibited in DMSO as indicated by the sulfone-sulfone complementary. Complementarity-driven bundling of $PPSU_{20}$ chains would lead to a distorted two-dimensional (2D) structure with enrichment of oxygen atoms on the surface (FIG. 1c) due to the zigzag trans-planar arrangement of sulfones between two parallel but slight twisted chains. We therefore inferred that the inter-chain associations is reversible in DMSO. This self-limited growth is confirmed by both a cluster formation analysis (FIG. 8) and the DMSO simulations of more $PPSU_{20}$ chains at a higher concentration (FIG. 9). Furthermore, we demonstrated negligible dipolar attractive interactions (FIG. 10) for the sulfone-sulfone pairs (FIG. 1d), which are approximately comparable to those of sulfone-DMSO, supporting the ultra-high solubility of $PPSU_{20}$ in DMSO.

TABLE 3

Some Data in the All-atom MD Simulations

| Entry[a] | Number of $PPSU_{20}$ chains | Number of solvent molecules | Length of box (nm)[b] | Simulation time (ns)[c] |
|---|---|---|---|---|
| DMSO_1 | 6 | 13893 | 11.867 ± 0.004 | 150 + 50 |
| DMSO_2 | 6 | 13896 | 11.868 ± 0.004 | 150 + 50 |
| DMSO_3 | 6 | 13894 | 11.868 ± 0.004 | 150 + 50 |
| Water_1 | 6 | 56887 | 11.924 ± 0.006 | 150 + 50 |
| Water_2 | 6 | 56885 | 11.924 ± 0.004 | 150 + 50 |
| Water_3 | 6 | 56877 | 11.923 ± 0.005 | 150 + 50 |

[a]Three parallel simulations for both DMSO and water solvents.
[b]The simulation box length in the production simulations of 50 ns.
[c]Time in the equilibration simulation + time in production simulation.

TABLE 2

Solubility of $PPSU_{20}$ in water and some common organic solvents.

| | solvent[a] | | | | | | | | | |
|---|---|---|---|---|---|---|---|---|---|---|
| | water | MeOH | AA | CAN | NMP | DMSO | DMF | DCM | Py | THF | Diox |
| | | | | | polarity[b] | | | | | | |
| | 1.000 | 0.762 | 0.648 | 0.460 | 0.458 | 0.444 | 0.386 | 0.309 | 0.302 | 0.207 | 0.164 |
| crystal[c] | X | X | X | X | ✓[f] | ✓[g] | X | X | X | X | X |
| solution[d] | C | C | C | C[e] | M | M | M | M | M | M | M |

[a] MeOH = methanol, AA = acetic acid, CAN = acetonitrile, NMP = 1-methyl-2-pyrrolidinone, DMSO = dimethylsulfoxide, DMF = dimethylformamide, Py = pyridine, THF = tetrahydrofuran, Diox = dioxane.
[b] Relative polarity (S2).
[c] Using $PPSU_{20}$ crystals for the solubility tests. X = insoluble, ✓ = soluble.
[d] Mixing a DMSO solution of $PPSU_{20}$ (25 mg/mL) with 9 times the volume of other solvents, then checking the turbidity of the mixtures. C = cloudy. M = miscible.
[e] The mixture was clear at the beginning, but became cloudy in 1 hour.
[f] Solubility of $PPSU_{20}$ in 1 mL of NMP is ~23 mg.
[g] Solubility of $PPSU_{20}$ in 1 mL of DMSO is >250 mg.

TABLE 4

| | Results from All-atom MD Simulations [a] | | | | | | | |
|---|---|---|---|---|---|---|---|---|
| | DMSO | | | | water | | | |
| | Run 1 | Run 2 | Run 3 | Average | Run 1 | Run 2 | Run 3 | Average |
| $R_{ee}$ [b] | 6.2 | 6.1 | 5.6 | 6.0 ± 0.3 | 4.6 | 3.2 | 2.4 | 3.4 ± 1.0 |
| $L_p$ [c] | 9.8 | 9.6 | 8.2 | 9.2 ± 0.7 | 4.6 | 4.2 | 4.3 | 4.4 ± 0.2 |

[a] All calculations are based on the sulfur atoms on PPSU$_{20}$. The GROMACS program gmx polystat was employed.
[b] End-to-end distance, in the unit of nm. $R_{ee}$ = 7.9 nm for a fully extended PPSU$_{20}$ chain.
[c] Persistence length, in the unit of repeat units.

Figure 11:
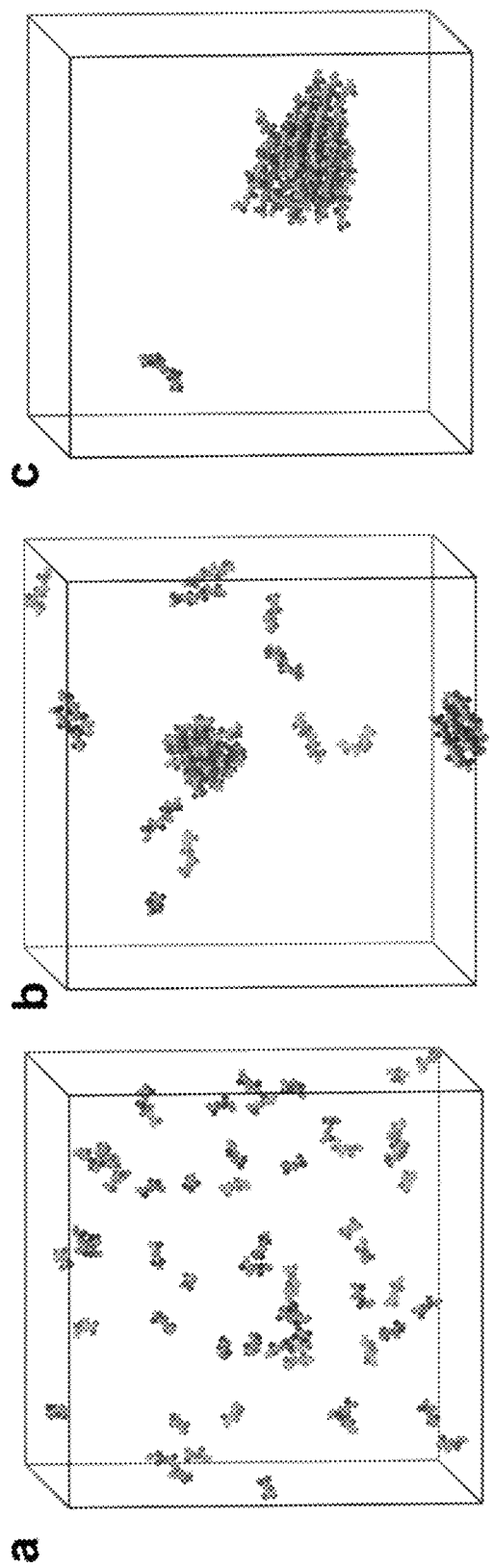
FIG. 11. Final atomistic simulation snapshots of propylene sulfone oligomers in water. Intermolecular associations increase as degree of polymerization increase from dimers (a) to tetramers (b) and hexamers (c).

We further investigated the solubility of PPSU$_{20}$ by mixing its DMSO solution with an excess amount of other solvents (Table 2). Interestingly, aggregates were visible in highly polar solvents including water and aprotic acetonitrile. In contrast, solvents with lower polarity than DMSO did not induce aggregation. These observations indicate that the highly polar PPSU polymer is not soluble in water as widely predicted (14). Characterized by a high dipole moment (22) and partially charged groups, the sulfones show a formal similarity to zwitterions, and it seemed possible that PPSU, like zwitterionic polymers (23), may have the ability to form physically cross-linked networks. Although formation of such sulfone-sulfone bonded networks would be inhibited by electrostatic repulsion among oxygen atoms, we anticipated PPSU to overcome this limitation when exposed to highly polar mediums such as water. AAMD simulations of PPSU$_{20}$ in water provided insight into the mechanism and kinetics of aggregate formation. We observed in the simulations that the initially extended PPSU$_{20}$ chains collapsed within 1 ns of the simulations, followed by chain folding and association into three-dimensional (3D) superstructures (FIG. 1e). A significant decrease in both Lp and end-to-end distance for PPSU$_{20}$ chains was discovered in water versus in DMSO (Table 4). This conformational transition is consistent with the aggregates expected to form upon hydration of PPSU$_{20}$ chains under conditions of weak electrostatic repulsion. Water molecules generally aid supramolecular assembly by means of hydrogen bonds (24). However, the PPSU$_{20}$/water AAMD simulations revealed hydrogen bonds to not be a significant driver of aggregation, as water occurred exclusively at the surfaces of the 3D superstructures. Instead of water bridges, only dislocation of oxygen atoms on PPSU between layers were visible in the 3D superstructures. Neighboring water molecules were predicted to be located on surfaces but not inside of PPSU aggregates (FIG. 1e). The 3D superstructures are stabilized by strong dipolar attractive interactions (FIG. 1d), suggesting an electrostatic nature of the sulfone-sulfone bonding. It is worthwhile to note that a single sulfone bond is not strong enough to create stable aggregates in aqueous solution, as indicated by the good water-solubility observed for both dimethylsulfone and random copolymers of poly(propylene sulfoxide)-co-poly(propylene sulfone). AAMD simulations of oligo(propylene sulfone) in water further confirm that aggregates are formed when the degree of polymerization is bigger than 6 (FIG. 11). Thus, we concluded that PPSU promotes the formation of sulfone-bond networks due to intra- and/or inter-chain associations.

Figure 12:
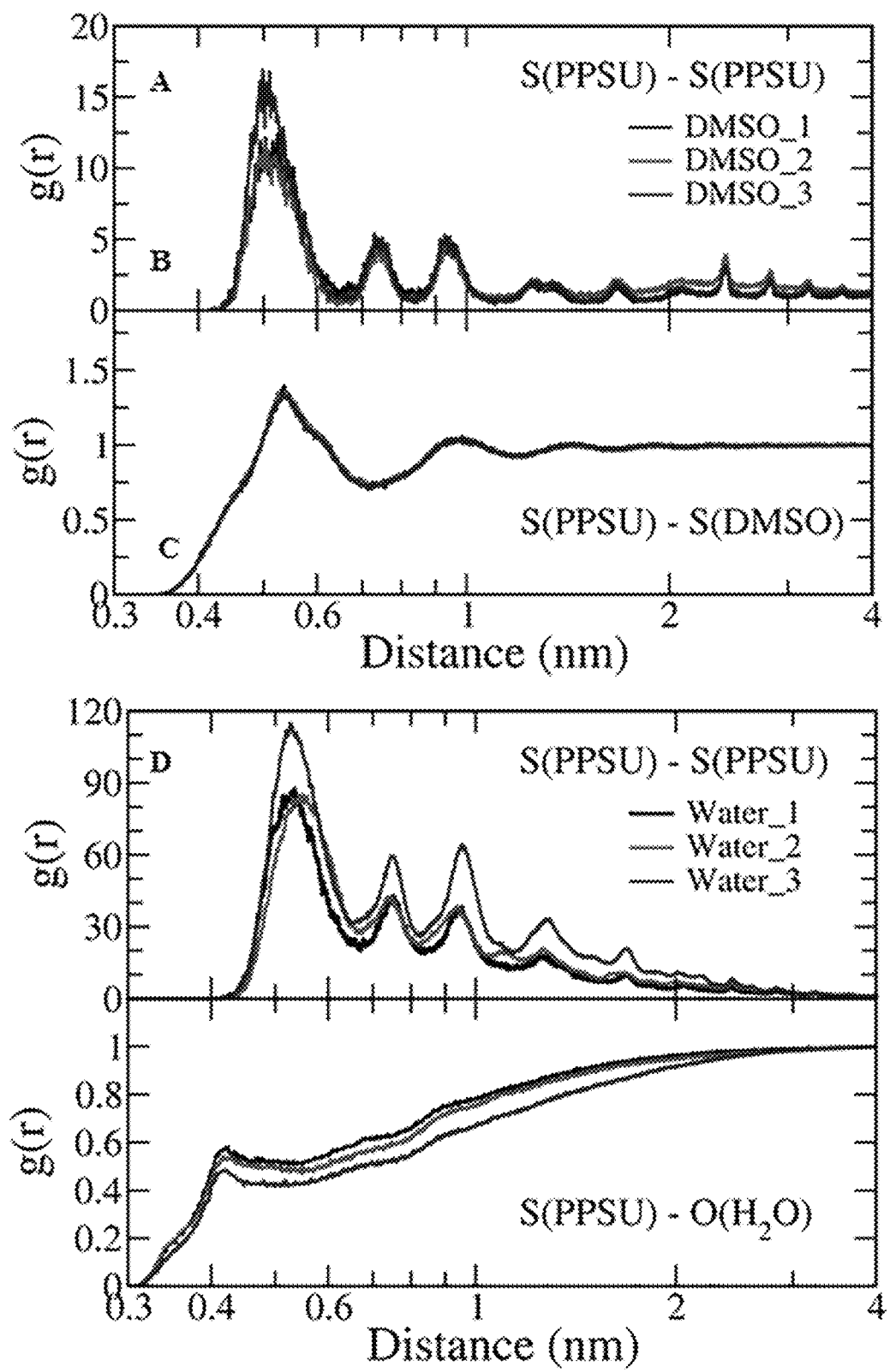
FIG. 12. Radial distribution functions (RDFs, g(r)) in the (A, B) DMSO and (C, D) aqueous systems. Results are obtained from three parallel all-atom simulations. In the calculations, all the intra-molecular S(PPSU)-S(PPSU) correlations within 5 repeat units were excluded based on persistence length of 4.4 monomers in water (Table 4). The RDFs between the sulfur atoms on $PPSU_{20}$ in the aqueous solutions supporting a crystalline structure for $PPSU_{20}$.
Figure 13:
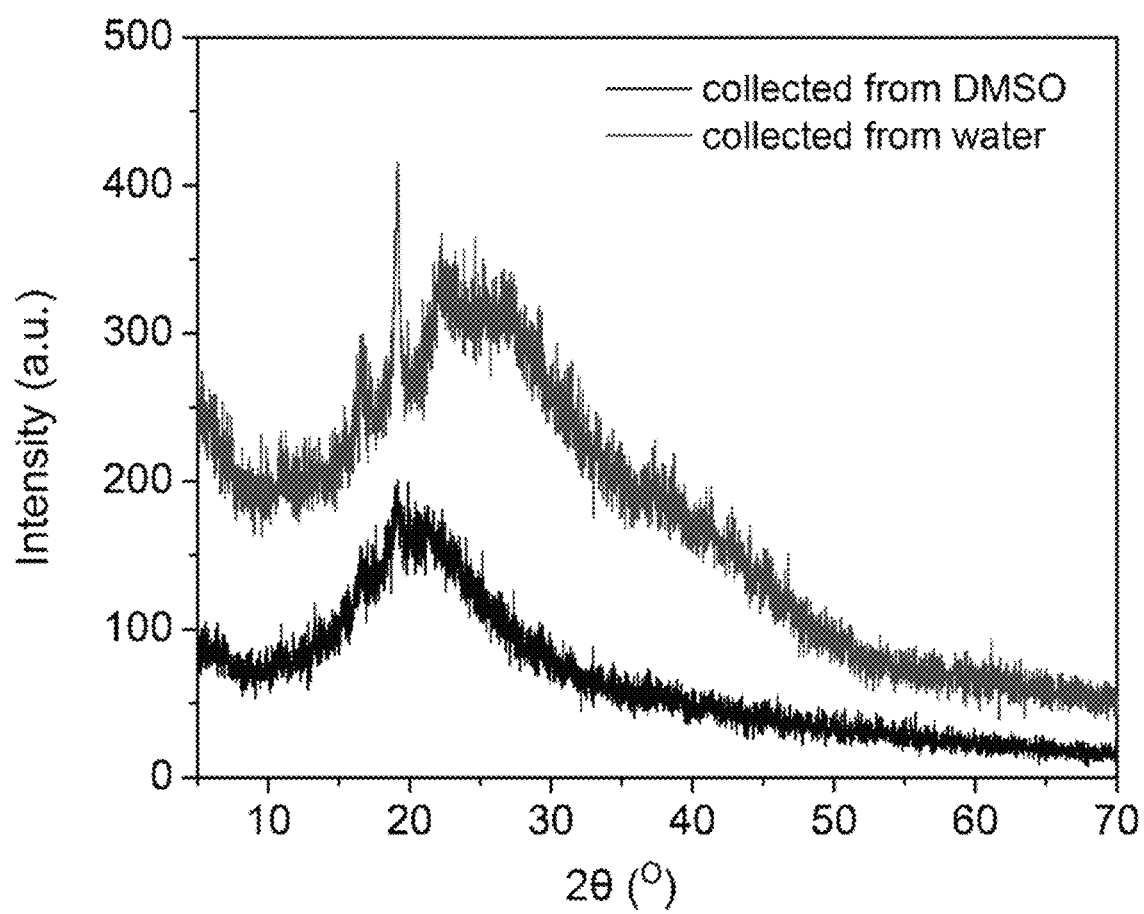
FIG. 13. WAXD patterns for $PPSU_{20}$ precipitates collected from DMSO or water. The fluffy precipitates were obtained by exposing 200 μL of DMSO solution of $PPSU_{20}$ (25 mg/mL) to humidity in air for 110 days. After centrifugation, part of the precipitates was applied for WAXD directly, and the other precipitates was dispersed in water and recollected for WAXD.

Because the AAMD simulations predicted that PPSU$_{20}$ can form crystalline superstructures in water (FIG. 12), we considered whether the crystallization involved dynamic rearrangement of the sulfone-sulfone bonded network. From a kinetic point of view, network formation is preferential to crystallization given the nearly equal opportunity of all sulfones on PPSU$_{20}$ chains to form sulfone-sulfone bonds. Furthermore, the sulfone-sulfone complementarity in DMSO simulations implies that PPSU$_{20}$ tends to form sulfone-sulfone bonded networks. The gelling tendency of PPSU was experimentally confirmed by exposing DMSO solutions of PPSU$_{20}$ to humidity, which led to a sol-to-gel phase transition or precipitation respectively for high (e.g. 200 mg/mL) and low (e.g. 25 mg/mL) concentration aged PPSU$_{20}$ solutions. The resulting colorless gel or fluffy precipitates were analyzed by wide-angle X-ray diffraction (WAXD) and found to be mostly amorphous (FIG. 13). Given the possibility that the gels in DMSO-water systems were generally under equilibrium of electrostatic repulsions and attractions, we exploited the reorganization capability for the colorless gel under the application of further hydration. By thoroughly mixing the gel with an excess amount of water, we obtained a cloudy solution in which non-uniform hydrogels of ribbon, cylindrical and spherical morphologies were found by cryogenic transmission electron microscopy (Cryo-TEM) (FIG. 14). This drastic shape transformation from a macroscopic bulk gel to nanostructured hydrogels requires large scale spatial redistribution of PPSU chains, which involves breaking and reforming of sulfone-sulfone bonds into tightly cross-linked structures. In the process of dialysis to remove residual DMSO, we observed a further shape transformation of the nanoscale hydrogels into smaller spherical, vesicular and cylindrical morphologies (FIG. 14). This system mimics the fibrous hydrogels created by peptide-DNA conjugates and peptides (25), providing us with a 'top-down' approach for the fabrication of various nanostructured hydrogels through network rearrangement.

Figure 15:
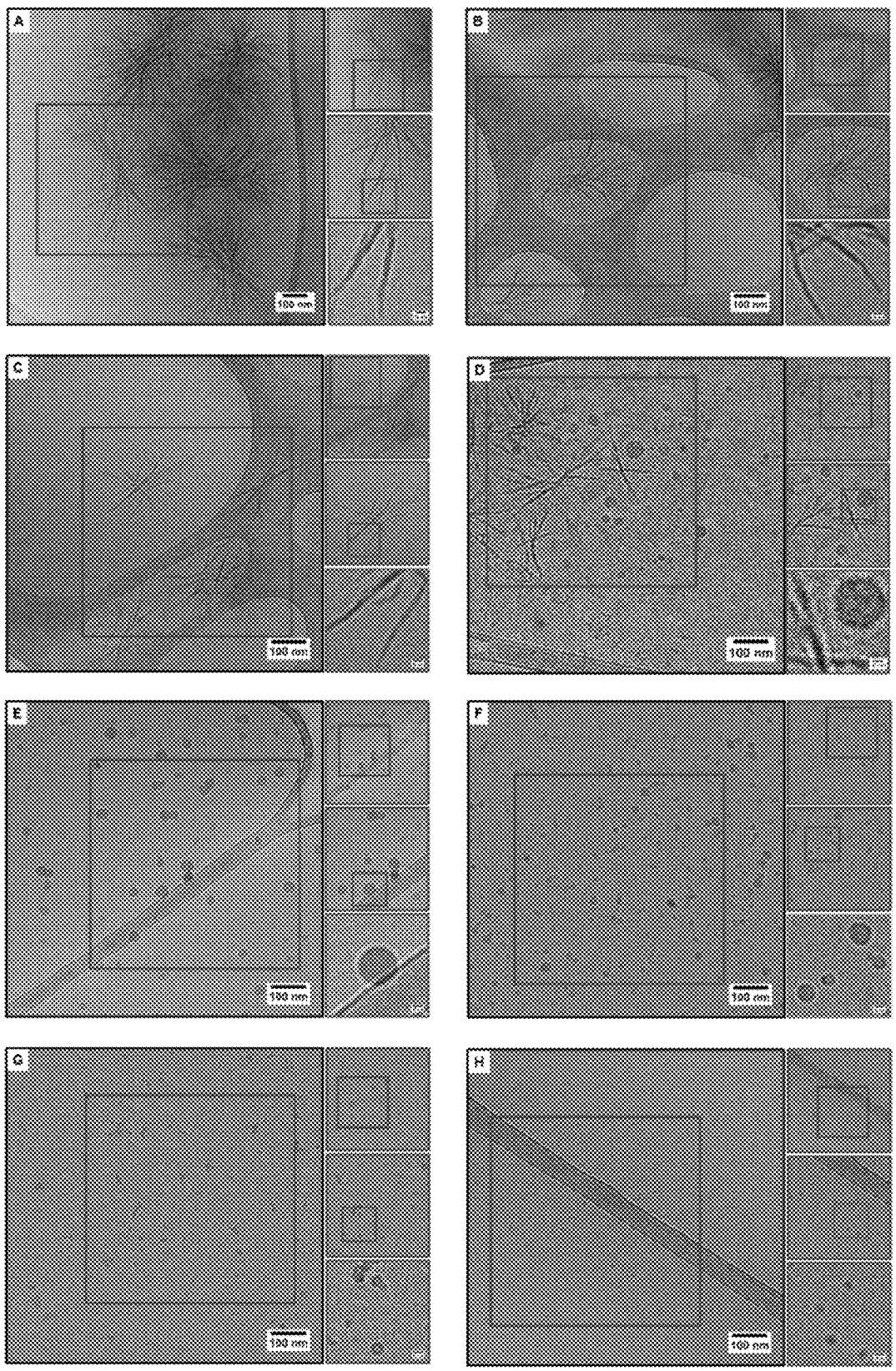
FIG. 15. CryoTEM of $PPSU_{20}$ nanogels in water. The nanogels were prepared by stepwise hydration of DMSO solutions of $PPSU_{20}$ (see FIG. 2a). Images were obtained by CryoEM after removal of DMSO. Size of selection: red (600 nm×600 nm), purple (300 nm×300 nm), blue (100 nm×100 nm).
Figure 16:
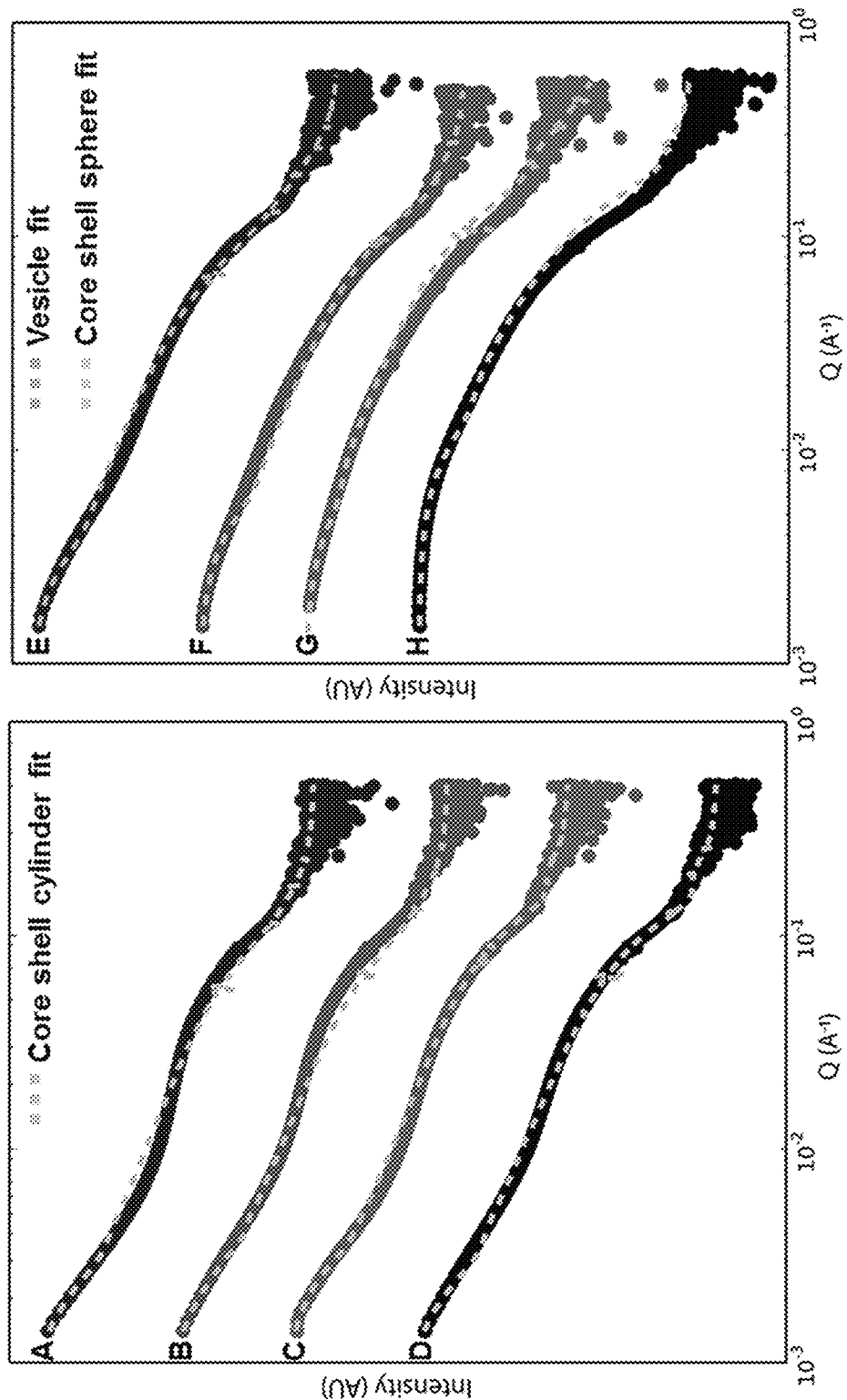
FIG. 16. SAXS of $PPSU_{20}$ nanogels in water. The samples are corresponding to FIG. 15.
Figure 17:
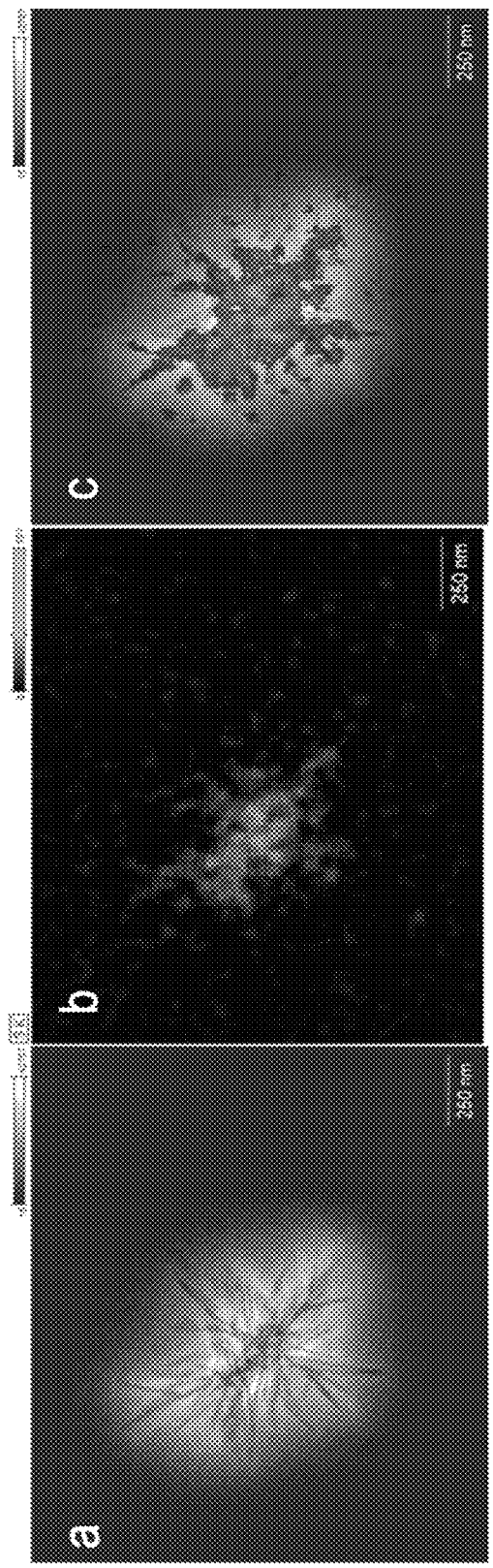
FIG. 17. Confirming the formation of nanobundle by negative-stained transmission electron microscopy and energy dispersive X-ray spectroscopy. (a) HAADF STEM image. (b) The corresponding sulfur EDS map on the right. (c) Overlay of base image and sulfur map. The samples correspond to sample C in FIG. 15.
Figure 18:
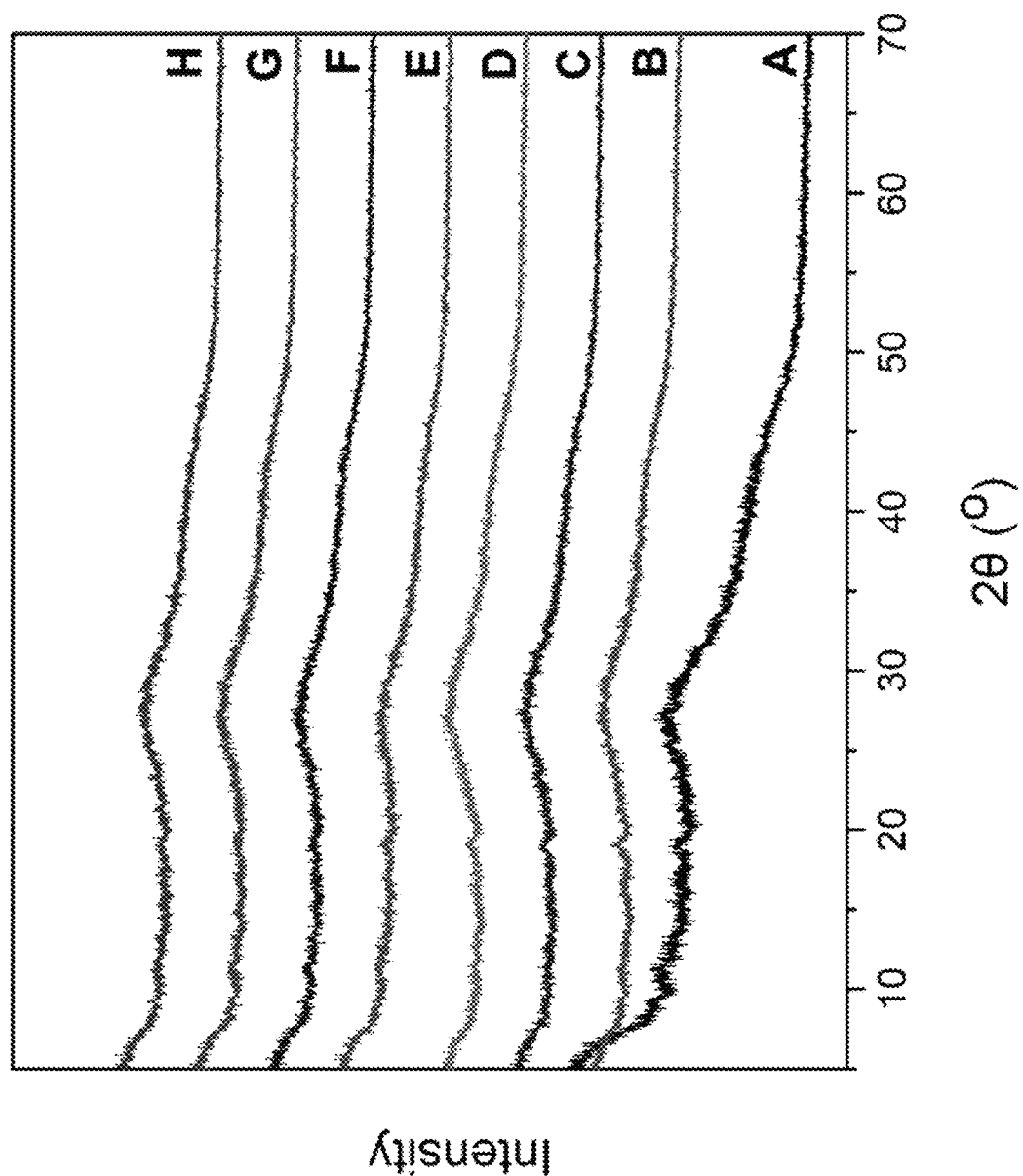
FIG. 18. WAXD patterns for $PPSU_{20}$ nanostructures. The samples are corresponding to FIG. 15.
Figure 20:
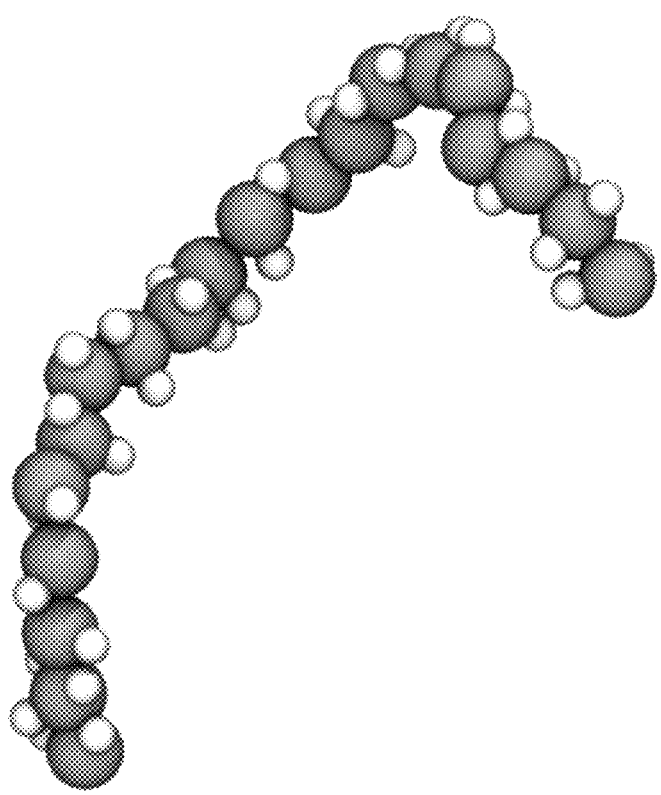
FIG. 20. Coarse-grained model of a $PPSU_{20}$ chain. Each chain is modeled by a linear bead-spring chain consisting of N=20 monomers. Each monomer carries three point charges: a positive charge in the backbone for the S atom (green sphere) and two negative charges for the 0 atoms (white spheres). The relative positions of the three point charges are maintained by harmonic springs between the S—O bonds and constraining the O—S—O angle. The non-bonded interactions between the coarse-grained monomers includes the excluded volume interaction and electrostatics.

In an effort to control the formation of specific nanostructures, we developed a simple strategy (FIG. 2a) to fabricate all the three nanogel morphologies from the same initial DMSO solution by employing distinct hydration histories (FIG. 15). In the strategy, we mixed DMSO solutions of PPSU$_{20}$ (25 mg/mL) with the same total volume of water with varying numbers of water addition steps. Cryo-TEM images revealed that larger nanobundles (FIG. 2b) formed in the case of multiple water additions while smaller spherical aggregates, including vesicular (FIG. 2c) and spherical (FIG. 2d) morphologies, were assembled using fewer hydration steps. These results were further confirmed by small-angle X-ray scattering (SAXS, FIG. 16), negative-stained transmission electron microscopy (FIG. 17), energy dispersive X-ray spectroscopy (EDS, FIG. 17) and dynamic light scattering (DLS), with the obtained physicochemical characteristics summarized in Table 5. No distinct patterns of PPSU crystals were observed by WXRD analysis (FIG. 2e and FIG. 18) or SAXS (FIG. 20, indicating amorphous structures of these nanoscale hydrogels. It is worthwhile to note that the surfaces of these nanoscale hydrogels possess enriched negative charges (Table 5), which support their dispersion in aqueous solution. We ascribed this phenomenon to the structural orientation of PPSU polymers, which predominantly orient their negative charges towards the surface of the 2D and 3D superstructures. Furthermore, spontaneous association in aqueous solution tends to embed hydrophobic propylene spacers that bear partially positive charge, which facilitates the exposure of negative charges on surfaces. The stepwise hydration of $PPSU_{20}$ demonstrated a facile dynamic method for programmable construction of synthetic nanostructures differing in morphologies and sizes from a single-component homopolymer.

TABLE 5

Physicochemical characteristics of $PPSU_{20}$ nanogels in water

| Sample [a] | Morphology [b] | Diameter [c] (nm) | Length [c] (nm) | Diameter [d] (nm) | Polydispersity Index [d] | Zeta Potential [d] (mV) |
|---|---|---|---|---|---|---|
| A | bundle | 14.8 ± 0.4 | 435.3 ± 8.1 | N/A | N/A | −38.43 ± 0.72 |
| B | bundle | 29.2 ± 0.5 | 344.7 ± 5.4 | N/A | N/A | −34.14 ± 0.43 |
| C | bundle | 29.4 ± 1.4 | 324.5 ± 4.0 | N/A | N/A | −47.83 ± 0.49 |
| D | bundle/vesicle | 18.2 ± 0.3 | 296.4 ± 1.5 | N/A | N/A | −34.67 ± 0.46 |
| E | vesicle | 75.2 ± 2.3 | N/A | 81.7 ± 13.6 | 0.207 ± 0.043 | −28.10 ± 0.70 |
| F | vesicle | 53.4 ± 4.0 | N/A | 37.3 ± 6.9 | 0.251 ± 0.004 | −46.23 ± 0.49 |
| G | vesicle/micelle | 33.0 ± 4.9 | N/A | 25.4 ± 6.0 | 0.259 ± 0.020 | −48.33 ± 1.10 |
| H | micelle | 18.6 ± 0.5 | N/A | 40.9 ± 9.2 | 0.236 ± 0.017 | −45.23 ± 1.40 |

[a] corresponding to FIG. 15.
[b] Determined by CryoTEM.
[c] Measured by SAXS.
[d] Measured by DLS.

Figure 3:
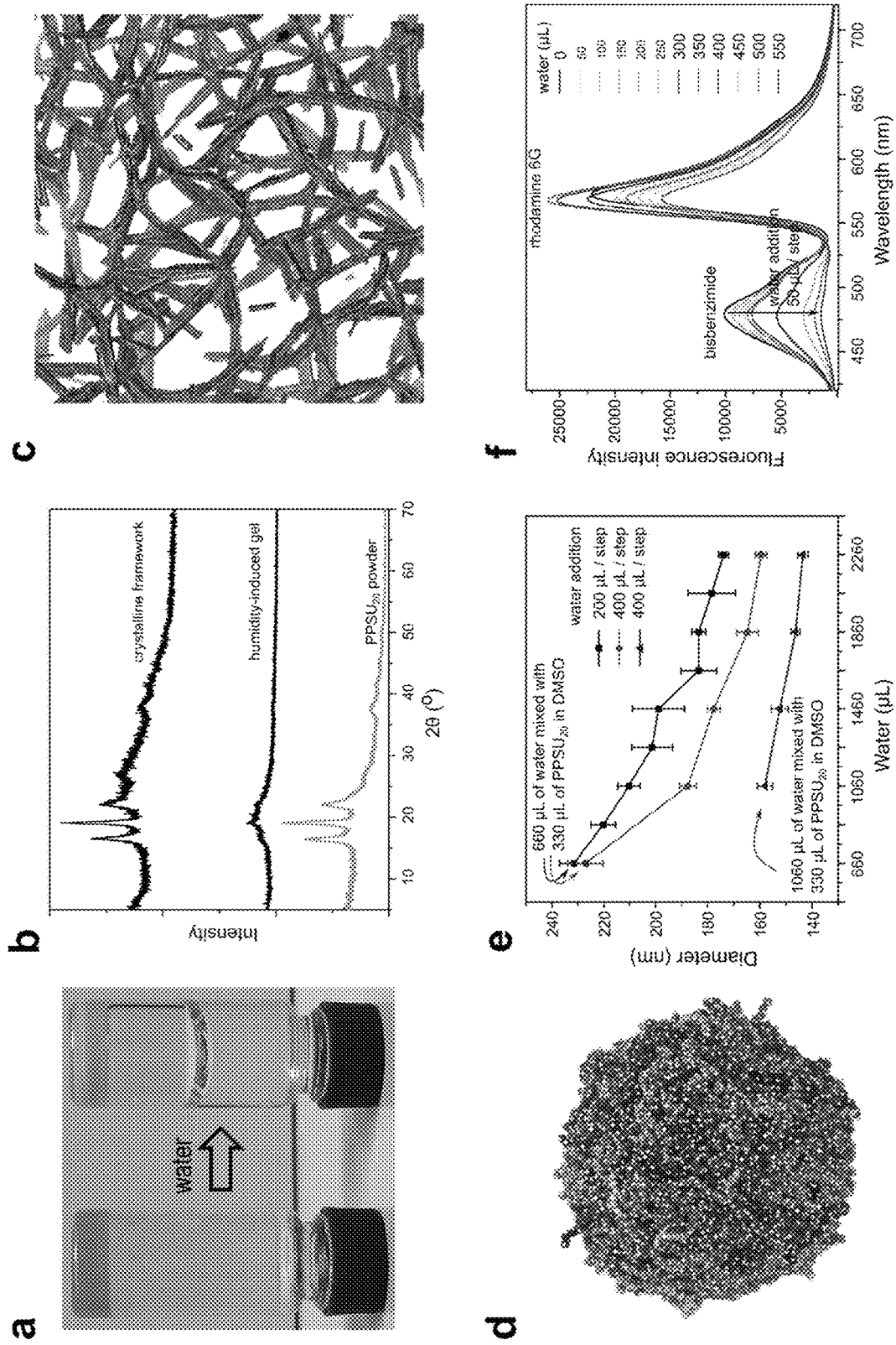
FIG. 3. Hydration impacting chain conformation and density. (a) Slow hydration leading to crystalline framework. The PPSU$_{20}$ hydrogel (colored by rhodamine B) was prepared by aging a DMSO solution of PPSU$_{20}$ (200 mg/mL) in humidity for 3 days. Adding an excess amount of water on the top of the gel allows slow solvent replacement for dense sulfone-sulfone bonding, which induces crystallization. (b) WAXD patterns for the humidity-induce gel, crystalline framework, and for comparison the powdered solid PPSU$_{20}$. (c-d) CGMD simulation snapshots showing the formation of bundles by rigid chains and a spherical hydrogel by flexible chains. Oxygen atoms are represented by the white spheres. (e) Collapse of PPSU$_{20}$ networks as indicated by the decreasing nanogel size upon stepwise hydration. (f) Collapse of PPSU$_{20}$ assemblies enabling FRET from bisbenzimide to rhodamine 6G. Bisbenzimide (0.01 mg/mL) and rhodamine 6G (0.01 mg/mL) were added to 1 mL of DMSO solution of PPSU$_{20}$ (5 mg/mL), followed by fluorescence titrations of the system with water (50 μL/step, E$_x$=375 nm).
Figure 19:
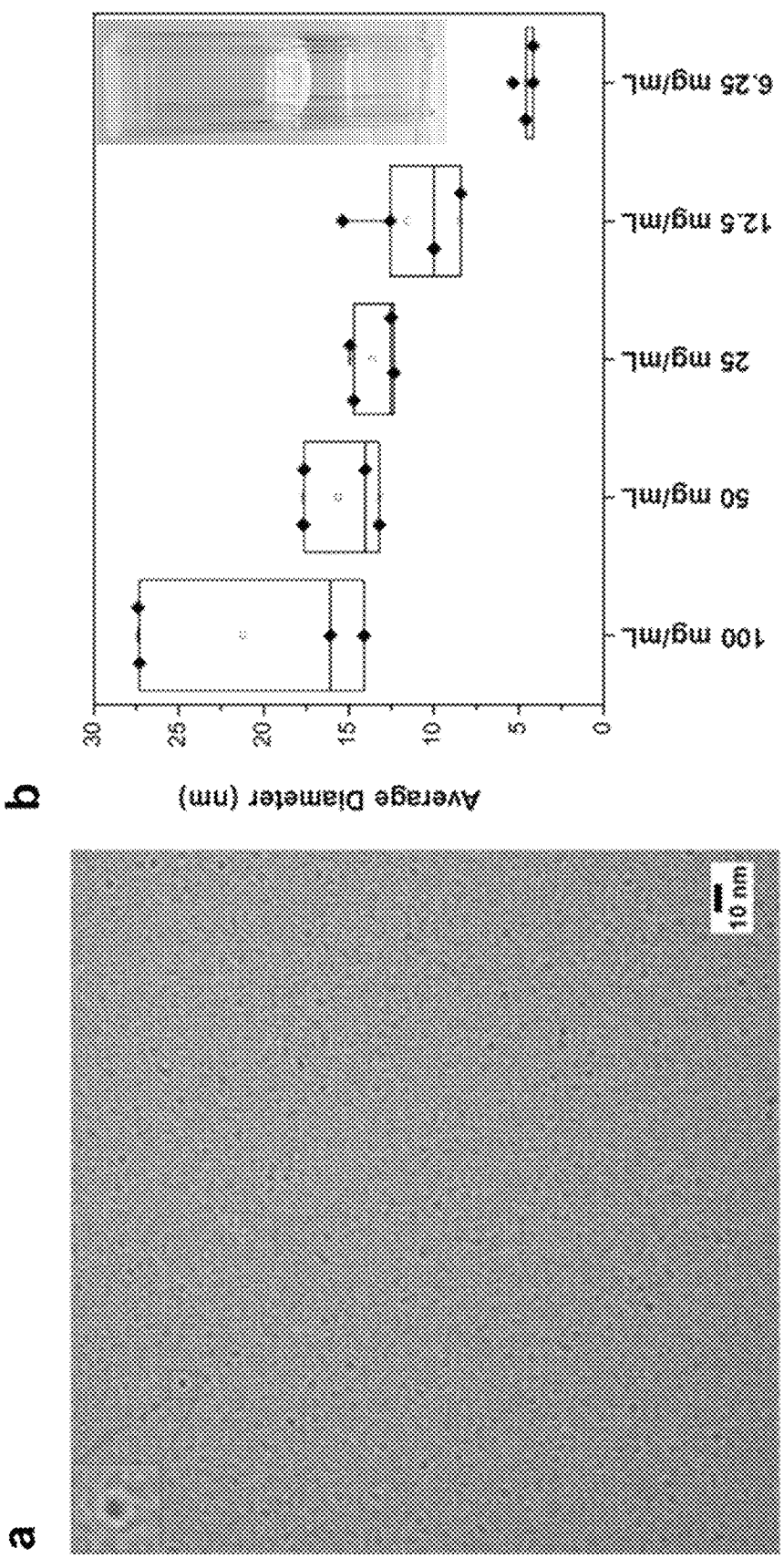
FIG. 19. Quick hydration of DMSO solution of $PPSU_{20}$ leading to tiny spherical nanogels. (a) CryoTEM image showing the formation of tiny spherical nanogels by quick hydration of 50 μL $PPSU_{20}$ solution (25 mg/mL in DMSO) with 1 mL of water (scale bar=10 nm, the red selection=10 nm×10 nm). (b) Number-average diameters determined by DLS for micellar solutions prepared from quick hydration of 50 μL $PPSU_{20}$ solutions (different concentrations in DMSO) by the using of 1 mL water. Inset is a clear solution prepared by mixing a 25 mg/mL DMSO solution of $PPSU_{20}$ with 1 mL of water, showing strong Tyndall effect.

Regardless of the concentrations investigated, one-step hydration of $PPSU_{20}$ solutions in DMSO using an excess amount of water generated ultra-small (<15 nm) nanogels (FIG. 19). These results indicate that thousands of polymer chains in an actual solution would likely entangle into interpenetrating networks following a one-step hydration, effectively freezing the morphology and preventing further conformational transitions. To fabricate crystalline frameworks in water that were predicted by the AAMD simulations (FIG. 9), cohesion among sulfones needs to be strong enough to create a stable network but not too strong to prevent dynamic exchange. In an alternative strategy, $PPSU_{20}$ in highly concentrated DMSO solutions were found to crosslink into crystalline frameworks via water diffusion. Careful addition of an excess amount of water on the top of a humidity-induced gel (FIG. 3a) resulted in the formation of a stiff crystalline solid possessing a similar WAXD pattern as that of bulk $PPSU_{20}$ powder (FIG. 3b). This result is consistent with our postulate that network formation occurs before and preferential to crystallization. The crystallization of $PPSU_{20}$ starts from a sulfone-bonded network, followed by continuous small-scale spatial redistribution of these sulfone network bonds to enable formation of a crystalline framework structure. This network rearrangement differs from common processes of crystallization-driven self-assembly, which involves the formation and subsequent growth of seeds by recruitment of crystalline blocks in a selective solvent (26, 27).

Figure 21:
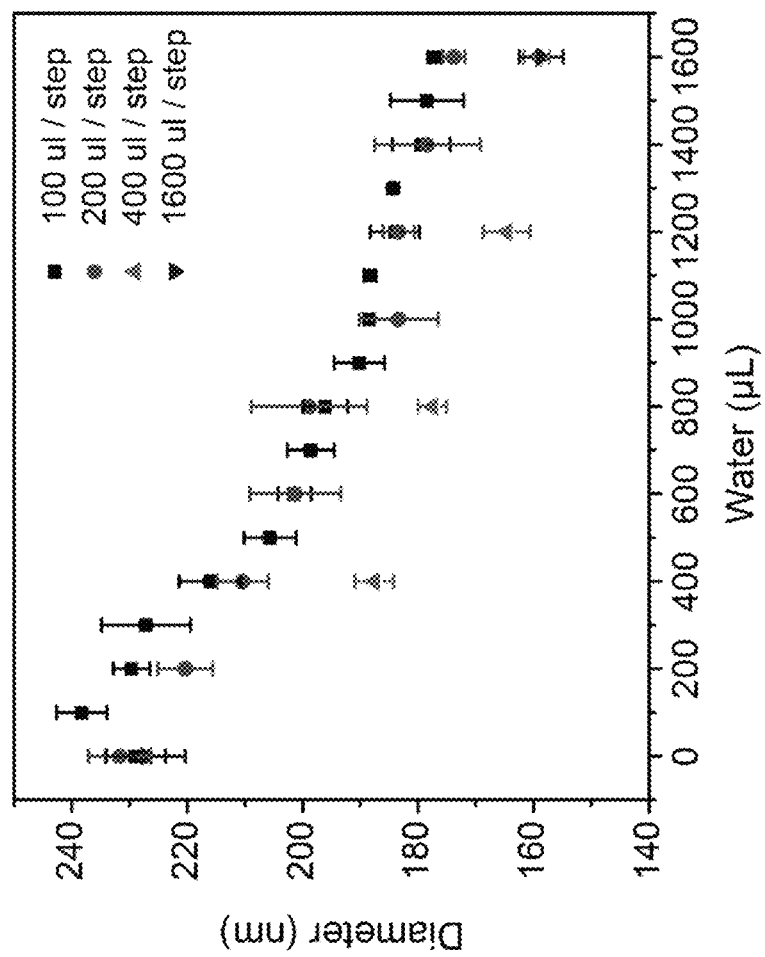
FIG. 21. DLS measurements showing sizes decreasing of $PPSU_{20}$ assemblies upon stepwise hydration. The sizes of assemblies were assessed following the initial mixing of 330 μL of DMSO solution of $PPSU_{20}$ (25 mg/mL) with 660 μL water and subsequent stepwise hydration.
Figure 22:
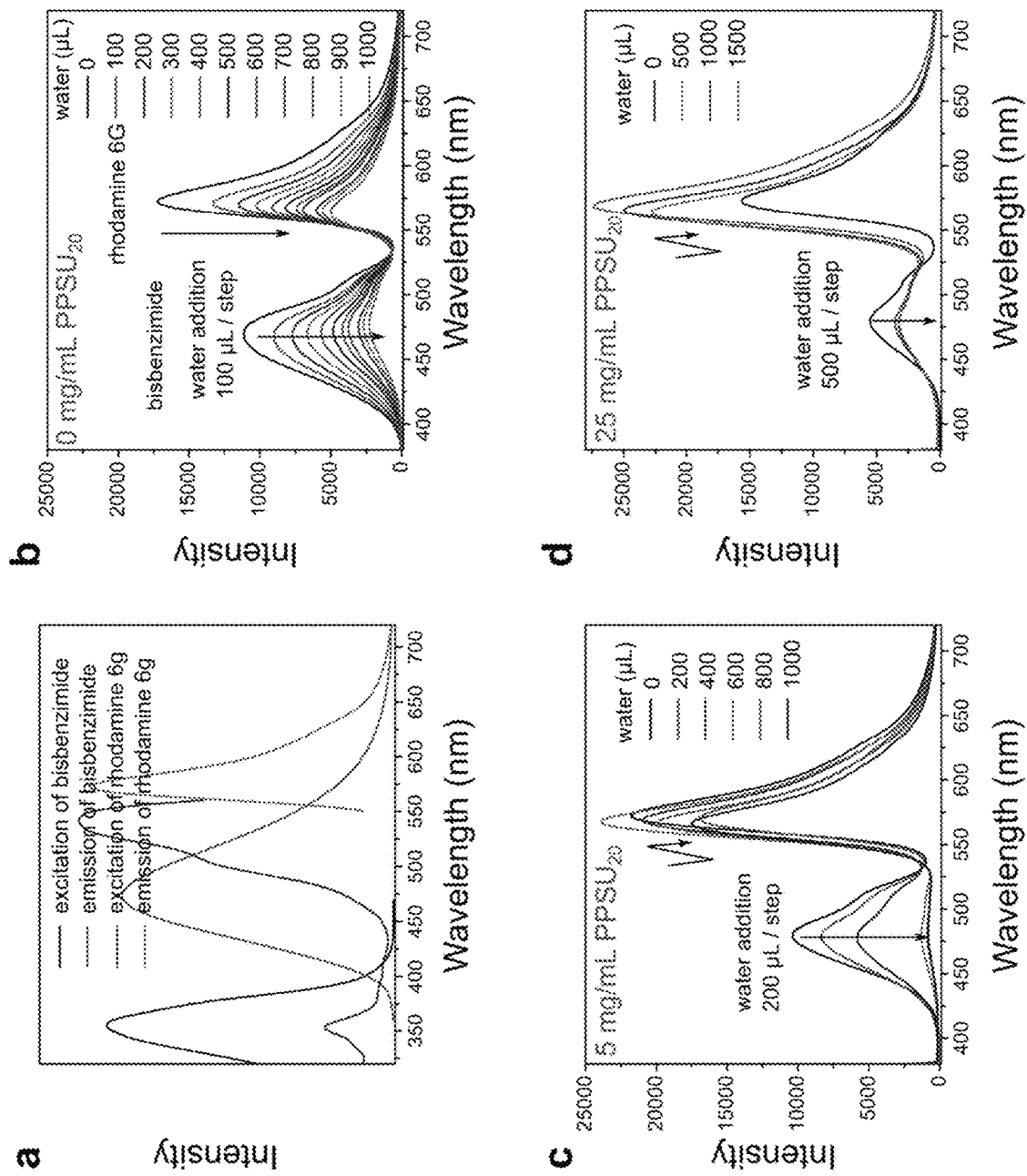
FIG. 22. Forster resonance energy transfer (FRET) from bisbenzimide to rhodamine 6G. (a) Excitation and emission spectra of bisbenzimide to rhodamine 6 g in DMSO. (b-d) Fluorescence titration ($E_x$=375 nm) experiments of 1 mL DMSO solution of bisbenzimide (0.01 mg/mL), rhodamine 6G (0.01 mg/mL), and $PPSU_{20}$ (0, 5, 25 mg/mL) with water. (b) Without $PPSU_{20}$, water dilutes the solution and decreases fluorescence intensity for both bisbenzimide and rhodamine 6 g. (c-d) In the presence of $PPSU_{20}$, obvious FRET signals from bisbenzimide to rhodamine 6 g are induced upon stepwise hydration. The arrows denote the change of fluorescence intensity.

The work described above using kinetically controlled self-assembly of $PPSU_{20}$ hydrogels results in crystalline frameworks or nanostructured hydrogels of spherical, vesicular and cylindrical morphologies in aqueous solution. These hierarchical superstructures are achieved via multiple levels of sulfone organization. The first level involves the inter-chain interactions that lead to initial network formation, which is followed by a second level of sulfone-sulfone bonding that locks the polymer chains into a stable conformation. In the latter, the hydration history from multiple small additions of water leads to bundling of $PPSU_{20}$ chains into highly organized low curvature ribbons that increase persistence length, similar to bundling of DNA origami filaments (28). Alternatively, quick hydration generates disordered spherical hydrogels which contain coiled $PPSU_{20}$ chains that experience greatly decreased electrostatic repulsion and strong interactions. Further hydration triggers the collapse and rearrangement of these sulfone-sulfone bonded into compact structures but imparts little change in overall chain stiffness. The formation of nanogel vesicles may be explained by taking into account the diffusivity of water into nanoscale aggregates that are stabilized by dynamic sulfone-sulfone bonding. The proximity of the outer layers of large spherical hydrogels to the water interface will promote stable cross-linking and prevent further structural rearrangement, resulting in an outer shell encapsulating an inner lumen of lower density sulfone-bonding. Taken together, the diverse sulfone-sulfone bonded networks formed by $PPSU_{20}$ network self-assembly provided a strong basis to infer distinct chain conformations specified by hydration histories. We therefore explored through coarse-grained molecular dynamics (CGMD) simulations (FIG. 20) the effect of chain stiffness on self-assembly. Snapshots are depicted in FIGS. 3c & d, showing the formation of bundles in a framework of rigid polymer chains and a spherical, highly cross-linked hydrogel of flexible $PPSU_{20}$. To further assess dynamic changes in nanogel size upon continued hydration, we tracked $PPSU_{20}$ assemblies using DLS and observed significant decreases in diameter as the ratios of water increased in water-DMSO mixed systems for different hydration histories (FIG. 3e and FIG. 21). Fluorescence titrations of $PPSU_{20}$ assemblies with water were also performed to assess the collapse of these polymer networks using the Forster resonance energy transfer (FRET) pair of bisbenzimide and rhodamine 6G (FIG. 22). In FIG. 3f, we first observed the fluorescence intensity of both dyes to decrease upon water dilution, followed by a FRET signal from bisbenzimide to rhodamine 6G. The FRET efficiency improved upon further hydration, suggesting decreasing sizes and thus collapse of $PPSU_{20}$ aggregates. These results demonstrate a compressing process for $PPSU_{20}$ networks that achieves smaller structures as water ratios increase.

Figure 23:
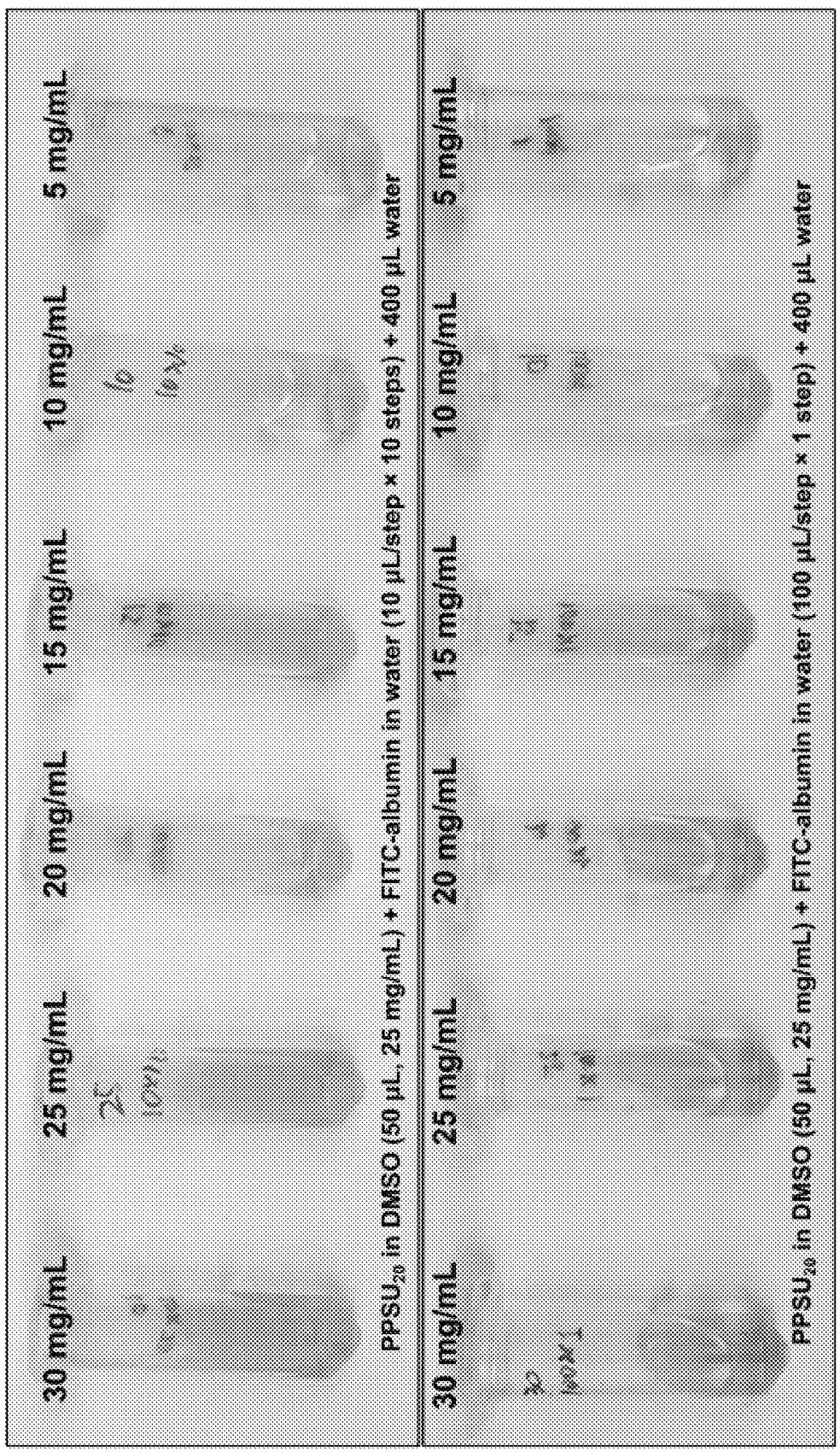
FIG. 23. Loading FITC-albumin during $PPSU_{20}$ assembly. 50 μL of $PPSU_{20}$ solutions (25 mg/mL in DMSO) were added stepwise with 100 μL of aqueous FITC-albumin solutions (30 mg/mL to 5 mg/mL) and then one-time with 400 μL of water. Each step was followed by vortexing to thoroughly mix the samples. Photos were taken after centrifugation (16000 g, 10 min).

The sulfone-sulfone bonded networks of $PPSU_{20}$ are mimetic of electrostatic networks in dimethylsulfone, a high-temperature polar solvent that can dissolve a wide range of organic solutes and is miscible with many other solvents. We investigated the use of PPSU$_{20}$ nanostructured hydrogels to capture organic molecules from DMSO or aqueous solution using the stepwise hydration strategy. The results are shown in Table 1, wherein exceptionally high encapsulation efficiencies (EE) of >95% were observed for a wide range of molecules, including hydrophobic Nile red and water-soluble fluorescein isothiocyanate (FITC), doxorubicin hydrochloride (DOX/HCl), dextran, green fluorescent protein (GFP), DNA, and RNA. We also investigated the loading of FITC-labeled albumin (FITC-BSA), a model protein, at varying concentrations (FIG. 23). The rapid water-induced collapse of PPSU$_{20}$ networks allowed encapsulation of nearly 100% of protein molecules from aqueous solutions with up to 80% encapsulation capacity (w/w) (Table 1, entry 5 to 7). Over 80% EE was achieved when nanoparticles contained 20% more protein than polymer by mass (Table 1, entry 8).

TABLE 1

Encapsulation efficiency of various molecules captured during PPSU$_{20}$ self-assembly[a]

| Entry | Molecule[b] | Mass ratio (drug/PPSU$_{20}$) | Encapsulation efficiency (%)[c] 100 μL/step | 10 μL/step |
|---|---|---|---|---|
| 1 | Nile red | 0.004 | >98 | >96 |
| 2 | FITC | 0.004 | >99 | >99 |
| 3 | DOX/HCl | 0.08 | >97 | >96 |
| 4 | Dextran | 0.08 | >96 | >96 |
| 5 | Albumin | 0.08 | >99 | >99 |
| 6 | Albumin | 0.4 | >99 | >99 |
| 7 | Albumin | 0.8 | >96 | >96 |
| 8 | Albumin | 1.2 | 80 | 83 |
| 9 | GFP[d] | 0.016 | >99 | >99 |
| 10 | RNA | 0.016 | >96 | >98 |
| 11 | DNA | 0.016 | >96 | >97 |

[a]100 μL of aqueous drug (except Nile red) solutions were mixed stepwise with 50 μL of PPSU$_{20}$ solution (25 mg/ml in DMSO), followed by a one-time quick hydration using 400 μL of water. Nile red was loaded using its DMSO solution.
[b]GFP = Recombinant A. victoria GFP protein. Dextran (M$_w$ = 4,000), Albumin, RNA, and DNA are conjugated with FITC.
[c]Encapsulation efficiency is defined as the ratio of the amount of molecules in the assemblies to the total amount applied in formulation. The encapsulation efficiencies were calculated by fluorescence measurements.
[d]GFP has no detectable fluorescence after encapsulation.

Figure 24:
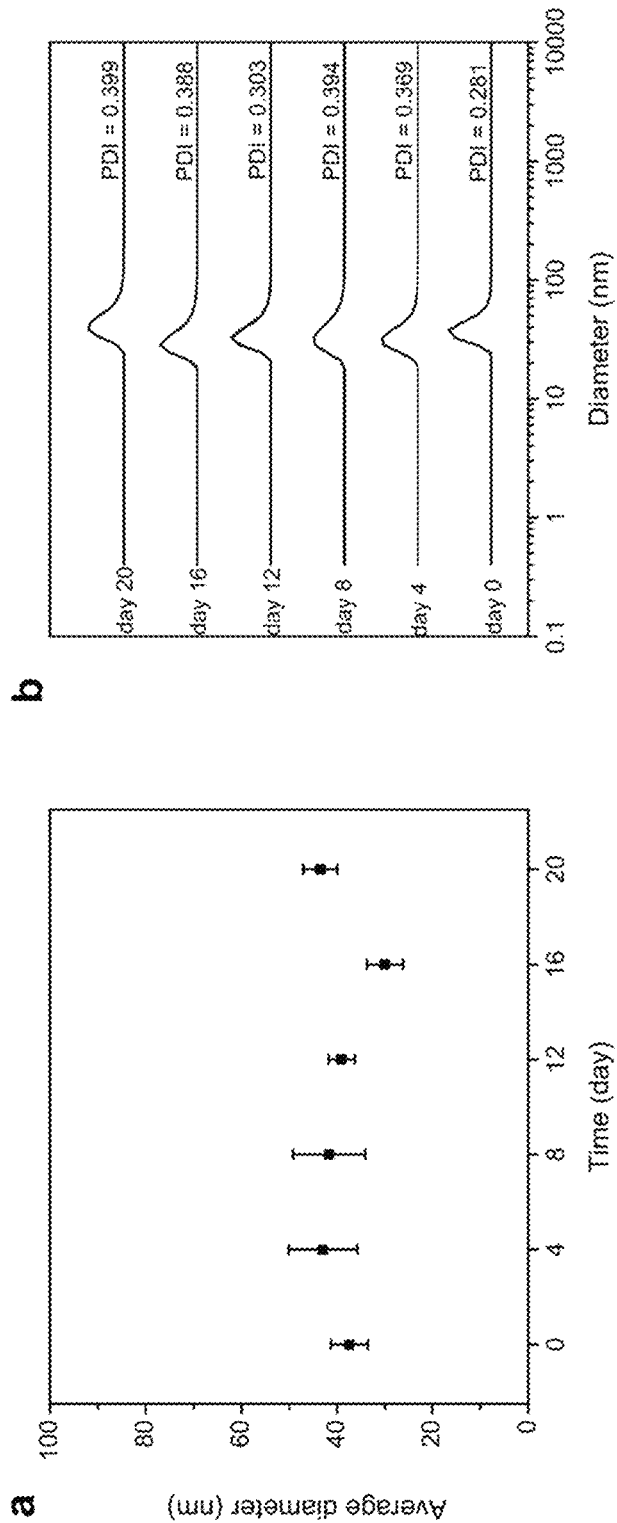
FIG. 24. Stability study of $PPSU_{20}$ vesicular nanogels in water over time. (a) Number average diameter obtained by DLS showing no statistically significant difference between day 0 with day 4-20. Error bars represent the standard deviation from three parallel experiments. (b) Representative DLS plots giving the size distribution of $PPSU_{20}$ vesicular nanogels in the range of 20-100 nm without occurrence of nanogel aggregation.
Figure 25:
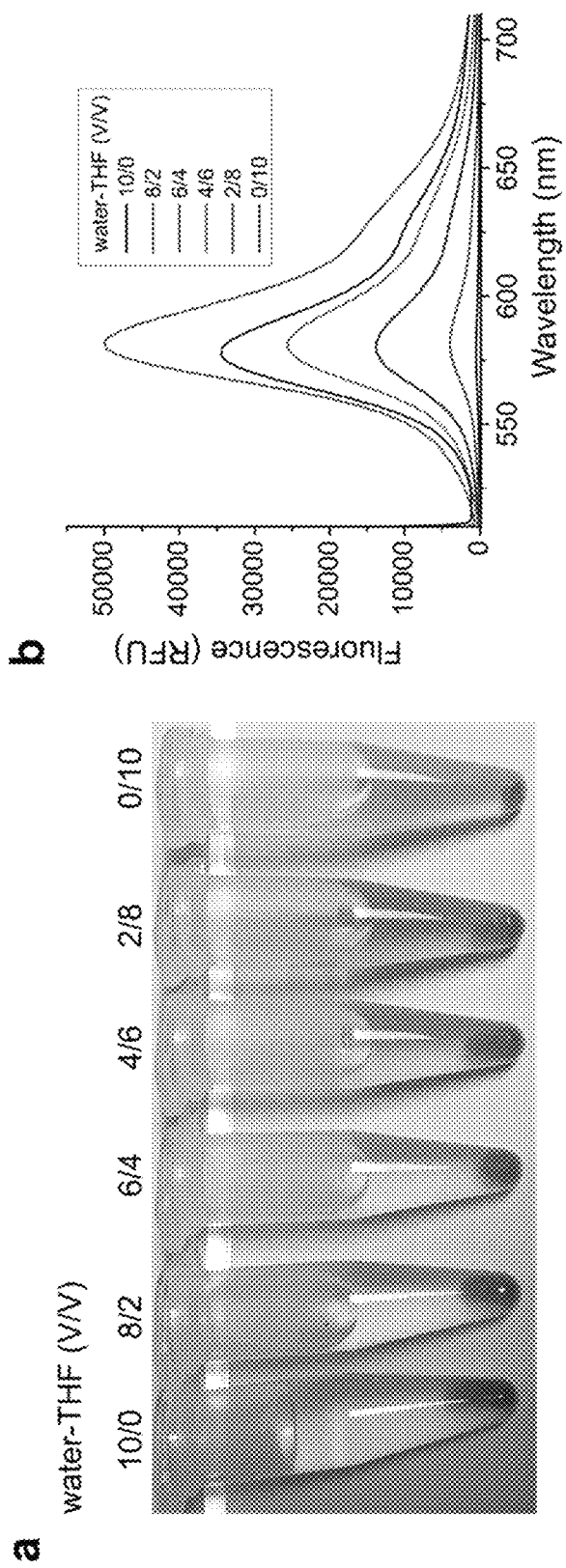
FIG. 25. Leakage of rhodamine B (Rh B) from $PPSU_{20}$ vesicular nanogels in tetrahydrofuran (THF)-water mixed systems. (a) Photos of Rh B-loaded $PPSU_{20}$ vesicular nanogels in THF-water mixed solvents after 3-day incubation (room temperature) and centrifugation (16000×g, 10 min). (b) Fluorescence spectra of the corresponding supernatants in (a). The supernatants (0.5 mL) were diluted with THF and water to 2 mL of water-THF (8/2, V/V) mixed solvent for fluorescence measurements, $E_x$=500 nm.

PPSU$_{20}$ nanostructures were highly stable in water and no dense aggregates or precipitating was observed by aging a suspension of vesicular nanogels (FIG. 24). When containing payloads, no premature payload release was observed in water after days of incubation at room temperature (FIG. 25). Given the possibility of breaking the nanostructures using less polar solvents, we proceeded to investigate the stability of PPSU$_{20}$ vesicular nanogels in tetrahydrofuran (THF)-water mixed systems. Rhodamine B (Rh B) was encapsulated in the nanogels to evaluate the degradation. We followed the leakage of Rh B in these systems and observed that the nanogels are less stable in THF-water mixed solvents than in water or in THF (FIG. 25). This result is consistent with our conclusion that sulfone-sulfone interactions are susceptible to solvent polarity.

The high stability of PPSU nanogels in water provides insight into the mechanism of drug encapsulation. Starting from a swollen network that shows high affinity for a wide range of organic solutes, subsequent hydration induces quick collapse of the sulfone-sulfone bonded network (FIG. 3c-f), in which the diffusivity of encapsulated molecules decreases significantly once they are incorporated into the nanogel. We inferred that such a molecular trapping mechanism should lead to physicochemical changes to the nanogels upon encapsulation due to the properties of the payload.

Figure 4:
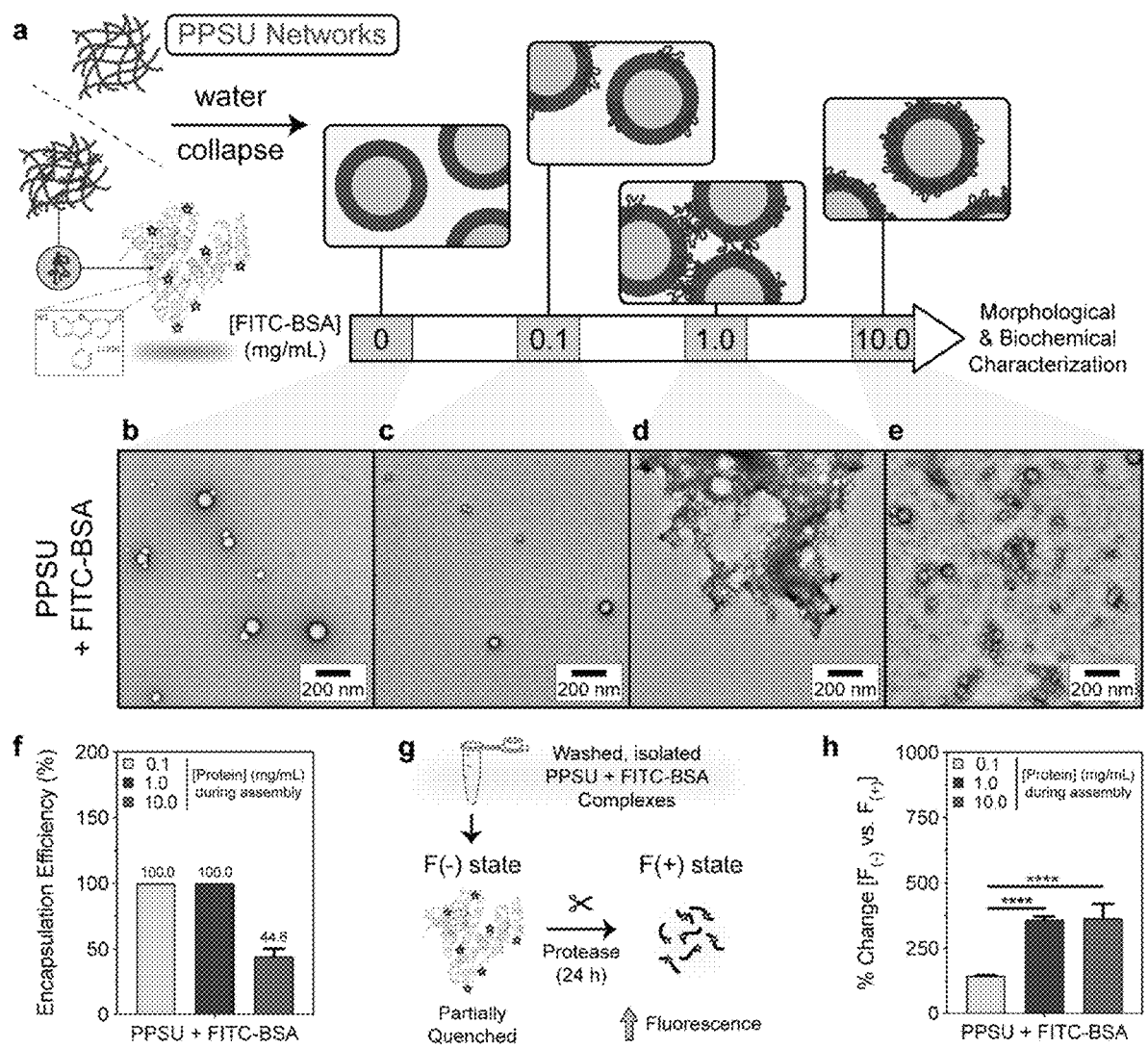
FIG. 4. PPSU$_{20}$ nanostructures assembled with FITC-BSA demonstrate the PPSU$_{20}$/protein ratio alters morphology and the protein cargo is accessible to protease in the external environment. (a) PPSU$_{20}$ nanostructures (5 mg) were assembled with a concentration series of aqueous FITC-BSA (0.1, 1.0, or 10 mg/mL). PPSU$_{20}$ nanostructures prepared without protein (0 mg/mL FITC-BSA) were included as a control. (b-e) Transmission electron microscopy of negatively stained specimens. (b) PPSU$_{20}$ nanostructures absent of protein. PPSU-FITC-BSA complexes assembled in the presence of (c) 0.1, (d) 1.0, or (e) 10.0 mg/mL FITC-BSA (purposefully overloaded sample and the free FITC-BSA was not removed). Scale bar=200 nm. (f) Encapsulation efficiency of FITC-BSA protein cargo. (g) Trypsin proteolysis assay illustration. In the absence of protease, FITC-BSA is partially quenched and exhibits weak fluorescence. After trypsin treatment, FITC-labeled peptides are released and the fluorescence of the FITC fluorophore increases. (h) The percentage change in FITC fluorescence after trypsin treatment. Increased FITC fluorescence is a readout of whether embedded protein interfaces with the external aqueous environment. Error bars represent s.e.m. (n=3). Statistical significance was determined by Tukey's multiple comparisons test. ****p<0.0001.
Figure 26:
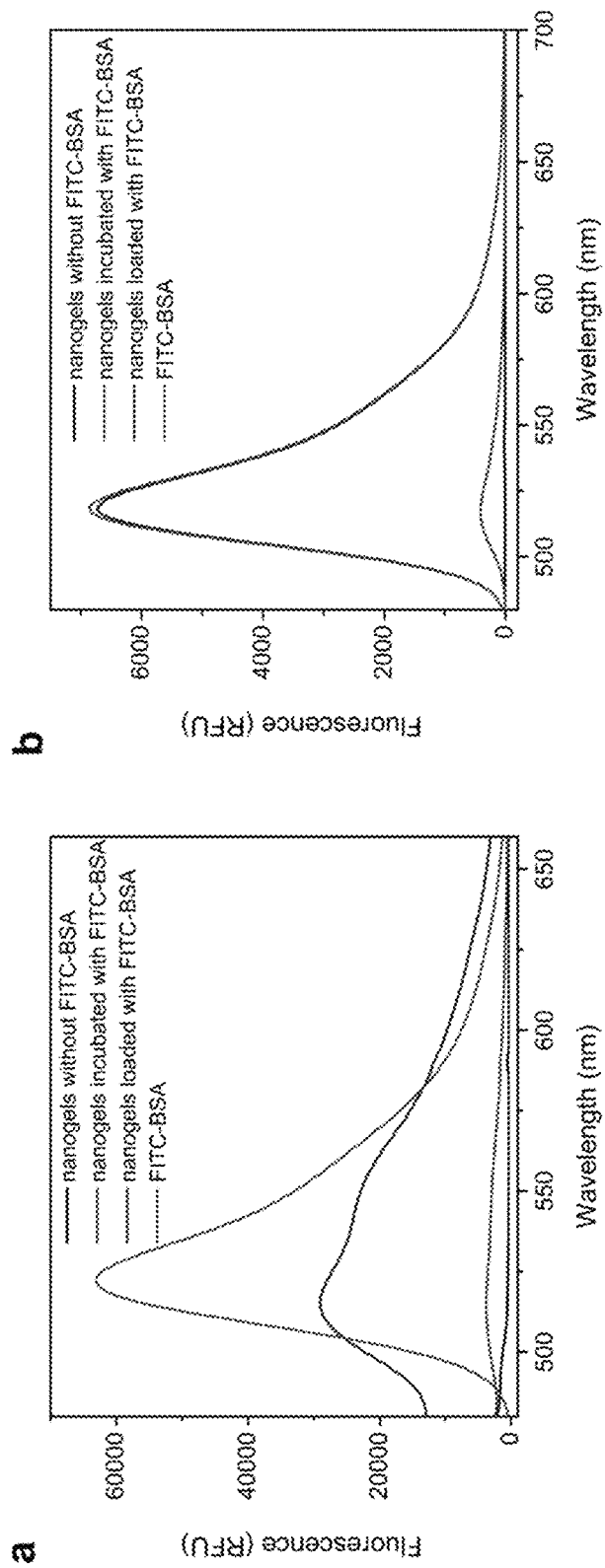
FIG. 26. Fluorescence spectra ($E_x$=460 nm) verifying negligible adsorption of FITC-BSA by preformed $PPSU_{20}$ vesicles. (a) Fluorescence spectra of blank vesicles, FITC-BSA-adsorbed vesicles, FITC-BSA-loaded vesicles, and for comparison FITC-BSA (0.1 mg/mL) in water. FITC-BSA molecules were highly concentrated after encapsulation in nanogels and the fluorescence was partially quenched in water. (b) Fluorescence spectra of blank vesicles, FITC-BSA-adsorbed vesicles, FITC-BSA-loaded vesicles, and for comparison FITC-BSA (0.01 mg/mL) in aqueous NaOH (0.2 N) solution. Fluorescence of FITC-BSA recovered in aqueous NaOH solution due to the breaking of vesicular nanogels. Fluorescence quantitative analysis ($E_m$=518 nm) confirmed that while the encapsulation efficiency was 97.8%, the adsorption efficiency of FITC-BSA was 6.0%. $E_x$=460 nm FIG. 27. Transmission electron microscopy of aqueous FITC-BSA stained with 1.5% uranyl formate as a control. The concentrations of the protein samples (a-d) were 0, 0.1, 1.0, and 10 mg/mL, respectively.
Figure 27:
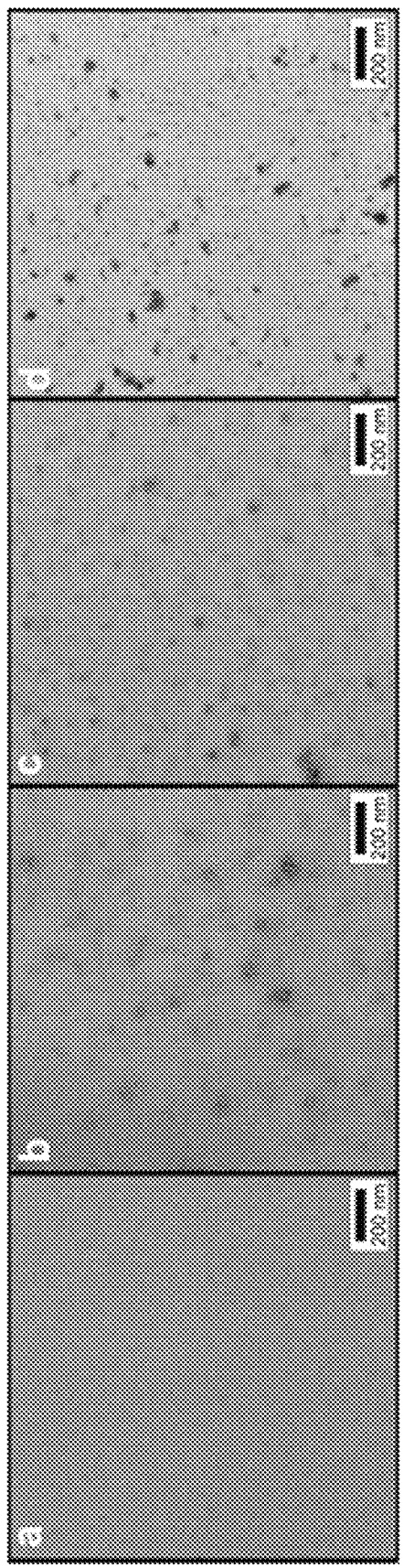

To investigate the trapping of protein within PPSU nanogels without interference from nonspecific protein adsorption, we employed FITC-BSA, which possesses a net negative charge that would minimize interactions with the negatively charged PPSU nanogel surfaces (FIG. 26). When PPSU$_{20}$ assembly was induced by a concentration series of aqueous FITC-BSA solution instead of pure water (FIG. 4a), we found that both nanogel diameter and zeta potential were influenced by FITC-BSA (Table 6). TEM images on negatively stained samples (FIGS. 4b-e and FIG. 27) revealed that while a low ratio of FITC-BSA (0.1 mg/mL, 1.6% w/w protein/PPSU) to PPSU had no impact on morphology (FIG. 4b-c), increasing the concentration of FITC-BSA to 1.0 mg/mL (16% w/w protein/PPSU) induced formation of macroscale aggregates consisting of vesicular nanogel complexes (FIG. 4d). Under the application of an even greater FITC-BSA concentration (10 mg/mL, 160% w/w protein/PPSU), we observed increased aqueous dispersibility and decreased size and polydispersity for the resulting nanogels with no evidence of macroscale gel formation (FIG. 4e, Table 6). Of note, loading of FITC-BSA at 0.1 mg/mL and 1.0 mg/mL achieved approximately 100% EE, and an impressive 45% EE was achieved in the presence of 10 mg/mL of protein, which generated nanogels possessing 72% protein (3.6 mg FITC-BSA/5 mg PPSU) by mass (FIG. 4f).

TABLE 6

DLS and zeta potential results of PPSU$_{20}$ vesicular nanogels formed in the presence of varying concentrations of FITC-BSA.

| FITC-BSA (mg/mL) | Diameter (nm) | Polydispersity Index | Zeta Potential (mV) |
|---|---|---|---|
| 0 | 61.9 | 0.24 | −53.7 ± 0.5 |
| 0.1 | 60.3 | 0.17 | −51.4 ± 0.7 |
| 1.0 | 3610.3 | 0.07 | −43.0 ± 0.7 |
| 10 | 151.4 | 0.43 | −44.8 ± 1.5 |

Each nanogel sample was assembled from 5 mg of PPSU.

Figure 28:
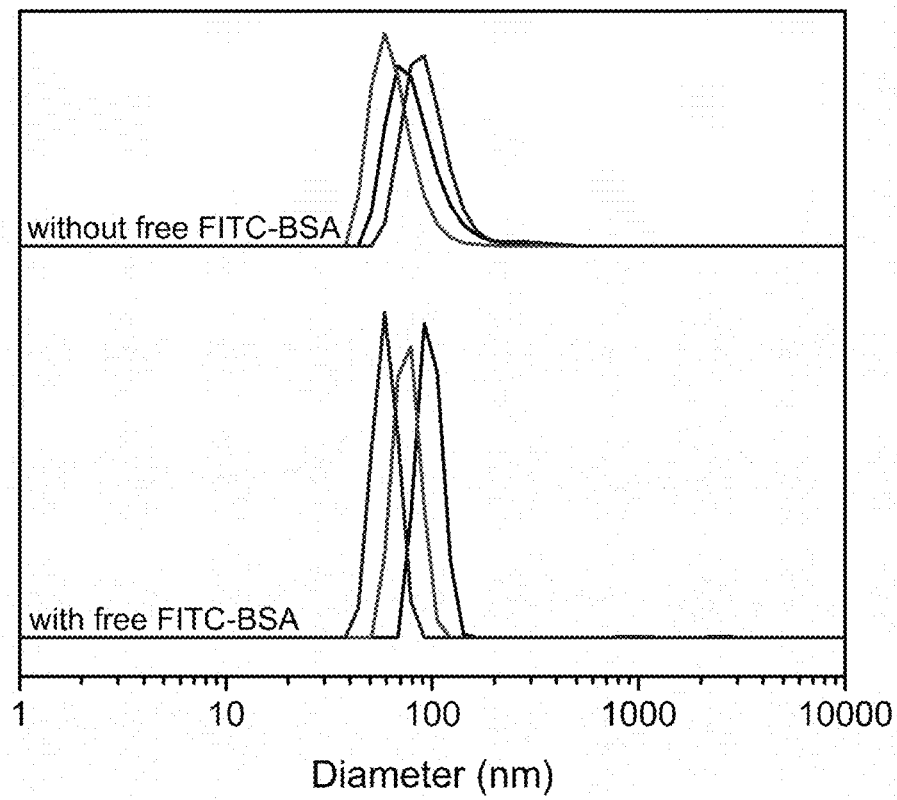
FIG. 28. DLS plots giving the size distribution of $PPSU_{20}$ vesicular nanogels that were saturated loaded with FITC-BSA. DLS measurements were performed for the samples with or without removing of free FITC-BSA by centrifugation. Black, red, and blue DLS plots were obtained from three parallel experiments. No statistically significant difference of average diameter between the two groups of samples were found.
Figure 29:
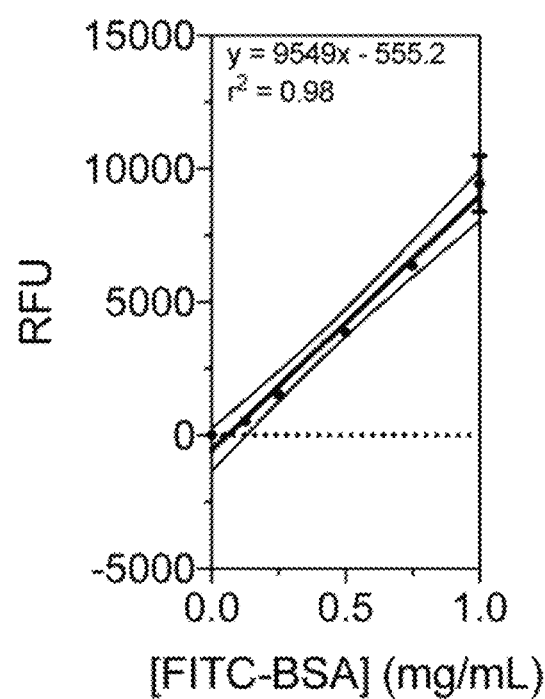
FIG. 29. Calibration curve of FITC-BSA fluorescence ($E_x$=495 nm, $E_m$=519 nm) for protein concentration measurement. Fit linear regression model (y=9549x-555.2; r2=0.98) was used for concentration measurement. Bands represent the 95% confidence interval. The calibration curve was constructed using three replicates.

These results suggest that FITC-BSA is accessible on the surface of the nanogels at densities dependent upon the initial loading concentration, and one potential explanation for this is described in the schematic of FIG. 4a. The lower concentration (0.1 mg/mL) resulted in minimal surface exposure of FITC-BSA, while the intermediate (1 mg/mL) loading concentration resulted in a partial surface exposure that allowed sharing of surface exposed protein between different nanogels to induce aggregation. Since free FITC-BSA molecules have limited influence on nanogels aggregation (FIG. 28), the saturated loading concentration (10 mg/mL) likely resulted in a high surface density of exposed FITC-BSA, which prevented aggregation between nanogels. We employed trypsin digestion to assess payload accessibility, and ~30-35% of encapsulated FITC-BSA was accessible to cleavage for the overloaded 10 mg/mL sample (FIGS. 4g-h and FIG. 29), suggesting considerable solution exposure of loaded protein.

We concluded that the observed high molecular encapsulation achieved by PPSU is due to tight molecular trapping, which allows us to fabricate novel protein-based nanocarriers without requiring covalent chemistries. By adjusting formulation conditions, nanogels up to 120% protein by mass could be achieved (Table 1). Our results thus demonstrate the possibility of extensive customization for the formation of protein/PPSU nanogels. The decreased fluorescence of GFP upon loading suggests that the current methodology may partially denature the protein structure, likely due to exposure to DMSO during loading (Table 1). Further investigations will be required to determine the limits of this platform for protein loading and retention of bioactivity as well as to assess the specific influences of different protein physicochemical properties on the final products.

Figure 30:
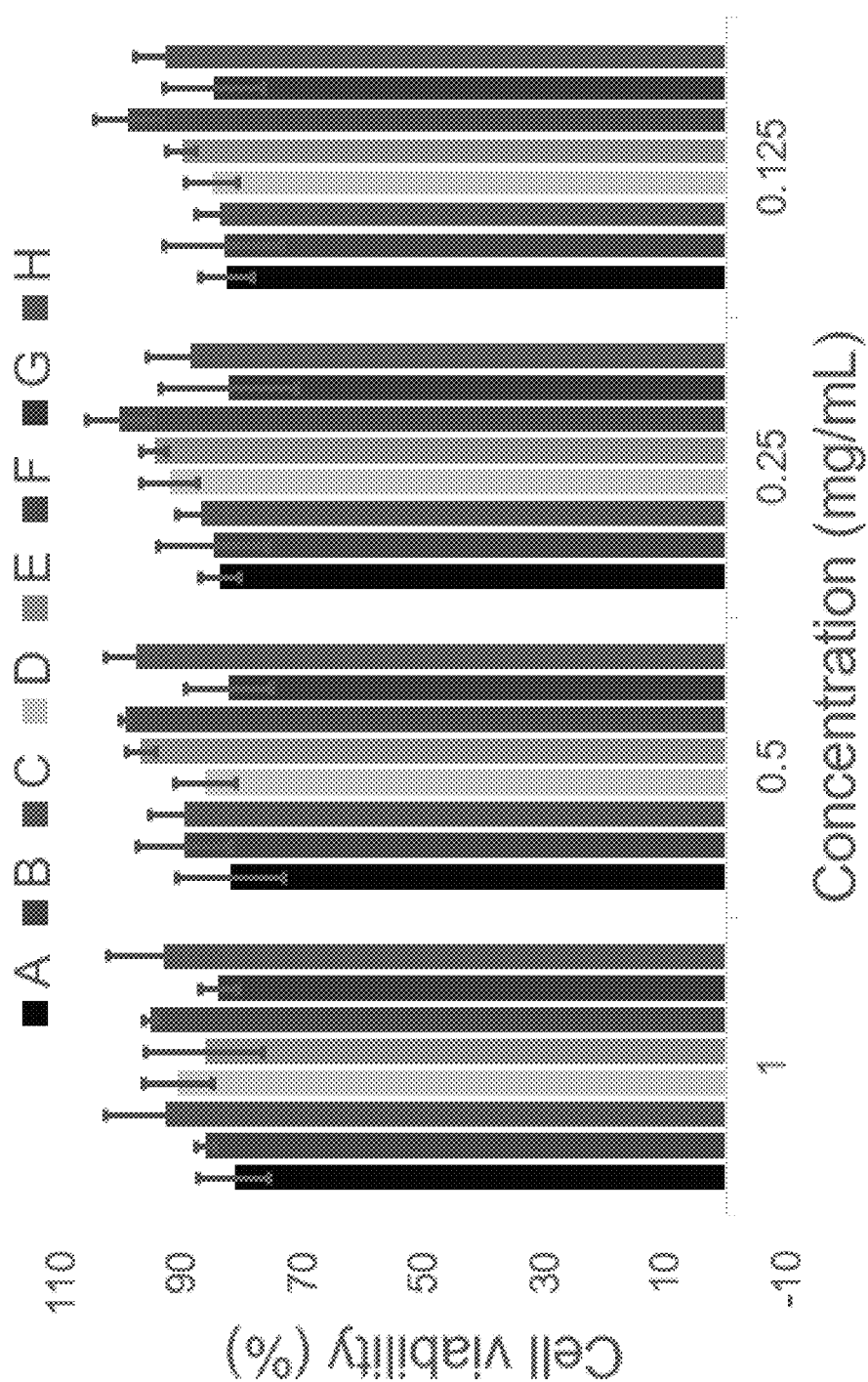
FIG. 30. MTT assay of PPSU$_{20}$ nanogels on RAW 264.7 cells for 24 h. Samples A-H are the corresponding samples prepared in FIG. 15. Error bars represent the standard deviation from four parallel experiments. No statistically significant difference was found between the experimental materials and the PBS control group.
Figure 31:
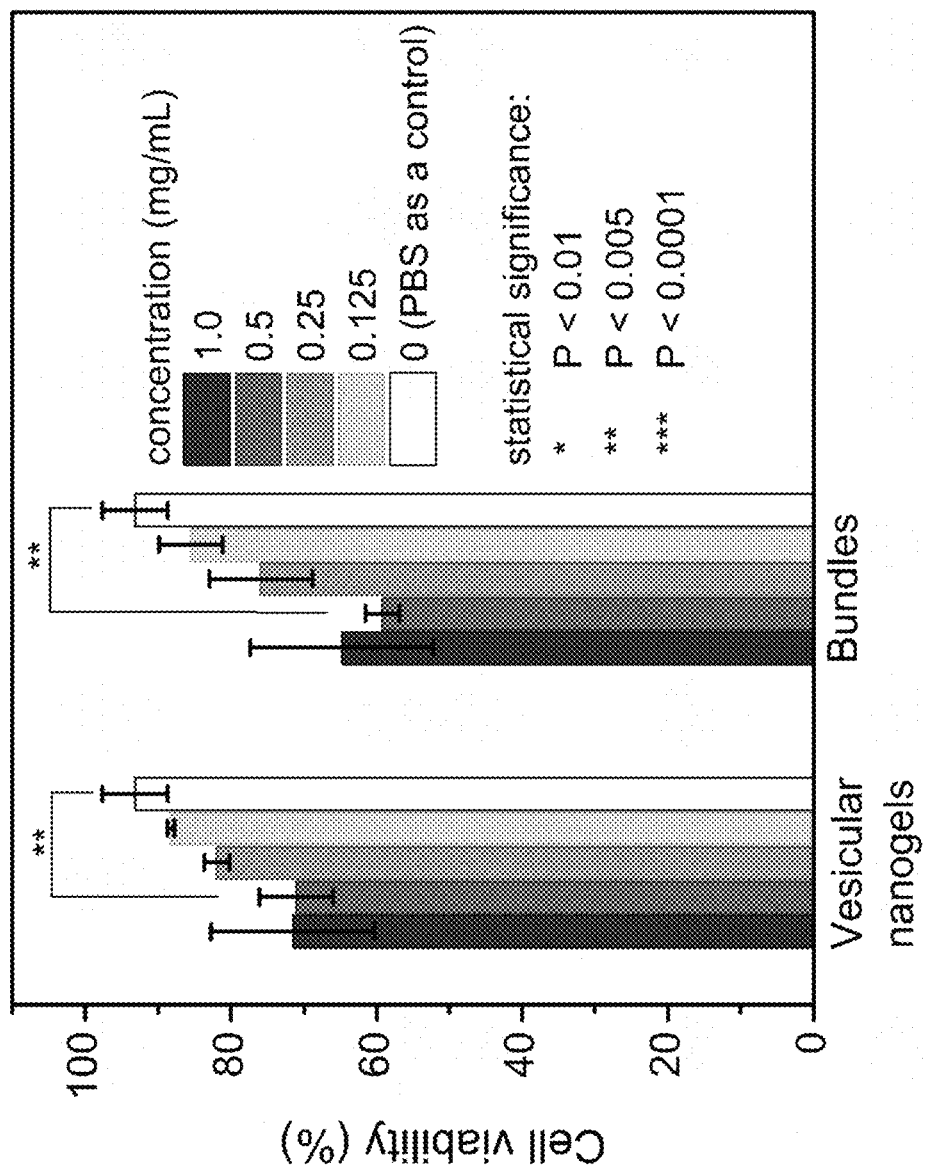
FIG. 31. Cytotoxicity of PPSU$_{20}$ nanogels. Flow cytometric-based toxicity assessment of PPSU$_{20}$ vesicular nanogels and bundles on RAW 264.7 cells for 24 h. Error bars represent the standard deviation from three parallel experiments.
Figure 32:
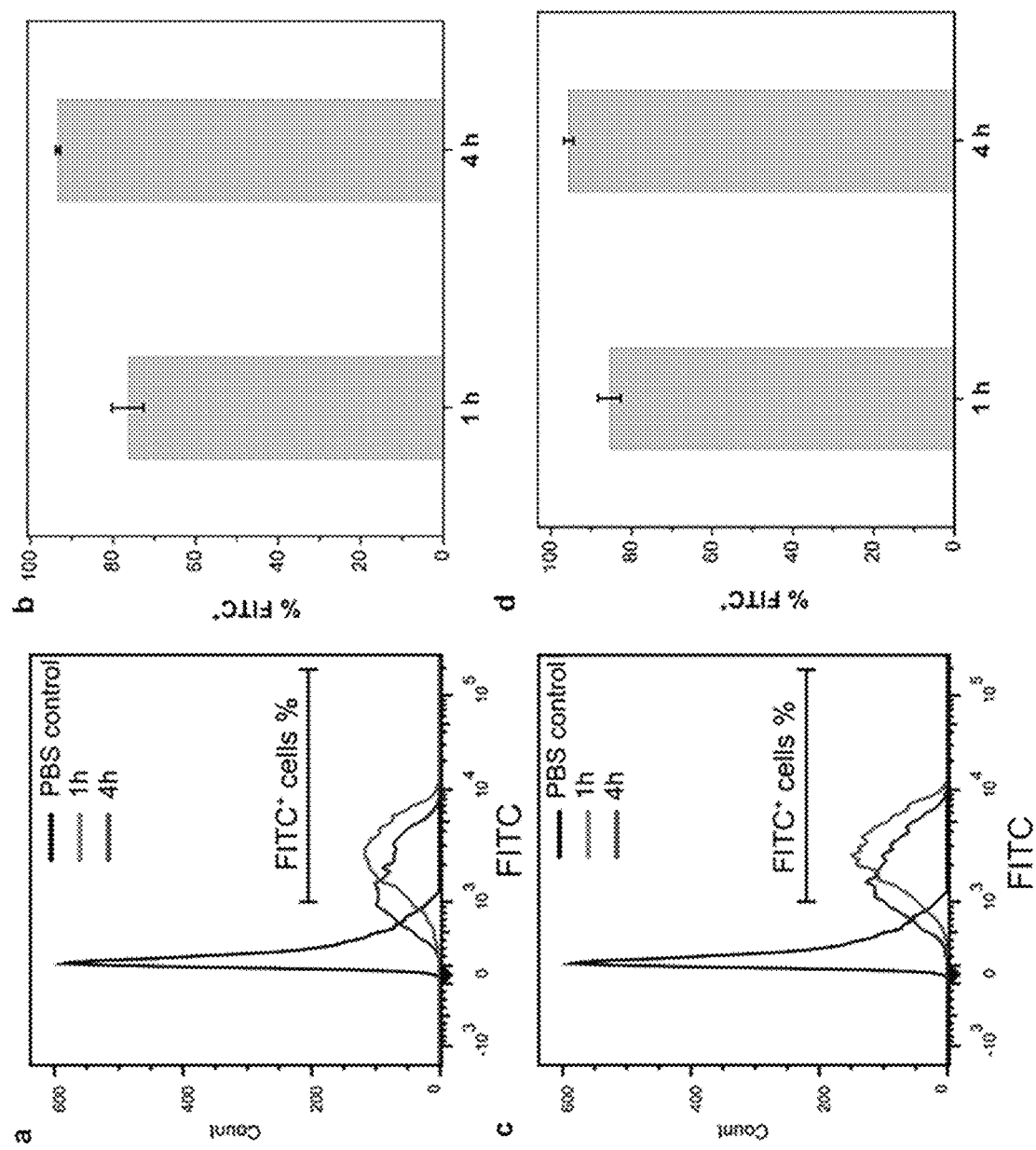
FIG. 32. Cellular uptake of PPSU$_{20}$ vesicular nanogels (a and b) and bundles (d and d) in RAW 264.7 cells. Nanogels were loaded with FITC-dextran, and incubated with cells for 1 h and 4 h. The percentage of FITC positive (% FITC+) cells is reported to indicate the extent of cellular uptake.
Figure 33:
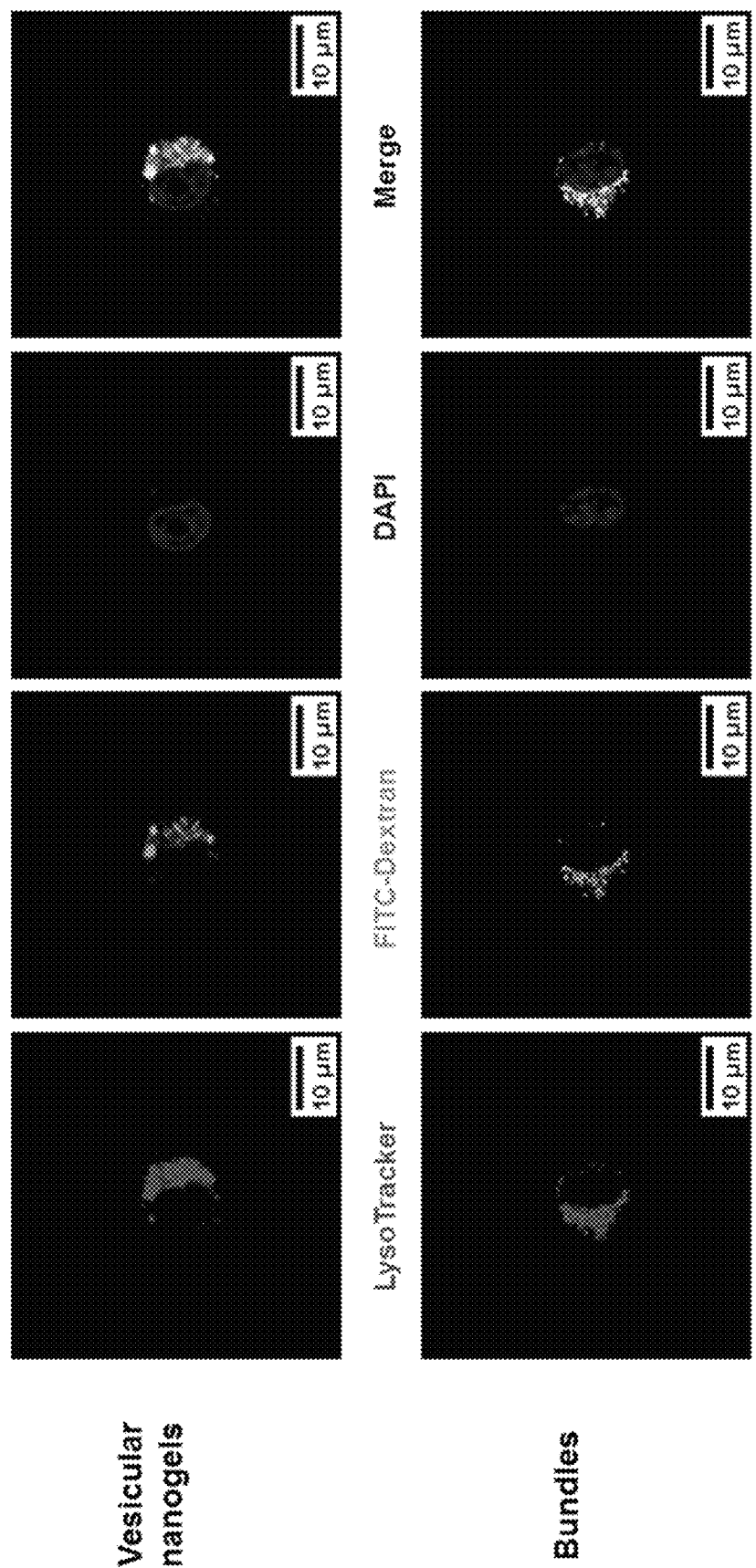
FIG. 33. Confocal fluorescence images of RAW 264.7 cells. Cells were incubated with FITC-dextran-loaded PPSU$_{20}$ nanogels for 4 h. Nuclei and endosomes/lysosomes were stained by DAPI and LysoTracker Red, respectively. Scale bar=10 µm.
Figure 34:
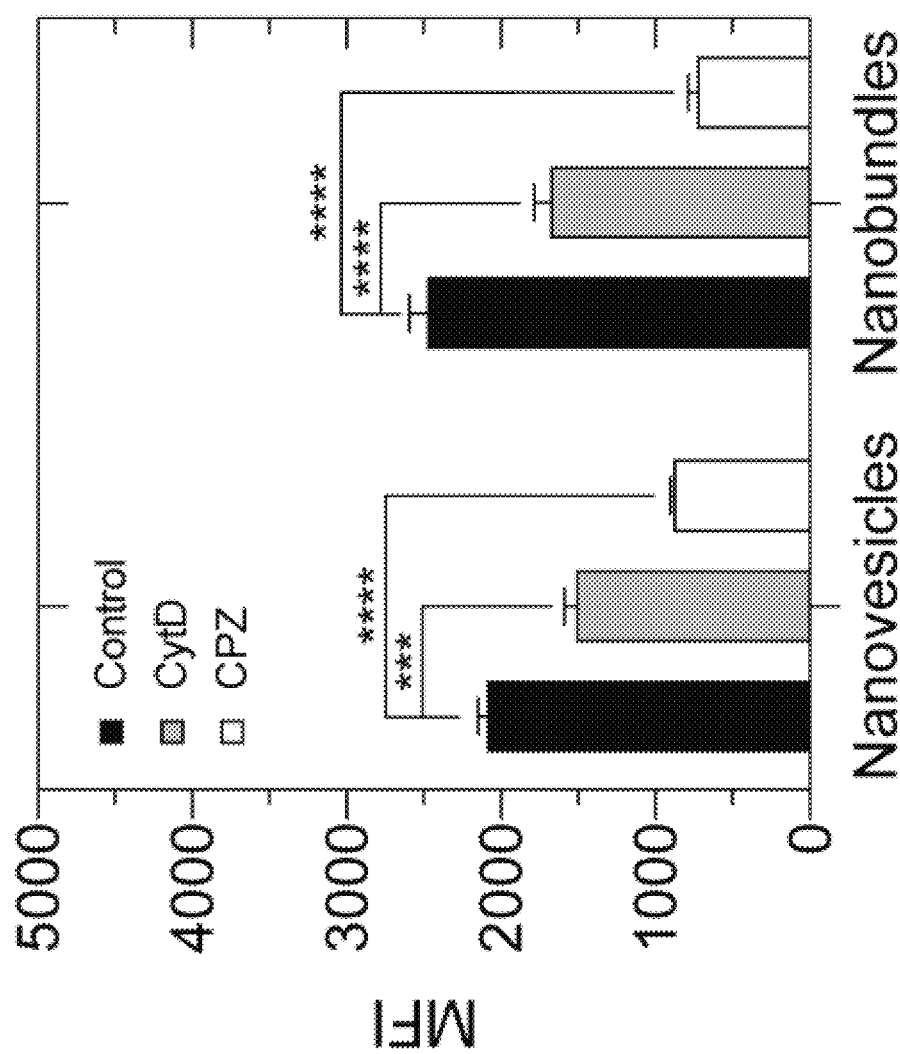
FIG. 34. Cells internalize PPSU$_{20}$ vesicular nanogels and bundles using macropinocytosis and clathrin-mediated endocytosis mechanisms. Statistically significant differences in nanostructure uptake in the absence (PBS pre-treated "Control") or presence of inhibitor (CytD or CPZ) was determined using Sidak's multiple comparisons test (*p<0.0005, **p<0.0001).

Our results demonstrate that sulfone-sulfone bonded networks have exceptional molecular capture capability, providing us with a new type of drug delivery platforms that would greatly enhance the ability to encapsulate drug molecules. Although there have been intensive studies on vesicle-based delivery in the past few decades, substantial challenges remain for polymeric nanocarriers due in part to their low loading of water-soluble biologics and hydrophilic small molecule therapeutics. Drug loading in these polymer vesicles (i.e. polymersomes) are lower than 20%; some are even substantially less than 5% (29). For their potential use in biomedical applications, we further demonstrated no cytotoxicity up to 0.25 mg/mL (FIGS. 30 and 31) and high cellular uptake (FIGS. 32 to 33) of $PPSU_{20}$ nanogels in macrophages, with intracellular delivery being mediated by both macropinocytosis and clathrin-mediated endocytosis mechanisms (FIG. 34). Macrophages were selected for the study due to their high phagocytic activity, allowing us to investigate both receptor mediated and receptor independent mechanisms of uptake. Furthermore, macrophages are the primary cells in the body responsible for clearance of nanoparticles due to their high prevalence in the liver and spleen.

In summary, we demonstrate that PPSU promotes the formation of an electrostatic network via sulfone-sulfone bonds in DMSO-water mixed systems. The sulfone-sulfone bonded network undergoes kinetically dependent self-assembly upon hydration, which imparts control over the morphology and size of macro- and nanoscale hydrogels. Without the need to change polymer structure or molecular weight, this single-component homopolymer system permits fabrication of crystalline frameworks and nanoscale hydrogels of spherical, vesicular, and cylindrical morphologies, controlled easily by the addition of water. The PPSU network shows a high affinity for a wide range of organic molecules, similar to the high-temperature solvent dimethyl sulfone. Taking advantage of this capability, we are able to encapsulate diverse hydrophilic molecules, including often difficult to load large biologics like protein and DNA, with nearly 100% efficiency. These results demonstrate that non-covalent sulfone-sulfone inter- and intra-chain bonding between PPSU homopolymers presents a structurally dynamic synthetic system that is biomimetic of natural biopolymers. PPSU is therefore a versatile platform for supramolecular chemistry with potential applications in biomedicine, diagnostics, catalysis and purification.

Methods

Polymer synthesis. $PPS_{20}$ was prepared by anionic ring-opening polymerization of propylene sulfide (20 equiv) using ethanethiol (1 equiv) initiator and benzyl bromide (5 equiv) end-capper in the presence of sodium methylate as a base in dry dimethyl formamide (30). Mixing $PPS_{20}$ with 30% of hydrogen peroxide (1 g $PPS_{20}$ per 100 mL of $H_2O_2$ solution) and shaking the mixtures led to a homogeneous solution overnight. Lyophilization of the obtained solution resulted in shiny solids of $PPSU_{20}$ without requirement for further purification.

AAMD simulations. Classical all-atom MD simulations were performed using the CHARMM 36m force field (31). The recommended CHARMM TIP3P water model (32) was applied with the structures constrained using the SETTLE algorithm (33). The simulations were performed using the package GROMACS (version 2016.3) (34). A detailed description of the simulation procedure is provided in the Supplementary Materials. The short-range electrostatic interactions were calculated up to 1.2 nm, and the long-range electrostatic interactions were calculated by means of the Particle Mesh Ewald algorithm (35). A time step of 2 fs (2.5 fs) was employed by constraining all the covalent bonds using the LINCS algorithm (36) in the DMSO system (water system). Annealing simulations were performed to speed up the convergence of the equilibrations (37).

Dipolar energy calculation. By following a previous work (38), we calculated the dipolar interactions between the neighbor units. Each sulfone is defined as one charge-neutral unit, as well as one DMSO molecule and one $H_2O$ molecule. The calculation of dipolar interaction energy between the charge-neutral units is provided in the Supplementary Materials. The average dipole moments were calculated to be 2.347 D for the CHARMM TIP3P water model, the same as the reported value of 2.347 D (39). The dipole moment of DMSO was calculated to be 5.22 D, in consistent with the reported value of 5.11 D in the original literature where the DMSO CHARMM force field were originally presented, and around 20% larger than the experimental value (40). The dipole moment was calculated to be 6.534 D for the sulfone.

Fabrication of nanostructured hydrogels of $PPSU_{20}$ with varied sizes and morphologies. 200 µL of $PPSU_{20}$ solutions (25 mg/mL in DMSO) were added stepwise with 400 µL of water and then one-time with another 400 µL of water. Each step was followed by vortexing to thoroughly mix the samples. After dialysis, the nanogels were applied for CryoTEM imaging, SAXS, DLS, WAXD, and MTT assay.

CGMD simulations. Each polymer is modeled by a linear bead-spring chain consisting of N=20 coarse-grained (CG) monomers. Each CG monomer carries three-point charges: a positive charge in the backbone corresponding to the S atoms and two neighboring backbone C atoms, and two negative charges corresponding to the O atoms (white spheres). Overall the monomer is charge neutral and has a net dipole as indicated by the all-atom model calculations. The relative positions of the three-point charges are maintained by harmonic springs between the S—O bonds and constraining the O—S—O angle. The non-bonded interactions between the CG monomers includes the excluded volume interaction and electrostatics. The excluded volume interaction is modeled by the Weeks-Chandler-Andersen potential, which is the Lennard-Jones potential truncated and shifted to zero at the minimum. The parameter is chosen as the length unit of the system, which corresponds to the van der Waals diameter of the S atom. The electrostatic interaction is truncated at the cutoff distance of $r_c=8\sigma$, which is considered adequate for our coarse-grained simulations where the solvent is treated implicitly as a uniform background with the dielectric constant of 47 for DMSO and 80 for water. The parameters of the CG model are calibrated against the all-atom in terms of the chain persistent length in these two solvents. To ensure that such a truncated Coulombic scheme does not affect our results, we have also performed test simulations with long-range Coulombic electrostatics with the particle-particle particle-mesh method. The simulations with long-range Coulombic electrostatics yield similar assembled morphologies. All the CGMD simulations were performed with the LAMMPS (version 19 Sep. 2019) software package (41).

Loading experiments. For the loading of Nile red, nanogels were prepared using pure water and Nile red-containing (0.1 mg/mL) DMSO solutions of $PPSU_{20}$. For the loading of water-soluble drugs, aqueous solutions of FITC (0.05 mg/mL), doxorubicin hydrochloride (1 mg/mL), dextran (1 mg/mL), albumin (various concentrations), GFP (0.2 mg/mL), RNA (0.2 mg/mL), DNA (0.2 mg/mL), and DMSO solutions of $PPSU_{20}$ (25 mg/mL) were used. Typically, 100 µL of the corresponding aqueous solution were mixed stepwise (10 µL/step or 100 µL/step) with 50 µL of $PPSU_{20}$ solution under vortex, then another 400 µL of water was added. After centrifugation at 16000×g for 10 min, fluorescence of the supernatant was measured and the encapsulation efficiencies were calculated.

Trypsin digestion of FITC-BSA-loaded $PPSU_{20}$ vesicular nanogels. DMSO solutions of $PPSU_{20}$ (200 µL, 25 mg/mL) were hydrated using 800 µL of aqueous FITC-BSA solutions (0, 0.1, 1.0, 10.0 mg/mL). DMSO was removed by dialysis after self-assembly. Negatively stained FITC-BSA-loaded $PPSU_{20}$ vesicular nanogels were characterized by TEM. After removal of unloaded FITC-BSA by three rounds of centrifugation and resuspension in phosphate-buffered saline, FITC-BSA-loaded $PPSU_{20}$ vesicular nanogels were subjected to digestion with trypsin protease (2 µg/mL; Trypsin Gold, Promega) for 24 h at 37° C., 80 rpm. Undigested FITC-BSA-loaded $PPSU_{20}$ vesicular nanogels (i.e. no protease treatment) were included as a control. After 24 h incubation with trypsin, FITC fluorescence ($E_x$=490 nm, $E_m$=525 nm) was quantified in triplicate using a SpectraMax M3 microplate reader (Molecular Devices). The percentage increase in FITC fluorescence (i.e., 100×(F(+)−F(−))/F(−)) after proteolysis was calculated, where F(+) is the fluorescence after protease treatment and F(−) is referred to the fluorescence in the absence of protease treatment.

REFERENCES EXAMPLE 1

1. Y. Bai, Q. Luo, J. Liu, Protein self-assembly via supramolecular strategies. *Chemical Society reviews* 45, 2756 (2016).
2. N. C. Seeman, H. F. Sleiman, DNA nanotechnology. *Nature Reviews Materials* 3, 17068 (2017).
3. W. B. Rogers, W. M. Shih, V. N. Manoharan, Using DNA to program the self-assembly of colloidal nanoparticles and microparticles. *Nature Reviews Materials* 1, 16008 (2016).
4. Y. Mai, A. Eisenberg, Self-assembly of block copolymers. *Chemical Society Reviews* 41, 5969 (2012).
5. L. Li, K. Raghupathi, C. Song, P. Prasad, S. Thayumanavan, Self-assembly of random copolymers. *Chemical communications* 50, 13417 (2014).
6. J. C. Foster, S. Varlas, B. Couturaud, Z. Coe, R. K. O'Reilly, Getting into Shape: Reflections on a New Generation of Cylindrical Nanostructures' Self-Assembly Using Polymer Building Blocks. *Journal of the American Chemical Society* 141, 2742 (2019).
7. Z. Tang, C. He, H. Tian, J. Ding, B. S. Hsiao, B. Chu, X. Chen, Polymeric nanostructured materials for biomedical applications. *Progress in Polymer Science* 60, 86 (2016).
8. D. Gorl, X. Zhang, V. Stepanenko, F. WUrthner, Supramolecular block copolymers by kinetically controlled co-self-assembly of planar and core-twisted perylene bisimides. *Nature Communications* 6, 7009 (2015).
9. S. Chen, W. H. Binder, Dynamic Ordering and Phase Segregation in Hydrogen-Bonded Polymers. *Accounts of Chemical Research* 49, 1409 (2016).
10. S. E. Boyken, Z. Chen, B. Groves, R. A. Langan, G. Oberdorfer, A. Ford, J. M. Gilmore, C. Xu, F. DiMaio, J. H. Pereira, B. Sankaran, G. Seelig, P. H. Zwart, D. Baker, De novo design of protein homo-oligomers with modular hydrogen-bond network-mediated specificity. *Science* 352, 680 (2016).
11. R. J. Wojtecki, M. A. Meador, S. J. Rowan, Using the dynamic bond to access macroscopically responsive structurally dynamic polymers. *Nature materials* 10, 14 (2011).
12. C. G. Pappas, R. Shafi, I. R. Sasselli, H. Siccardi, T. Wang, V. Narang, R. Abzalimov, N. Wijerathne, R. V. Ulijn, Dynamic peptide libraries for the discovery of supramolecular nanomaterials. *Nature Nanotechnology* 11, 960 (2016).
13. F. Zhang, J. Nangreave, Y. Liu, H. Yan, Structural DNA Nanotechnology: State of the Art and Future Perspective. *Journal of the American Chemical Society* 136, 11198 (2014).
14. A. Napoli, M. Valentini, N. Tirelli, M. Muller, J. A. Hubbell, Oxidation-responsive polymeric vesicles. *Nature materials* 3, 183 (2004).
15. New Synthetic Methodologies for Amphiphilic Multiblock Copolymers of Ethylene Glycol and Propylene Sulfide. *Macromolecules* 34, 8913 (2001).
16. N. B. Karabin, S. Allen, H.-K. Kwon, S. Bobbala, E. Firlar, T. Shokuhfar, K. R. Shull, E. A. Scott, Sustained micellar delivery via inducible transitions in nanostructure morphology. *Nature Communications* 9, 624 (2018).
17. F. Du, Y.-G. Liu, E. A. Scott, Immunotheranostic Polymersomes Modularly Assembled from Tetrablock and Diblock Copolymers with Oxidation-Responsive Fluorescence. *Cellular and Molecular Bioengineering* 10, 357 (2017).
18. F. Du, S. Bobbala, S. Yi, E. A. Scott, Sequential intracellular release of water-soluble cargos from Shell-crosslinked polymersomes. *Journal of Controlled Release* 282, 90 (2018).
19. A. E. Vasdekis, E. A. Scott, C. P. O'Neil, D. Psaltis, J. A. Hubbell, Precision Intracellular Delivery Based on Optofluidic Polymersome Rupture. *ACS Nano* 6, 7850 (2012).
20. W. Yu, X. He, K. Vanommeslaeghe, A. D. MacKerell Jr, Extension of the CHARMM general force field to sulfonyl-containing compounds and its utility in biomolecular simulations. *Journal of Computational Chemistry* 33, 2451 (2012).
21. F. G. Bordwell, G. D. Cooper, The Effect of the Sulfonyl Group on the Nucleophilic Displacement of Halogen in a-Halo Sulfones and Related Substances1. *Journal of the American Chemical Society* 73, 5184 (1951).
22. T. Clark, J. S. Murray, P. Lane, P. Politzer, Why are dimethyl sulfoxide and dimethyl sulfone such good solvents? *Journal of Molecular Modeling* 14, 689 (2008).
23. A. B. Lowe, C. L. McCormick, Synthesis and Solution Properties of Zwitterionic Polymers. *Chemical Reviews* 102, 4177 (2002).
24. P. Teng, Z. Niu, F. She, M. Zhou, P. Sang, G. M. Gray, G. Verma, L. Wojtas, A. van der Vaart, S. Ma, J. Cai, Hydrogen-Bonding-Driven 3D Supramolecular Assembly of Peptidomimetic Zipper. *J. Am. Chem. Soc.* 140, 5661 (2018).
25. R. Freeman, M. Han, Z. Alvarez, J. A. Lewis, J. R. Wester, N. Stephanopoulos, M. T. McClendon, C. Lynsky, J. M. Godbe, H. Sangji, E. Luijten, S. I. Stupp, Reversible self-assembly of superstructured networks. *Science* 362, 808 (2018).
26. J. B. Gilroy, T. Gadt, G. R. Whittell, L. Chabanne, J. M. Mitchels, R. M. Richardson, M. A. Winnik, I. Manners, 26. Monodisperse cylindrical micelles by crystallization-driven living self-assembly. *Nature Chemistry* 2, 566 (2010).
27. I. Choi, S. Yang, T.-L. Choi, Preparing Semiconducting Nanoribbons with Tunable Length and Width via Crystallization-Driven Self-Assembly of a Simple Conjugated Homopolymer. *Journal of the American Chemical Society* 140, 17218 (2018).
28. C. E. Castro, H.-J. Su, A. E. Marras, L. Zhou, J. Johnson, Mechanical design of DNA nanostructures. *Nanoscale* 7, 5913 (2015).
29. S. Allen, O. Osorio, Y.-G. Liu, E. Scott, Facile assembly and loading of theranostic polymersomes via multi-impingement flash nanoprecipitation. *Journal of Controlled Release* 262, 91 (2017).
30. S. Cerritelli, D. Velluto, J. A. Hubbell, PEG-SS-PPS: Reduction-Sensitive Disulfide Block Copolymer Vesicles for Intracellular Drug Delivery. *Biomacromolecules* 8, 1966 (2007).
31. J. Huang, S. Rauscher, G. Nawrocki, T. Ran, M. Feig, B. L. de Groot, H. Grubmüller, A. D. MacKerell Jr, CHARMM36m: an improved force field for folded and intrinsically disordered proteins. *Nature methods* 14, 71 (2016).
32. A. D. MacKerell, D. Bashford, M. Bellott, R. L. Dunbrack, J. D. Evanseck, M. J. Field, S. Fischer, J. Gao, H. Guo, S. Ha, D. Joseph-McCarthy, L. Kuchnir, K. Kuczera, F. T. K. Lau, C. Mottos, S. Michnick, T. Ngo, D. T. Nguyen, B. Prodhom, W. E. Reiher, B. Roux, M. Schlenkrich, J. C. Smith, R. Stote, J. Straub, M. Watanabe, J. Wiórkiewicz-Kuczera, D. Yin, M. Karplus, All-Atom Empirical Potential for Molecular Modeling and Dynamics Studies of Proteins. *The Journal of Physical Chemistry B* 102, 3586 (1998).
33. S. Miyamoto, P. A. Kollman, Settle: An analytical version of the SHAKE and RATTLE algorithm for rigid water models. *Journal of Computational Chemistry* 13, 952 (1992).
34. B. Hess, C. Kutzner, D. van der Spoel, E. Lindahl, GROMACS 4: Algorithms for Highly Efficient, Load-Balanced, and Scalable Molecular Simulation. *Journal of Chemical Theory and Computation* 4, 435 (2008).
35. U. Essmann, L. Perera, M. L. Berkowitz, T. Darden, H. Lee, L. G. Pedersen, A smooth particle mesh Ewald method. *The Journal of Chemical Physics* 103, 8577 (1995).
36. B. Hess, P-LINCS: A Parallel Linear Constraint Solver for Molecular Simulation. *Journal of Chemical Theory and Computation* 4, 116 (2008).
37. J. H. Ortony, B. Qiao, C. J. Newcomb, T. J. Keller, L. C. Palmer, E. Deiss-Yehiely, M. Olvera de la Cruz, S. Han, S. I. Stupp, Water Dynamics from the Surface to the Interior of a Supramolecular Nanostructure. *Journal of the American Chemical Society* 139, 8915 (2017).
38. B. Qiao, G. Ferru, M. Olvera de la Cruz, R. J. Ellis, Molecular Origins of Mesoscale Ordering in a Metalloamphiphile Phase. *ACS Central Science* 1, 493 (2015).
39. P. Mark, L. Nilsson, Structure and Dynamics of the TIP3P, SPC, and SPC/E Water Models at 298 K. *The Journal of Physical Chemistry A* 105, 9954 (2001).
40. M. L. Strader, S. E. Feller, A Flexible All-Atom Model of Dimethyl Sulfoxide for Molecular Dynamics Simulations. *The Journal of Physical Chemistry A* 106, 1074 (2002).
41. S. Plimpton, Fast Parallel Algorithms for Short-Range Molecular Dynamics. *Journal of Computational Physics* 117, 1 (1995).

Materials and Methods

Chemical Reagents

All chemical reagents were purchased from Sigma-Aldrich St. Louis, Mo., USA, unless stated otherwise. Recombinant *A. victoria* GFP protein (from the Jewett Lab), FITC-RNA and FITC-DNA conjugates (from the Mirkin Lab) were obtained as generous gifts from other Labs at Northwestern University.

Polymer Synthesis

PPSU was synthesized from complete oxidation of the corresponding PPS. Mixing PPS with 30% of hydrogen peroxide (1 g PPS per 100 mL of $H_2O_2$ solution) and shaking the mixtures led to a homogeneous solution overnight. Lyophilization of the obtained solution resulted in white shiny solids of PPSU without requirement for further purification. It is worthwhile to note that an oxidation intermediate (sulfone/sulfoxide mixtures) can be collected by precipitation the homogeneous solution in THF. Apparent differences were discovered for $PPSU_{20}$ and the random copolymers of sulfoxides and sulfones. First, $PPSU_{20}$ powders are demonstrated by WAXD to be crystalline while the sulfoxides/sulfone mixtures are mostly amorphous. Second, the sulfoxides/sulfone mixtures are readily dissolved by water while $PPSU_{20}$ solids are completely insoluble in water.

All-Atom Explicit Solvent Molecular Dynamics Simulations

Classical all-atom molecular dynamics simulations were performed using the CHARMM 36m force field (31). The recommended CHARMM TIP3P water model (32) was applied with the structures constrained using the SETTLE algorithm (33). The simulations were performed using the package GROMACS (version 2016.3) (34). In all the simulations, the degree of polymerization (DP) of 20 was employed for the polymer chains, the same as that $PPSU_{20}$ in the experiments. The polymer chains were created in the extended form. Six extended $PPSU_{20}$ chains were randomly dissolved in each of the three water boxes initially. Whereas in the DMSO systems, the initially extended $PPSU_{20}$ chains were equilibrated in a vacuum, forming coiled configurations, and were then dissolved in the DMSO boxes. The initial configurations are provided in FIG. 7. See Table 3 for the components of the systems. For both solvent conditions, three parallel simulations were performed.

The system potential energy was first minimized using the steepest descent algorithm, followed by the equilibration of 1 ps in the NVT ensemble (constant number of particles, volume and temperature). Subsequently the NPT ensemble (constant number of particles, pressure and temperature) was applied. An equilibration of 10 ps using the time step of 1 fs was followed by another equilibration of 0.1 ns using a time step of 2 fs in the DMSO system, or 2.5 fs in the aqueous system. Subsequently long equilibration simulations were performed. The periodic boundary conditions were applied in all three dimensions. The neighbor searching was performed up to a cut-off distance of 1.2 nm by means of the Verlet particle-based approach and was updated every 20 time steps. The potential-switch method was applied for the short-range Lennard-Jones (LJ) 12-6 interactions from 1 nm to 1.2 nm. The short-range electrostatic interactions were calculated up to 1.2 nm, and the long-range electrostatic interactions were calculated by means of the Particle Mesh Ewald algorithm (35). A time step of 2 fs (2.5 fs) was employed by constraining all the covalent bonds using the LINCS algorithm (36) in the DMSO system (water system). The temperatures of the $PPSU_{20}$ solute and the solvent molecules were separately coupled using the Nose-Hover algorithm (reference temperature 298 K, characteristic time 1 ps). The isotropic Parrinello-Rahman barostat was utilized with the reference pressure of 1 bar, the characteristic time 4 ps and the compressibility 4.5×10$^{-5}$ bar$^{-1}$. Each of the simulations run 200 ns, with the last 50 ns employed for the data collection and analysis. The final simulation snapshots are presented in FIG. 7. The convergence of the simulations was justified by the calculations of the potential energies and the sizes of the polymer chains, both as a function of the simulation time. The polymer structures were calculated using the end-to-end distance and the persistence length.

Additionally, control simulations were performed. In the control simulations, initially extended polymer chains were employed for both DMSO and water solvent systems. The annealing simulations were performed to speed up the convergence of the equilibrations (37). In the annealing simulations, the temperatures of polymer and solvent (DMSO or water) were separately coupled. The temperatures started at 298 K initially, which increased to 353 K within 1 ns. They stayed at 353 K for 9 ns, then dropped to 298 K within 1 ns. Finally, the temperatures stayed at 298 K for another 9 ns. Therefore, each annealing cycle lasted 20 ns. 5 annealing cycles were performed for the DMSO systems (100 ns in total), and 8 cycles (160 ns in total) for the water systems. Subsequently, the production simulations were performed for 40 ns each. Agreements were found in regards with the polymer chain distribution (molecularly dissolved in DMSO and aggregated in water), the polymer structures (end-to-end distance and persistence length) and the radial distribution function of the polymer sulfur atoms.

Calculation of the dipolar energy between neighbor charge-neutral units from atomistic molecular dynamics simulations In all the atomistic simulations, the PPSU repeat units and the solvent (DMSO or water) molecules are charge-neutral. The monopole interactions between them could be reasonably expected negligible. By following a previous work (38), we calculated the dipolar interactions between the neighbor units. Each PPSU repeat unit is defined as one charge-neutral unit, as well as one DMSO molecule and one H$_2$O molecule. The dipolar interaction energy between the charge-neutral units is calculated as below:

1) The sulfur atoms of PPSU repeat units, the sulfur atoms of DMSO and the oxygen atoms of water molecules are employed as the center of the corresponding units. The radial distribution functions between these atoms are calculated (FIG. 12). Note that for the S(PPSU)-S(PPSU) calculations all the intramolecular correlations within 5 consecutive repeat units were excluded based on the calculated persistence of 4.4 repeating units in water (Table 4). The first minima were chosen to define the upper distance of the neighbors, which was 6.7 Å for S(PPSU)-S(PPSU), 7.1 Å S(PPSU)-S(DMSO) and 5.3 Å S(PPSU)-O(H$_2$O).

2) The dipole moment of PPSU repeat units, DMSO molecules and water molecule were calculated via $$\vec{\mu} \Sigma_i [(\vec{x_i} - \vec{x}_{center}) \cdot q_i]. \tag{S1}$$

$\vec{x_i}$ denotes the coordinate of atom i with the atomic partial charge $q_i$. $\vec{x}_{center}$ stands for the coordinate of the center atom of S(PPSU), S(DMSO) or O(H$_2$O). The average dipole moments were calculated to be 2.347 D for the CHARMM TIP3P water model, the same as the reported value of 2.347 D (39). The dipole moment of DMSO was calculated to be 5.22 D, in consistent with the reported value of 5.11 D in the original literature where the DMSO CHARMM force field were originally presented, and around 20% larger than the experimental value (40). The dipole moment was calculated to be 6.534 D for PPSU repeat units.

3) The dipolar interaction energy between units i and j could be thus obtained by $$U = \frac{1}{4\pi\varepsilon_0 r^3}[\vec{\mu_i} * \vec{\mu_j} - 3(\vec{\mu_i} * \hat{r})(\vec{\mu_j} * \hat{r})], \tag{S2}$$

where $\vec{\mu_i}$, $\vec{\mu_j}$ is the dipole moment of units i and j, respectively; $\hat{r}$ stands for the unit vector between the centers of the two units. Here the units refer to PPSU repeat units, DMSO molecules and water molecules. The cutoff distances were defined in step 1.

4) The steps 2 to 3 were performed for all the dipole-dipole interactions of PPSU-PPSU and PPSU-DMSO in the DMSO solution, and PPSU-PPSU and PPSU-water in the aqueous solution. The distribution of the calculated dipolar energies is provided in FIG. 10.

Humidity induced-aggregation for DMSO solutions of PPSU$_{20}$

DMSO solutions of PPSU$_{20}$ were exposed to humidity in air and the phase transition was tracked. Sol-to-gel phase transition was observed for a highly concentrated solution (200 mg/mL) overnight and a low concentration solution (25 mg/mL) became cloudy in 3 days. As the cloudy solution was allowed to age further (110 days), fluffy precipitates (can be observed in 7 days) were obtained by centrifugation. The fluffy precipitates were demonstrated by WAXD to be mostly amorphous (FIG. 13). After dispersing in water, these fluffy precipitates were recollected by centrifugation. In samples treated this way, WAXD showed an increased crystallinity in FIG. 13.

CryoTEM Imaging

Samples were prepared by applying 3 μL of sample (5 mg/mL) on pretreated holey or lacey carbon 400 mesh TEM copper grids (Electron Microscopy Sciences). Following a 3 s blot, samples were plunge-frozen (Gatan Cryoplunge 3 freezer). Images of samples entrapped in vitreous ice were acquired using a field emission transmission electron microscope (JEOL 3200FS) operating at 300 keV with magnification ranging from 2000× to 12,000× nominal magnification. Digital Micrograph software (Gatan) was used to align the individual frames of each micrograph to compensate for stage and beam-induced drift. Any further image processing conducted on the aligned frames was completed in ImageJ.

SAXS Measurements

SAXS measurements were performed at the DuPont-Northwestern-Dow Collaborative Access Team (DND-CAT) beamline at Argonne National Laboratory's Advanced Photon Source (Argonne, IL, USA) with 10 keV (wavelength λ=1.24 Å) collimated X-rays. All the samples (5 mg/mL) were analyzed in the q-range (0.001-0.5 Å$^{-1}$), with a sample-to-detector distance of approximately 7.5 m and an exposure time of 1 s. The diffraction patterns of silver behenate were utilized to calibrate the q-range. The momentum transfer vector q is defined as q=4π(sin θ/λ, where θ is the scattering angle. Data reduction, consisting of the removal of solvent/buffer scattering from the acquired sample scattering, was completed using PRIMUS 2.8.2 software while model fitting was completed using SasView 4.0.1 software package. The core-shell cylinder, vesicle and core-shell sphere models were utilized to analyze the data.

Transmission electron microscopy of negatively stained PPSU$_{20}$ structures 1.5% uranyl formate (UF) was prepared in ultrapure water. The pH was adjusted to 4.5 by addition of 10 N KOH. 4 µL of nanostructures were applied to glow discharged (25 W, 10 s) formvar carbon film copper grids (400 mesh; Electron Microscopy Sciences, Inc.). Samples were gently washed twice via passage through ultrapure water, and were negatively stained by passage through two 30 µL volumes of 1.5% UF. Excess stained was removed by blotting each sample with Whatman filter paper. After this procedure, ~0.5 µL stain remains on the grid with an activity of 2.55×10$^{-5}$ µCi/grid. Images were acquired at 30,000× on a JOEL 1400 Transmission Electron Microscope operating at 120 kV.

Energy Dispersive X-Ray Spectroscopy

1 µL of PPSU$_{20}$ nanobundles (5 mg/mL in water) were mixed thoroughly with 1 µL of 2% methyl cellulose and 3 µL of water. 5 µL of the mixture was deposited on Formvar/Carbon 200 Mesh Copper TEM grids from Electron Microscopy Sciences that were glow discharged to create a hydrophilic surface. After resting for 15 s, the grid was incubated in 1.5% UF for 15 s. Excess stain was wicked away with filter paper. Scanning transmission electron microscopy images were taken with high angle annular dark field (HAADF) mode where bright contrast is indicative of a species with a higher atomic number. In this case, uranium from UF provides the contrast, and the absence of that contrast shows the structure of the embedded sample. EDS maps were taken on a Hitachi HD-2300A dedicated STEM equipped with dual EDS detectors and Thermo Fischer Scientific NSS software. Operating at 200 kV with a 58 µA emission current and an aperture with 75 µm diameter, 90 frames of a 512×384 pixel EDS map were collected in EDX Mode. The overall frame time was 10 s with a pixel dwell time of 50 µs. Data was processed by binning with a 17×17 kernel size.

Adsorption of FITC-BSA by Preformed PPSU$_{20}$ Vesicular Nanogels

PPSU$_{20}$ vesicular nanogels were prepared by mixing 100 µL of water or 100 µL of aqueous FITC-BSA (1.0 mg/mL) solution with 100 µL of PPSU$_{20}$ solution (25 mg/mL in DMSO) under vortex, followed by the addition of 1000 µL of water. Nanogels were collected by centrifugation and purified by 2 rounds of resuspension and centrifugation in 1000 µL of water. The preformed blank vesicular nanogels were further incubated with 100 µL of aqueous FITC-BSA (1.0 mg/mL) solution overnight, giving FITC-BSA-adsorbed nanogels after removal of free FITC-BSA by three rounds of centrifugation and resuspension in water. Blank nanogels, FITC-BSA-loaded nanogels, and FITC-BSA-adsorbed nanogels were resuspended in 1000 µL of water for fluorescence measurements or as the stocking solutions for fluorescence quantitative analysis in sodium hydroxide solution (0.2 N).

Cell Experiments

RAW 264.7 cells (murine macrophage cell line) were acquired from American Type Culture Collection (ATCC, Rockville, Md., USA) and used for cell culture experiments. This cell line was cultured in Dulbecco's Modified Eagle's Medium (DMEM) supplemented with 10% fetal bovine serum (FBS), penicillin (100 IU/mL) and streptomycin (100 µg/mL) at 37° C. with CO$_2$ (5%).

Cell viability: Both MTT assay and flow cytometric assessment were performed to investigate cell viability upon nanostructures treatment. In MTT assay, RAW 264.7 cells (3×10$^5$ cells/mL, 100 µL) were plated in each well of a 96-well plate and left overnight in the incubator for adherence. The adhered cells were treated with different concentrations of PPSU$_{20}$ nanogels (1, 0.5, 0.25 and 0.125 mg/mL). After incubation for 24 h, all wells were added with MTT (5 mg/mL in PBS, 10 µL) and further incubated for 4 h. The resultant formazan crystal deposition in each well was dissolved in DMSO (200 µL) and the absorbance was measured at 560 nm. All the samples were analyzed in quadruplicates. The percentage cell viability was calculated as: % cell viability=(OD of treated sample/OD of untreated sample)×100. Macrophage cell viability following nanostructure treatment was also determined using Zombie Aqua fixable cell viability dye. Following differentiation, cells were plated at 2.5×10$^5$ cells/mL (200 µL; 50,000 cells/well) in 96-well tissue culture treated plates in DMEM cell culture media. RAW 264.7 cells received matched volume treatments of either PBS or PPSU$_{20}$ nanostructures (bundle-like or vesicle like nanostructures with concentrations of 1, 0.5, 0.25 and 0.125 mg/mL). After incubation for 24 h, cells were collected and transferred to 1.2 mL microtiter tubes prior to staining with Zombie Aqua fixable viability dye (Biolegend) for 15 min. Cells were washed with cell staining buffer and fixed with intracellular (IC) cell fixation buffer (Biosciences). Flow cytometry data was acquired on an LSR Fortessa analyzer (BD Biosciences) and analyzed using FlowJo.

Cellular uptake studies: RAW 264.7 cells (2.5×10$^5$ cells/mL, 400 µL) were seeded in each well of a 48-well plate and left overnight in the incubator for adherence. The adhered cells were treated with 0.25 mg/mL of FITC-dextran-loaded PPSU$_{20}$ nanogels (bundle or vesicular morphology) and incubated for 1 h or 4 h. Cells were washed two times with PBS and incubated with 50 µL Zombie Aqua (1:100) fixable cell viability dye diluted in cell staining buffer for 15 min at 4° C. Then the cells were washed with 500 µL PBS, resuspended in cell staining buffer and immediately analyzed using a BD Fortessa flow cytometer. The cellular uptake was measured as % of FITC positive cells.

Analysis/imaging of cells: RAW 264.7 cells (1×10$^5$ cells/mL, 300 µL) were seeded in each well of an 8-well Chamber slide (Thermo Fischer Scientific) and left overnight in the incubator for adherence. The adhered cells were treated with 0.25 mg/mL of FITC-dextran-loaded PPSU$_{20}$ nanostructures (bundle or vesicular morphology). After incubation for 4 h, cells were washed two times with PBS and incubated with LysoTracker™ Red DND-99 (1:5000 dilution, 300 µL DMEM) for 30 min. Then the cells were washed twice with PBS, added with 300 µL PBS and incubated with NucBlue™ Live ReadyProbes™ Reagent (nuclei stain, 1 drop) for 15 min in the dark. Images were acquired on a Leica TCS SP8 confocal microscope with a 63× oil immersion objective.

Investigation of cellular uptake mechanisms: RAW 264.7 macrophages were pre-treated with either cytochalasin D (5 µM; Cayman Chemical) for 2 h to inhibit macropinocytosis, or chlorpromazine (100 µM; Chlorpromazine HCl, Sigma Aldrich) for 30 min to inhibit clathrin-dependent endocytosis. PBS-treated cells were included as a control in these experiments. After this pre-treatment period, cells were incubated with 0.25 mg/mL FITC-dextran-loaded PPSU$_{20}$ vesicular nanogels or nanobundles, and flow cytometry was performed. The median fluorescence intensity (MFI) was used to quantify the cellular internalization of PPSU$_{20}$ nanogels and bundles. Sidak's multiple comparisons test was used to determine whether inhibitor pre-treatment significantly reduced the cellular uptake of PPSU$_{20}$ nanostructures compared to PBS-treated control. In these experiments, a statistically significant reduction in nanostructure uptake indicates the inhibited endocytosis pathway contributes to internalization.

MATERIALS AND METHODS REFERENCES (S1) B. Qiao, K. C. Littrell, R. J. Ellis, Phys. Chem. Chem. Phys. 20, 12908-12915.

(S2) C. Reichardt, "Solvents and Solvent Effects in Organic Chemistry" (Wiley-VCH Publishers, 3rd ed., 2003).

Example 2

Develop Universal Molecular Encapsulation by PPSU as a Tool for the Optimization of a Model.

We present two novel encapsulation methods uniquely achievable by PPSU. First, collapsible networks of PPSU can encapsulate >4 payloads simultaneously, each at a controllable concentration (FIG. 36), but requires exposure of the payload to DMSO. This pre-assembly (FIG. 35A) method could be highly advantageous for the rapid loading and fabrication of stable formulations that include proteins insensitive to DMSO exposure, like Th1-biased vaccine formulations (protein antigen structure does not need to be retained for MHC-I presentation). The second method involves post-assembly (FIG. 35A) loading of payloads, wherein incubation of PPSU nanostructures with water soluble payloads in aqueous solutions results in their stable collection and retention within PPSU NBM at nearly 100% encapsulation efficiency. Enzymes encapsulated using this second method retained their activity (FIG. 35B-D). The ease and versatility of PPSU assembly into drug-loaded NBMs can allow optimization and customization for diverse multi-component or theranostic formulations, as well as present novel methods of filtration or purification of biological fluids.

Figure 35:
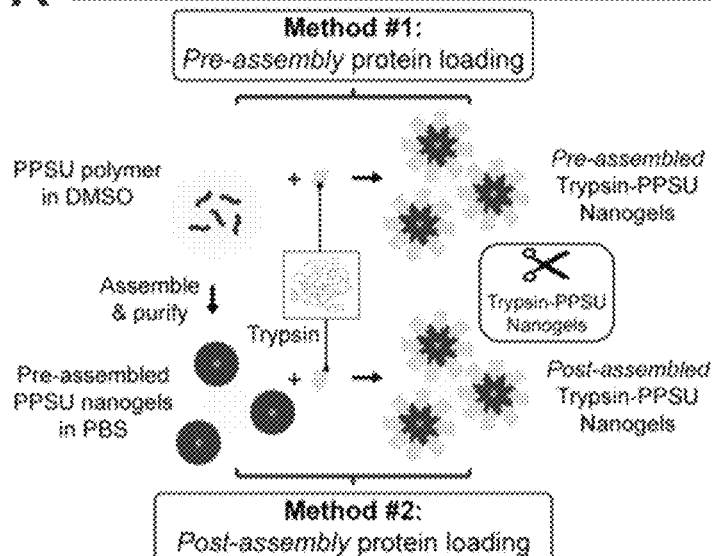
FIG. 35. Loading PPSU nanogels with trypsin after assembly forms stable Trypsin-PPSU nanogels and retains Trypsin bioactivity. (A) Trypsin-PPSU nanogels were formed using two distinct methods. In Method #1 (Pre-assembly protein loading), Trypsin was added to PPSU polymer at the time of assembly. In Method #2 (Post-assembly protein loading), Trypsin was added to pre-formed PPSU nanogels. (B) Proteins (FITC-BSA shown here in an eppendorf tube as an example) like trypsin are stably loaded into PPSU nanogels using method #2 simply by mixing and shaking for 5 min. Trypsin loaded nangels were stored at 4° C. for 48 h prior to centrifugation and subsequent analysis of supernatant. While free form trypsin (~23.1 kDa) was readily detected by MALDI-TOF-MS, no released trypsin was detected in nanogel supernatants. (C) Illustration of fluorescence-based proteolysis kinetic assay used to detect trypsin activity. (D) Trypsin-PPSU prepared using the post-assembly method retains trypsin bioactivity. Lowered trypsin activity is likely due to decreased diffusion rate and lower probability of interactions with FITC-BSA when trypsin is embedded in the larger Trypsin-PPSU NBMs. Free trypsin was not detectable in the supernatant.
Figure 35:
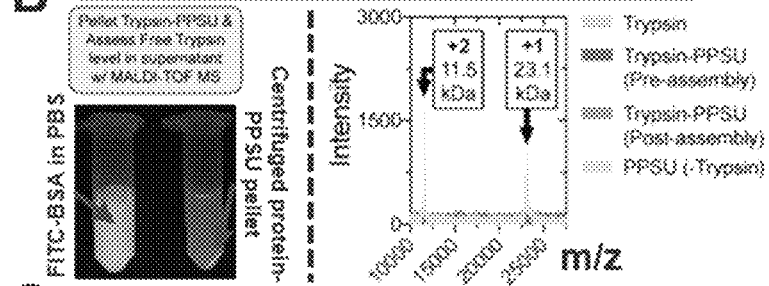
Figure 35:
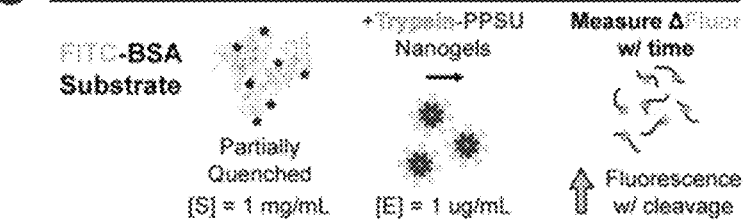
Figure 35:
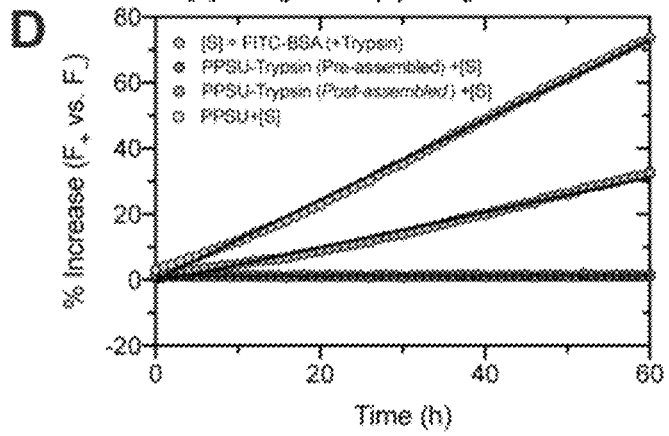
Figure 36:
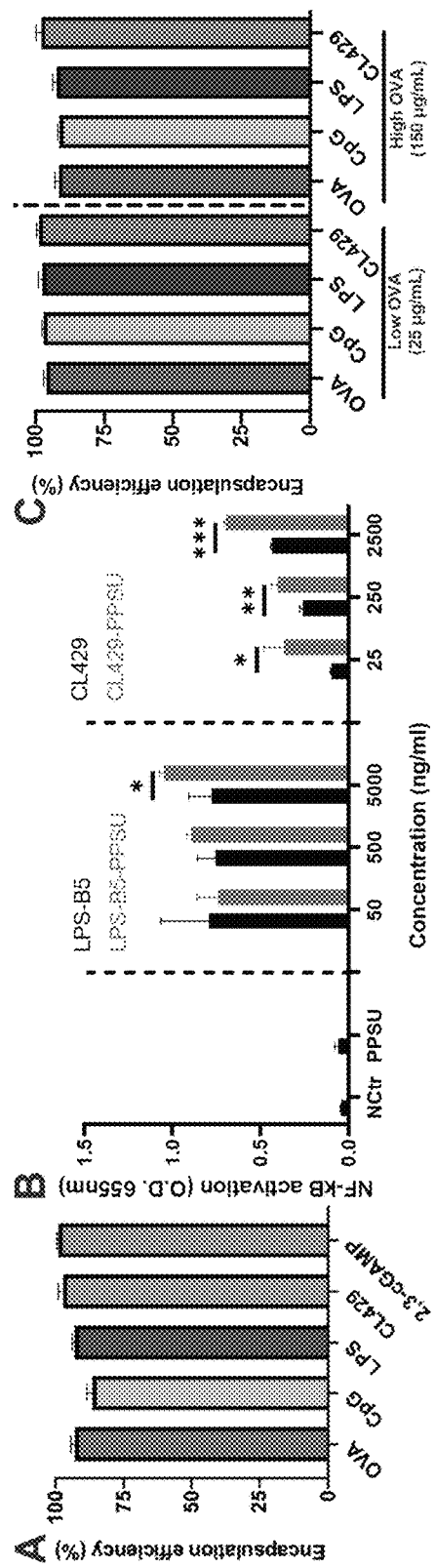
FIG. 36. PPSU allows reproducible, high encapsulation efficiency for diverse vaccine payloads and can enhance adjuvancy. (A) 5 physicochemically distinct molecules relevant to vaccine formulations were loaded individually into PPSU nanogel vesicles. Components and their methods of detection are described in Table 2. >90% encapsulation efficiency was reproducibly achieved for each payload. (B) While PPSU alone demonstrated no effect on RAW-blue macrophages, activation of NF-kB by adjuvants loaded within PPSU nanogels were either equally effective (LPS) or enhanced (CL429) compared to free form drug. (C) As a model synthetic subunit vaccine formulation, 1 antigen and 3 model adjuvants were co-loaded into PPSU nanogel vesicles simultaneously to mimic the full range of immunostimulation from an attenuated bacterium. Significantly changing the concentration of the protein antigen, a common step in vaccine optimization, had no significant effect on the encapsulation efficiency of the co-loaded adjuvants.

This Example demonstrates that 1) PPSU vesicles can employ 2 distinct drug loading strategies: pre-assembly and post-assembly (FIG. 35) to stably load a diverse range of vaccine relevant molecules (Table 7 & FIG. 36); 2) loaded adjuvants remain active and have either equal or improved efficacy following encapsulation within PPSU nanogels (FIG. 36B); 3) PPSU multi-drug formulations can be rapidly and reproducibly fabricated using at least 4 separate model molecules (protein, DNA, lipids, & small molecules; see Table 7), and the concentration of protein antigen can be adjusted without significantly effecting the loading efficiency of the co-loaded adjuvants (FIG. 36C); 4) that proteomic analysis verified no leakage of proteins from PPSU nanogels following loading by either the pre- or post-assembly encapsulation strategies (FIG. 35B); 5) a novel trypsin proteolysis assay can assess the retention of protein bioactivity and solution accessibility following loading into PPSU NBMs (FIG. 35C,D); and 6) nanogel encapsulated trypsin retains its bioactivity by digesting free form FITC-BSA in the surrounding solution (FIG. 35D).

TABLE 7

Model molecular payloads and methods of detection for optimization of drug loading.

| Component | Solubility | Molecule Class | Function | Method of Detection | Detection Condition |
|---|---|---|---|---|---|
| Ovalbumin | Hydrophilic | Protein | Antigen | Alexa Flour™ 647 conjugate | Ex/Em: 650/668 nm |
| CpG | Hydrophilic | Nucleic acid/DNA | TLR9 agonist | FITC label | Ex/Em: 495/525 nm |
| LPS | Hydrophobic | Lipid amphiphile | TLR4 agonist | Cy3 label | Ex/Em: 550/570 nm |
| CL429 | Hydrophobic | Small molecule drug | TLR2/NOD2 agonist | Colorimetric (dye-metal complex) | 660 nm |
| 2'3'-cGAMP | Hydrophilic | Small molecule drug | STING agonist | LC-MS | N/A |

Standard pre-assembly method of PPSU nanogel formation and drug loading: The fabrication of 100 nm PPSU nanogel vesicles was performed utilizing a simple, one-step vortex mixing method. In brief, 2.5 mg of PPSU polymer (50 µL, 50 mg/mL in DMSO) was added with 100 µL of Milli-Q water and vortexed for 30 s. The resultant mixture was diluted with 500 µL Milli-Q water and then dialyzed (Thermo Scientific Slide-A-Lyzer MINI dialysis devices) against Milli-Q water/PBS to remove DMSO. The obtained nanostructures were utilized for further analysis. The antigen and adjuvants were loaded alone or simultaneously into PPSU nanogels via the method described above (FIG. 35A-method #1). The hydrophobic adjuvants CL429 (50 µg) or cy3-labelled LPS (25 or 150 µg) were added to the DMSO phase containing the polymer whereas the hydrophilic components model protein Ovalbumin, Alexa Fluor™ 647 Conjugate (25 µg) or FITC labeled CpG ODN (50 µg) or 2'3'-cGAMP (50 µg) were added to the aqueous phase. The unencapsulated antigen/adjuvants were removed by dialysis and the amount loaded into PPSU nanocarriers was quantified using validated spectrofluorimetric or LC-MS-based methods.

Novel post-assembly method of PPSU nanogel formation and drug loading: Interestingly, previously assembled and purified nanogels were found to stably capture diverse water soluble molecules when incubated in aqueous solutions (FIG. 35A-method #2). To demonstrate this method, the PPSU nanogels were first assembled in DMSO (in the absence of protein payload Trypsin). After assembly, the structures were centrifuged and washed with PBS to remove residual DMSO, after which 2 µg of Trypsin was added. Following a brief vortexing for only 5 min, the Trypsin-PPSU nanogels were centrifuged to pellet Trypsin-PPSU nanogels and gently resuspended in PBS. After washing 3x, the purified Trypsin-PPSU nanogels were resuspended in 1 mL PBS for storage at 4° C. This post-assembly strategy loads protein with equal stability as the pre-assembly strategy (FIG. 35B), but was advantageous for the retention of protein bioactivity (FIGS. 35C & D), since this method does not expose protein to DMSO solutions as described above in the standard pre-assembly method (FIG. 35A).

A proteomics-based assay for high sensitivity assessment of protein loading stability. Following loading of trypsin using either the pre- or post-assembly method, nanogels were incubated at room temperature for 48 h. PPSU vesicles were pelleted by centrifugation for isolation of free form trypsin in the supernatant that may have leaked out of the nanogels during the 48 h incubation. The supernatants were collected and mixed 1:1 with sinapinic acid matrix prepared in ultrapure water with 0.2% TFA. These mixtures were spotted onto a stainless steel MALDI disc (Bruker) and full-length Trypsin protein (~23 kDa) was detected by matrix assisted laser desorption ionization time-of-flight (MALDI-TOF) mass spectrometry (FIG. 35B). Positive ion mass spectra were collected in triplicate on a Bruker rapifleX MALDI Tissuetyper operating in linear TOF mode.

Trypsin proteolysis fluorescence-based assay. This assay was designed to determine whether an enzyme encapsulated within PPSU nanogels could both retain enzymatic activity as well as access protein substrates in the surrounding solution (FIGS. 35C & D). 2 µg/ml Trypsin (free protease or nanogel-embedded form) was incubated 1:1 with quenched 1 mg/mL of quenched FITC-BSA substrate. Four experimental groups were: 1) Free Trypsin (positive control), 2) Pre-assembly Trypsin-PPSU (formed by adding Trypsin during PPSU assembly, Method #1), 3)Post-assembly Trypsin-PPSU (formed by loading trypsin after PPSU assembly; Method #2), or 4) PPSU absent of Trypsin (negative control). Trypsin cleavage yields FITC-labeled peptides derived from the full-length protein, releasing the fluorophore from a quenched state to increase fluorescence. Proteolysis was therefore monitored by measuring the increase in fluorescence over a 1.5 h period (1 measurement per minute). Measurements were obtained in three replicates per condition.

MPLA will be employed as a nontoxic and clinically approved variant of LPS. To better mimic immunostimulation of an intracellular bacterium, STING agonist 2'3'-cGAMP will be incorporated and ovalbumin will be replaced with the tuberculosis vaccine candidate protein antigen Ag85B. Vaccine immunogenicity and efficacy will be assessed by both in vitro and in vivo assays that quantify changes in cytokine expression and T cell activation.

Figure 37:
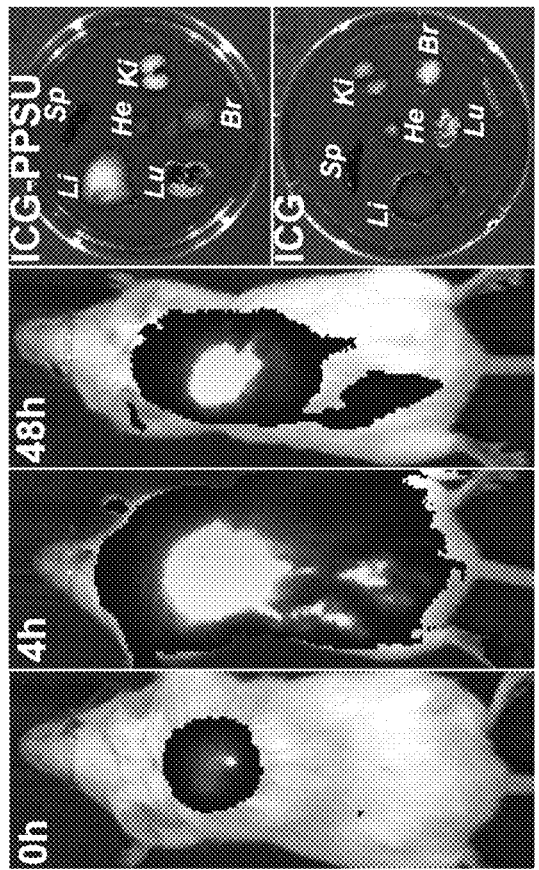
FIG. 37. PPSU nanogel biodistribution following subcutaneous (s.c.) injection. PPSU vesicular nanogels were loaded with NIRF imaging agent cardiogreen (ICG) and injected s.c. into mice for preliminary analysis by IVIS. Liver (Li), spleen (Sp), kidneys (Ki), heart (He), lung (Lu) and brain (Br) were extracted after 48 h for comparison of biodistribution between ICG-PPSU and free form ICG.

Assessment of PPSU NBM biodistribution and toxicity: Preliminary assessment of vesicular PPSU nanogel biodistribution 48 h after subcutaneous (s.c.) injection (relevant for vaccination) was performed using near infrared fluorescence (NIRF) agent cardiogreen (ICG) as previously published by the Scott lab[1]. ICG was stably loaded into nanogels using the pre-assembly method, which shifted the biodistribution from heart, brain and kidneys to primarily liver and kidneys (FIG. 37), as commonly observed for non-targeted nanocarriers[1]. Injections were well tolerated by mice, with no visible signs of toxicity or discomfort.

REFERENCES EXAMPLE 2

1. Yi S, Allen S D, Liu Y-G, Ouyang B Z, Li X, Augsornworawat P, Thorp E B, Scott E A. Tailoring Nanostructure Morphology for Enhanced Targeting of Dendritic Cells in Atherosclerosis. ACS Nano. 2016; 10(12):11290-303. doi: 10.1021/acsnano.6b06451.

The invention claimed is:

1. A nanostructure comprising synthetic self-assembling poly(propylene sulfone) (PPSU) homopolymers, wherein the nanostructure is capable of being loaded with cargo.

2. The nanostructure of claim 1, wherein the nanostructure is a vesicle-like nanostructure.

3. The nanostructure of claim 2, wherein the vesicle-like nanostructure has a diameter of less than 240 nm.

4. The nanostructure of claim 1, wherein the nanostructure is a bundle-like or micellar nanostructure.

5. A system for delivery of cargo to a target, the system comprising:
  (a) the nanostructure of claim 1; and
  (b) a cargo, wherein the cargo is capable of being loaded on the nanostructure.

6. The system of claim 5, wherein the nanostructure is a bundle-like, vesicle-like, or micellar nanostructure.

7. The system of claim 5, wherein the cargo is capable of being loaded on the nanostructure at an efficiency of at least 75%.

8. A method of producing the nanostructure of claim 1, the method comprising:
  mixing water and a solution of dimethyl sulfoxide (DMSO):poly(propylene sulfone (PPSU) at a ratio from about 2:1 to about 10:1, to form a monodisperse nanostructure of PPSU within the solution, wherein the nanostructure is capable of carrying a cargo.

9. The method of claim 8, wherein the nanostructure comprises a vesicle-like or micellar nanostructure.

10. The method of claim 9, wherein the nanostructure comprises bundle-like nanostructures/nanogel s.

11. The method of claim 10, further comprising adding a water-soluble cargo to the water before being mixed with the solution of DMSO:PPSU.

12. The method of claim 11, wherein the water-soluble cargo is a water-soluble drug, protein, DNA, RNA, peptide or compound.

13. A nanostructure made by the method of claim 8.

14. A method of loading a cargo in the nanostructure of claim 1, the method comprising:
  (a) mixing water with a solution of DMSO and (poly(propylene sulfone) (PPSU) in the presence of the cargo at a ratio from about 2:1 to about 10:1, to form a monodisperse nanostructure of PPSU comprising the cargo.

15. The method of claim 14, wherein the cargo is loaded at an efficiency of at least 75%.

16. The method of claim 14, wherein the cargo is loaded at a loading capacity of at least 75% (m/m).

17. The nanostructure of claim 1, wherein the nanostructure consists of PPSU homopolymers.

18. The nanostructure of claim 1, wherein each of the PPSU homopolymers comprises twenty sulfones.

* * * * *